(12) United States Patent
Choi et al.

(10) Patent No.: US 10,766,857 B2
(45) Date of Patent: Sep. 8, 2020

(54) COMPOUND HAVING BLT INHIBITORY ACTIVITY AND COMPOSITION, FOR PREVENTING OR TREATING INFLAMMATORY DISEASES, COMPRISING SAME AS ACTIVE INGREDIENT

(71) Applicants: DONGGUK UNIVERSITY INDUSTRY-ACADEMIC COOPERATION FOUNDATION, Seoul (KR); KOREA UNIVERSITY RESEARCH AND BUSINESS FOUNDATION, Seoul (KR)

(72) Inventors: Yongseok Choi, Goyang-si (KR); Jae-Hong Kim, Seongnam-si (KR); Kyeong Lee, Goyang-si (KR); Hyo-Kyung Han, Seoul (KR); Jun Dong Wei, Seoul (KR); Jinsun Kwon, Yongin-si (KR); Ja-Il Goo, Seoul (KR)

(73) Assignees: DONGGUK UNIVERSITY INDUSTRY-ACADEMIC COOPERATION FOUNDATION, Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 16/181,953

(22) Filed: Nov. 6, 2018

(65) Prior Publication Data
US 2019/0071395 A1 Mar. 7, 2019

Related U.S. Application Data

(62) Division of application No. 15/745,337, filed as application No. PCT/KR2016/008069 on Jul. 23, 2016, now Pat. No. 10,179,764.

(30) Foreign Application Priority Data

| Jul. 24, 2015 | (KR) | 10-2015-0105097 |
| Jul. 22, 2016 | (KR) | 10-2016-0093762 |

(51) Int. Cl.

| C07C 311/21 | (2006.01) |
| C07C 233/07 | (2006.01) |
| C07D 213/56 | (2006.01) |
| C07C 233/51 | (2006.01) |
| C07C 233/88 | (2006.01) |
| C07C 235/34 | (2006.01) |
| C07C 237/42 | (2006.01) |
| C07C 311/16 | (2006.01) |
| C07D 295/192 | (2006.01) |
| C07D 295/205 | (2006.01) |
| A61P 11/06 | (2006.01) |
| A61P 35/00 | (2006.01) |
| C07C 275/32 | (2006.01) |
| C07D 257/04 | (2006.01) |
| C07D 295/185 | (2006.01) |
| C07D 211/06 | (2006.01) |
| C07D 241/04 | (2006.01) |
| C07D 265/30 | (2006.01) |

(52) U.S. Cl.
CPC ............ *C07C 311/21* (2013.01); *A61P 11/06* (2018.01); *A61P 35/00* (2018.01); *C07C 233/07* (2013.01); *C07C 233/51* (2013.01); *C07C 233/88* (2013.01); *C07C 235/34* (2013.01); *C07C 237/42* (2013.01); *C07C 275/32* (2013.01); *C07C 311/16* (2013.01); *C07D 211/06* (2013.01); *C07D 213/56* (2013.01); *C07D 241/04* (2013.01); *C07D 257/04* (2013.01); *C07D 265/30* (2013.01); *C07D 295/185* (2013.01); *C07D 295/192* (2013.01); *C07D 295/205* (2013.01)

(58) Field of Classification Search
CPC .............................. A61P 11/06; C07C 311/21
See application file for complete search history.

(56) References Cited

U.S. PATENT DOCUMENTS

| 7,005,437 B2 | 2/2006 | Priepke et al. |
| 10,179,764 B2 * | 1/2019 | Choi .................... C07D 241/04 |
| 2006/0264415 A1 | 11/2006 | Leit De Moradei |

FOREIGN PATENT DOCUMENTS

| CN | 104045552 A | 9/2014 |
| KR | 20130017073 A | 2/2013 |

(Continued)

OTHER PUBLICATIONS

International Search Report for International Application No. PCT/KR2016/008069 ( 3 Pages) ( dated Nov. 8, 2016).

(Continued)

*Primary Examiner* — Golam M Shameem
(74) *Attorney, Agent, or Firm* — Lucas & Mercanti, LLP

(57) ABSTRACT

The present invention relates to a novel compound showing leukotriene B4 receptor 2 (BLT2) inhibitory activity and a pharmaceutical composition, for preventing or treating inflammatory diseases, having same as an active ingredient. The inventors identified a novel compound containing BTL2 inhibitory activity, and experimentally confirmed that the present novel compound had an excellent effect on the enhancement of the cancer cell death, on the inhibition of the metastasis and chemotactic mobility, and on the anti-asthma activity. Therefore, the present novel compound can be used as a very effective pharmaceutical component for treating the inflammatory-related diseases.

11 Claims, 28 Drawing Sheets

(56) References Cited

FOREIGN PATENT DOCUMENTS

KR          20150080428 A     7/2015
WO             0240466 A2     5/2002

OTHER PUBLICATIONS

Yokomizo et al., A Second Leukotriene B4 Receptor, BLT2: A New Therapeutic Target in Inflammation and Immunological Disorders, J. Exp. Med., 2000, pp. 421-431, vol. 192 No. 3.
Kim et al., BLT2 phosphorylation at Thr355 by Akt is necessary for BLT2-mediated chemotaxis, Federation of European Biochemical Societies, 2011, pp. 3501-3506, vol. 585.
Kim et al., Up-regulation of BLT2 is critical for the survival of bladder cancer cells, Experimental and Molecular Medicine, 2011, vol. 43 No. 3.
Kim et al., BLT2 promotes the invasion and metastasis of aggressive bladder cancer cells through a reactive oxygen species-linked pathway, Free Radical Biology & Medicine, 2010, pp. 1072-1081, vol. 49.
Kim et al., Leukotriene B4 receptor-2 contributes to chemoresistance of SK-OV-3 ovarian cancer cells through activation of signal transducer and activator of transcription-3-linked cascade, Biochimica et Biophysica Acta, 2016, pp. 236-243, vol. 1863.
Kim et al., The leukotriene B4 receptor-2 promotes invasiveness and metastasis of ovarian cancer cells through STAT3-dependent up-regulation of matrix metalloproteinase 2, 2016.

Kim et al., Activation of the BLT2-ROS cascade following detachment confers anoikis resistance in prostate cancer cells, J. Biol. Chem., 2013.
Kim et al., Role of the BLT2, a leukotriene B4 receptor, in Ras transformation, Oncogene, 2004, pp. 9259-9268, vol. 23.
Kim et al., Role of the Low-Affinity Leukotriene B4 Receptor BLT2 in VEGF-Induced Angiogenesis, Arteriosclerosis, Thrombosis, and Vascular Biology, 2009, pp. 915-920.
Kim et al., Ras Promotes Transforming Growth Factor-Beta (TGF-Beta)-induced Epithelial-Mesenchymal Transition via a Leukotriene B4 Receptor-2-linked Cascade in Mammary Epithelial Cells, The Journal of Biological Chemistry, 2014, pp. 22151-22160, vol. 289 No. 32.
Kim et al., Low-dose UVB irradiation stimulates matrix metalloproteinase-1 expression via a BLT2-linked pathway in HaCaT cells, Experimental and Molecular Medicine, 2010, pp. 833-841, vol. 42 No. 12.
Kim et al., BLT2 is a pro-tumorigenic mediator during cancer progression and a therapeutic target for anti-cancer drug development, Am. J. Cancer, 2013, pp. 347-355, vol. 3 No. 4.
Kim et al., UVB Radiation Induces Apoptosis in Keratinocytes by Activating a Pathway Linked to "BLT2-Reactive Oxygen Species", Journal of Investigative Dermatology, 2010, pp. 1095-1106.
Haribadu et al., Nonredundant Roles for Leukotriene B4 Receptors BLT1 and BLT2 in Inflammatory Arthritis, The Journal of Immunology, 2010, pp. 3049-3056, vol. 185.

* cited by examiner

COMPOUND HAVING BLT INHIBITORY ACTIVITY AND COMPOSITION, FOR PREVENTING OR TREATING INFLAMMATORY DISEASES, COMPRISING SAME AS ACTIVE INGREDIENT

CROSS-REFERENCE TO RELATED APPLICATIONS

This Application is a Divisional of U.S. application Ser. No. 15/745,337, filed Mar. 30, 2018, Which in turn is 371 of PCT/KR2016/008069, filed Jul. 23, 2016, which claims the benefit of priority from Korean Patent Application No. 10-2015-0105097, filed Jul. 24, 2015 and Korean Patent Application No. 10-2016-0093762, filed Jul. 22, 2016, the contents of each of which are incorporated herein by reference.

TECHNICAL FIELD

The present invention relates to a novel compound and a use thereof, and more particularly, to a novel compound exhibiting a leukotriene B4 receptor 2 (BLT2) inhibitory activity and a pharmaceutical composition for preventing or treating an inflammatory disease, which includes the novel compound as an active ingredient.

BACKGROUND ART

An inflammatory response is one of the human immune systems activated by various action mechanisms to defend against physical actions, chemicals, bacterial infections, or immunological stimuli, which are applied to living organisms or tissue. However, when such inflammatory response persists, rather, damage to a mucous membrane is promoted, and therefore it has been noted that inflammatory diseases including rheumatoid arthritis, atherosclerosis, gastritis, asthma, etc. are caused by erythema, a fever, swelling, pain, or dysfunction. Such an inflammatory response is classified into acute inflammation and chronic inflammation as time passes. The acute inflammation is an inflammatory response lasting several days to several weeks, and causes a symptom such as erythema, a fever, pain, or swelling, whereas the chronic inflammation is a long-term inflammatory state for several years to decades, and involves a histological change such as fibrosis or the destruction of tissue caused by the infiltration of monocytes, proliferation of fibroblasts or capillaries, or an increase in connective tissue.

Specifically, when inflammatory stimuli are applied to the living organism, locally, histamine, bradykinin, prostaglandins, nitric oxide (NO), all types of pro-inflammatory cytokines, etc. are synthesized and secreted, and cause erythema, a fever, pain, or swelling as well as vasodilation. Particularly, in inflammation in the body, in addition to common immune factors, for example, cytokines such as interferon-γ (INF-γ), tumor necrosis factor-α (TNF-α), interleukin-1 (IL-1), and interleukin-6 (IL-6), nitric oxide (NO) and prostaglandin E2 (PGE2) are well known as major proinflammatory materials.

Conventionally, the termination of an inflammation response is known as a phenomenon naturally and passively occurring due to a decrease in levels of materials initiating inflammation, but it was found that the termination of inflammation is actively promoted by lipoxins, resolvins, or protectins, which were discovered by Serhan et al., like prostaglandins, which are involved in the initiation of inflammation. For example, it has been reported that Resolvin E1 is effective for pain, and RvE1 induces the termination of inflammation and is effective in treating an allergic inflammatory disease. In addition, it has been reported that low levels of factors actively promoting the termination of such inflammation in a chronic inflammatory disease, that is, lipoxin A4 and lipoxin induced by aspirin are shown in asthmatic patients and atherosclerotic patients.

Accordingly, while various attempts to find novel materials for inducing the termination of inflammation and thus to treat diseases associated with abnormal inflammation termination have been made (Korean Unexamined Patent Application No. 10-2015-0011875), a compound known to be included in lipoxins, resolvins, etc. is metabolically unstable and thus rapidly degraded in the body due to several double bonds in its structure, and is somewhat difficult to be developed as a drug by mass production of a material, thereby having a great problem in drugability.

Meanwhile, leukotriene B4 (LTB$_4$) is a group of inflammatory lipid mediators synthesized from arachidonic acid (AA) via a 5-lipoxygenase pathway mediating acute and chronic inflammation. LTB$_4$ is known to give a biological effect by binding to two types of receptors such as BLT1 and BLT2. Leukotriene B4 receptor 2 (BLT2), as one among the G protein-coupled receptor (GPCR) family, is a receptor having low affinity to LTB$_4$, and a lipid mediator of arachidonic acid (AA) induced via a 5-lipoxygenase-dependent pathway.

Accordingly, to solve the above-mentioned conventional problems, the inventors prepared a novel compound exhibiting a BLT2 inhibitory activity while conducting research to develop a material for inducing the effective termination of inflammation, and first invented a therapeutic agent for an inflammatory disease, which includes the above-mentioned compound.

DISCLOSURE

Technical Problem

The present invention is provided to solve the above-mentioned problems, and the inventors confirmed a therapeutic effect of a novel compound exhibiting a BLT2 inhibitory activity on an inflammatory disease, and based on this, the present invention was completed.

Therefore, an object of the present invention is to provide a novel compound exhibiting a BLT2 inhibitory activity or a pharmaceutically acceptable salt thereof.

Another object of the present invention is to provide a pharmaceutical composition for preventing or treating an inflammatory disease, which includes the novel compound or pharmaceutically acceptable salt thereof as an active ingredient.

However, technical problems to be solved in the present invention are not limited to the above-described problems, and other problems which are not described herein will be fully understood by those of ordinary skill in the art from the following description.

Technical Solution

To achieve these objects of the present invention, the present invention provides a novel compound exhibiting a BLT2 inhibitory activity or a pharmaceutically acceptable salt thereof.

According to an exemplary embodiment of the present invention, the compound may be selected from the group consisting of tert-butyl 4-(4-(3-(N-phenylpentaneamido)

prop-1-ynyl)benzoyl)piperazine-1-carboxylate; N-phenyl-N-(3-(4-(piperazine-1-carbonyl)phenyl)prop-2-ynyl)pentaneamide; N-(3-(4-(4-methylpiperazine-1-carbonyl)phenyl)prop-2-ynyl)-N-phenylpentaneamide; N-(3-(4-(4-ethylpiperazine-1-carbonyl)phenyl)prop-2-ynyl)-N-phenylpentaneamide; N-(3-(4-(4-isopropylpiperazine-1-carbonyl)phenyl)prop-2-ynyl)-N-phenylpentaneamide; N-(3-(4-(4-(2-hydroxyethyl)piperazine-1-carbonyl)phenyl)prop-2-ynyl)-N-phenylpentaneamide; N-(3-(4-(4-(cyclopropylmethyl)piperazine-1-carbonyl)phenyl)prop-2-ynyl)-N-phenylpentaneamide; N-(3-(4-(4-cyclohexylpiperazine-1-carbonyl)phenyl)prop-2-ynyl)-N-phenylpentaneamide; N-(3-(4-(4-(cyclohexylmethyl)piperazine-1-carbonyl)phenyl)prop-2-ynyl)-N-phenylpentaneamide; N-(3-(4-(4-isobutylpiperazine-1-carbonyl)phenyl)prop-2-ynyl)-N-phenylpentaneamide; N-phenyl-N-(3-(4-(4-(prop-2-ynyl)piperazine-1-carbonyl)phenyl)prop-2-ynyl)pentaneamide; N-(3-(4-(4-cyanopiperazine-1-carbonyl)phenyl)prop-2-ynyl)-N-phenylpentaneamide; tert-butyl 4-(4-(3-(N-(3-fluorophenyl)pentaneamido)prop-1-ynyl)benzoyl)piperazine-1-carboxylate; N-(3-fluorophenyl)-N-(3-(4-(piperazine-1-carbonyl)phenyl)prop-2-ynyl)pentaneamide; N-(3-fluorophenyl)-N-(3-(4-(4-isopropylpiperazine-1-carbonyl)phenyl)prop-2-ynyl)pentaneamide; tert-butyl 4-(4-(3-(N-(4-fluorophenyl)pentaneamido)prop-1-ynyl)benzoyl)piperazine-1-carboxylate; N-(4-fluorophenyl)-N-(3-(4-(piperazine-1-carbonyl)phenyl)prop-2-ynyl)pentaneamide; N-(4-fluorophenyl)-N-(3-(4-(4-isopropylpiperazine-1-carbonyl)phenyl)prop-2-ynyl)pentaneamide; N-(3-(4-(morpholine-4-carbonyl)phenyl)prop-2-ynyl)-N-phenylpentaneamide; N-phenyl-N-(3-(4-(piperidine-1-carbonyl)phenyl)prop-2-ynyl)pentaneamide; N,N-diethyl-4-(3-(N-phenylpentaneamido)prop-1-ynyl)benzamide; N-phenyl-N-(3-(3-(piperazine-1-carbonyl)phenyl)prop-2-ynyl)pentaneamide; N-(3-(3-(4-methylpiperazine-1-carbonyl)phenyl)prop-2-ynyl)-N-phenylpentaneamide; N-(3-(3-(4-isopropylpiperazine-1-carbonyl)phenyl)prop-2-ynyl)-N-phenylpentaneamide; tert-butyl-4-(3-(3-(N-(4-fluorophenyl)pentaneamido)prop-1-ynyl)benzoyl)piperazine-1-carboxylate; N-(4-fluorophenyl)-N-(3-(3-(piperazine-1-carbonyl)phenyl)prop-2-ynyl)pentaneamide; N-(4-fluorophenyl)-N-(3-(3-(4-isopropylpiperazine-1-carbonyl)phenyl)prop-2-ynyl)pentaneamide; N-(3-(4-hydroxyphenyl)prop-2-ynyl)-N-phenylpentaneamide; 2-(4-(3-(N-phenylpentaneamido)prop-1-ynyl)phenoxy)acetic acid; tert-butyl 4-(5-(3-((N-phenylpentaneamido)prop-1-yn-1-yl)picolinoyl)piperazine-1-carboxylate; N-phenyl-N-(3-(6-(piperazine-1-carbonyl)pyridine-3-yl)prop-2-yn-1-yl)pentaneamide; N-(3-(6-isopropylpiperazine-1-carbonyl)pyridine-3-yl)prop-2-yn-1-yl)pentaneamide; N,N-diethyl-4-(3-(N-(3-fluorophenyl)pentamido)prop-1-yn-1-yl)benzamide; N,N-diethyl-4-(3-(N-(4-fluorophenyl)pentamido)prop-1-yn-1-yl)benzamide; N-(3-(4-(N,N-diethylsulfamoyl)phenyl)prop-2-ynyl)-N-phenylpentamide; N-(3-(4-(N-isopropylsulfamoyl)phenyl)prop-2-ynyl)-N-phenylpentamide; tert-butyl 4-(3-(N-phenylpentaneamido)prop-1-yn-1-yl)benzoate; 4-(3-(N-phenylpentaneamido)pro-1-yn-1-yl)benzoic acid; N-ethyl-4-(3-(N-phenylpentaneamido)prop-1-yn-1-yl)benzamide; N-(2-(diethylamino)ethyl)-4-(3-(N-phenylpentaneamido)prop-1-yn-1-yl)benzamide; ethyl 2-(4-(3-(N-phenylpentaneamido)prop-1-yn-1-yl)benzamido)acetate; 2-(4-(3-(N-phenylpentaneamido)prop-1-yn-1-yl)benzamido)acetic acid; methyl 2-(4-(3-(N-phenylpentaneamido)prop-1-yn-1-yl)benzamido)propanoate; 2-(4-(3-(N-phenylpentaneamido)prop-1-yn-1-yl)benzamido)propionic acid; 2-(4-(3-(N-(3-fluorophenyl)pentaneamido)prop-1-ynyl)phenoxy)acetic acid; and 2-(4-(3-(N-(4-fluorophenyl)pentaneamido)prop-1-ynyl)phenoxy)acetic acid.

The present invention provides a pharmaceutical composition for preventing or treating an inflammatory disease, which includes the novel compound or a pharmaceutically acceptable salt thereof as an active ingredient.

According to an exemplary embodiment of the present invention, the inflammatory disease may be selected from the group consisting of asthma, atherosclerosis, cancer, pruritus, rheumatoid arthritis and inflammatory enteropathy.

According to another exemplary embodiment of the present invention, the composition may inhibit BLT2 activity.

The present invention provides a method for treating an inflammatory disease, which includes administering the pharmaceutical composition to a subject.

The present invention provides a use of the composition including the novel compound or a pharmaceutically acceptable salt thereof to treat an inflammatory disease.

Advantageous Effects

The present invention relates to a new compound exhibiting BLT2 inhibitory activity and a pharmaceutical composition for preventing or treating an inflammatory disease, which includes the compound. The inventors identified a novel compound exhibiting BTL2 inhibitory activity to solve problems of a conventional material for treating an inflammatory disease, for example, instability in the living organism and difficulty in mass production, and experimentally confirmed that the compound has excellent effects of improving the death of cancer cells and inhibiting cancer cell metastasis, a chemotactic motility inhibitory effect, and an antiasthma effect, and therefore the compound is expected to be effectively used as a pharmaceutical composition for treating an inflammatory disease.

MODES OF THE INVENTION

Figure 1A:
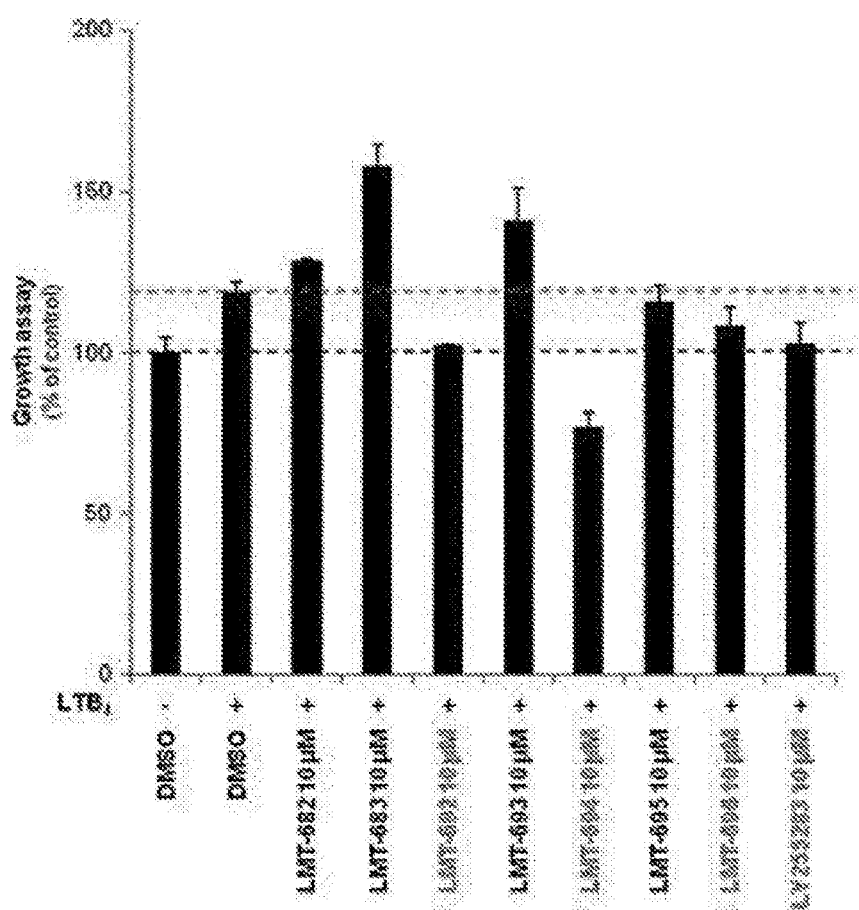
FIGS. 1A to 1E show the results of confirming a growth inhibitory effect in BLT2-expressing cells (CHO-BLT2 cells) caused by treatment of a compound of the present invention.
Figure 1B:
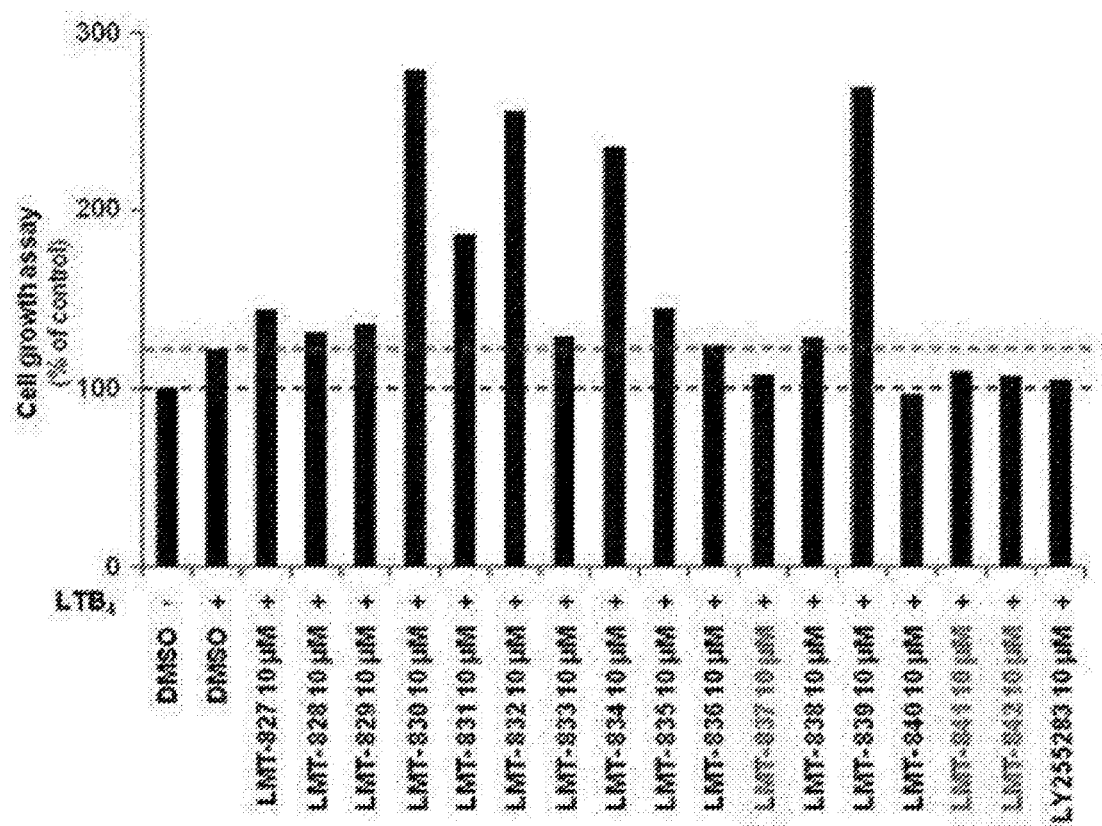
Figure 1C:
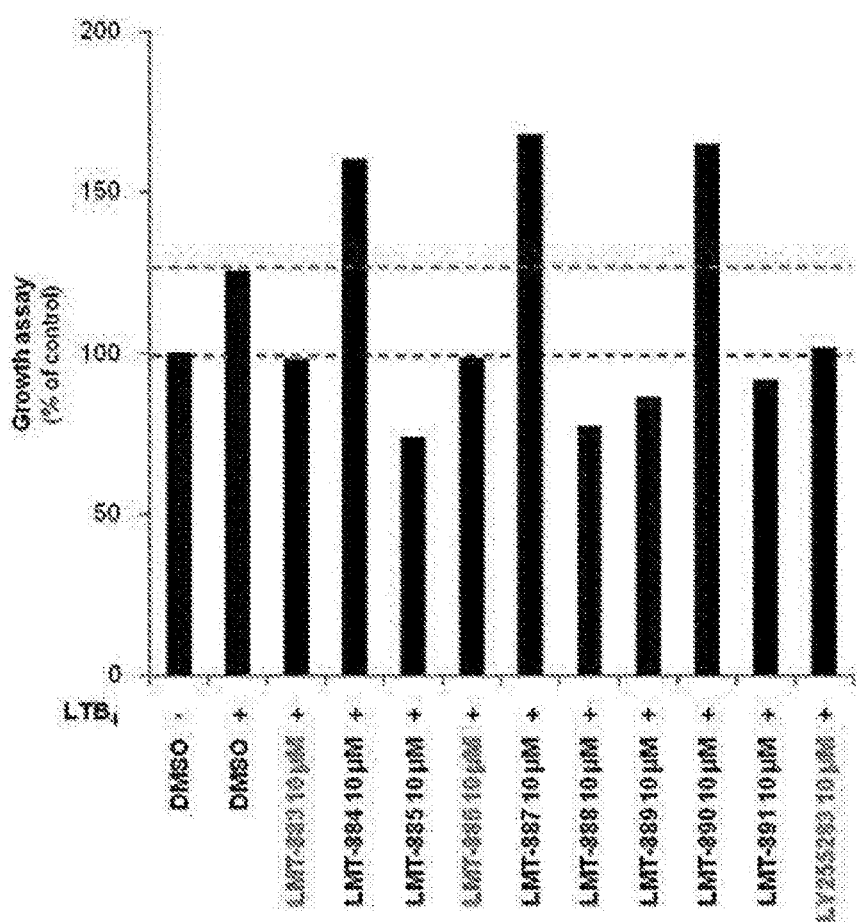
Figure 1D:
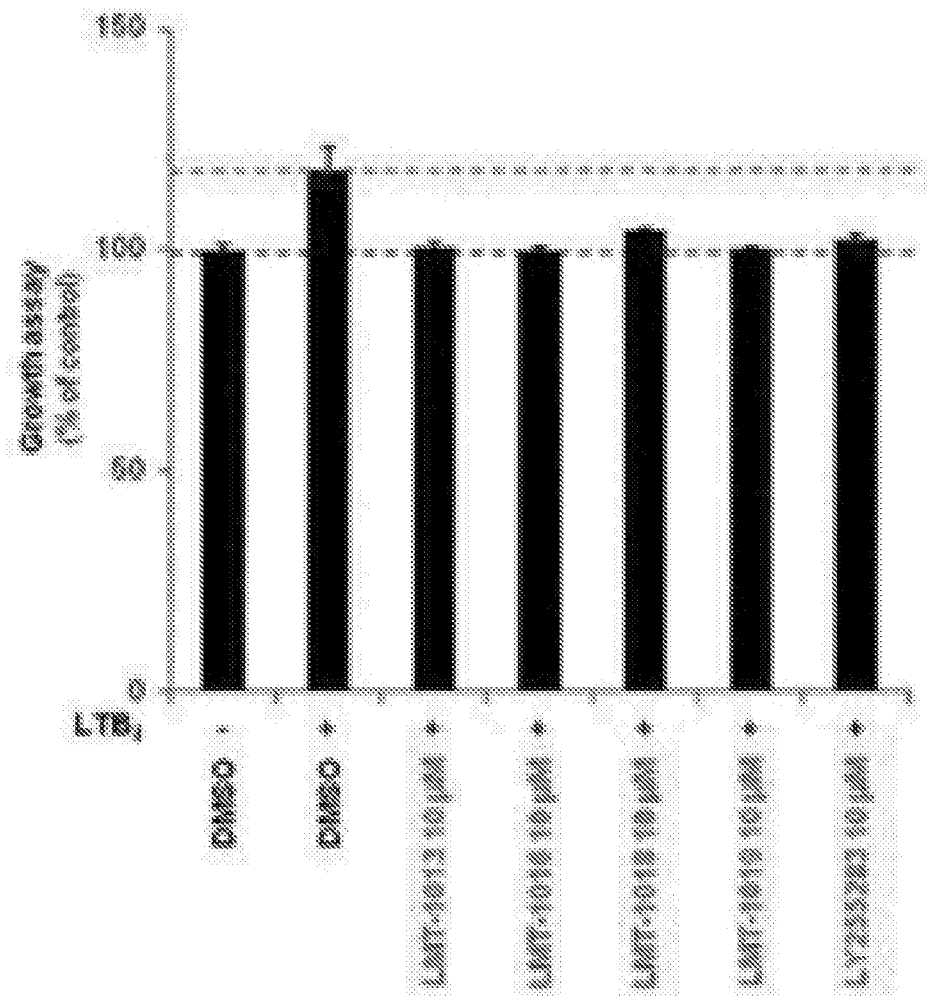
Figure 1E:
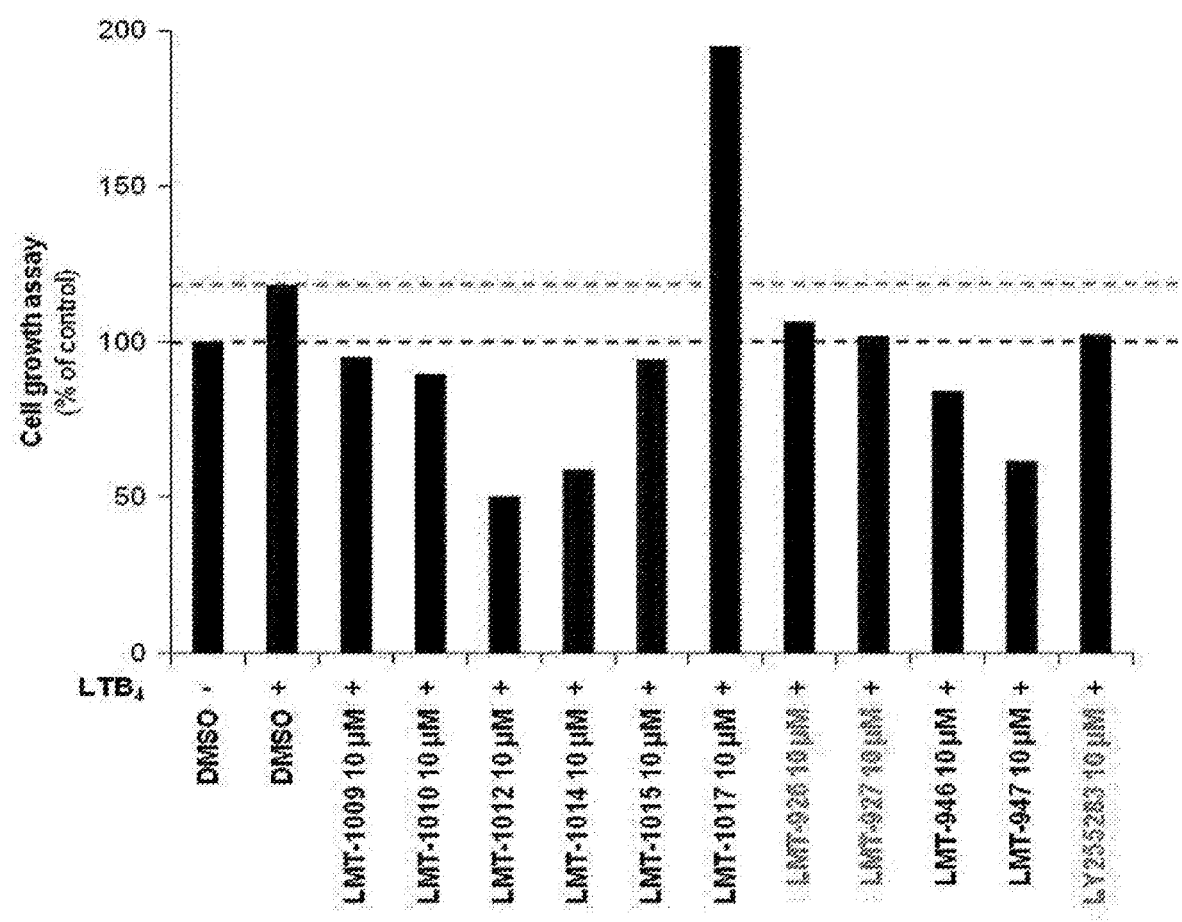

The inventors specifically identified effects of improving the death of cancer cells, the inhibition of cancer cell metastasis and the inhibition of BLT2-dependent chemotactic motility, and an antiasthma effect based on the fact that the growth of BLT2-expressing cells can be considerably inhibited when a novel compound prepared in an example is treated, and therefore, the present invention was completed.

Hereinafter, the present invention will be described in detail.

The present invention provides a compound represented by Formula 1 below or a pharmaceutically acceptable salt thereof.

[Formula 1]

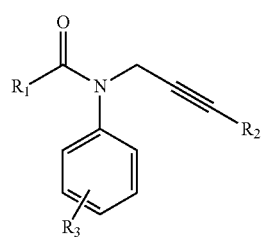

In Formula 1,
$R_1$ may be a $C_1$ to $C_{10}$ alkyl,
$R_2$ may be

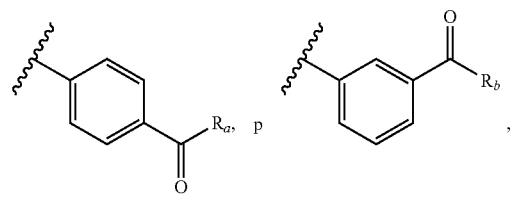

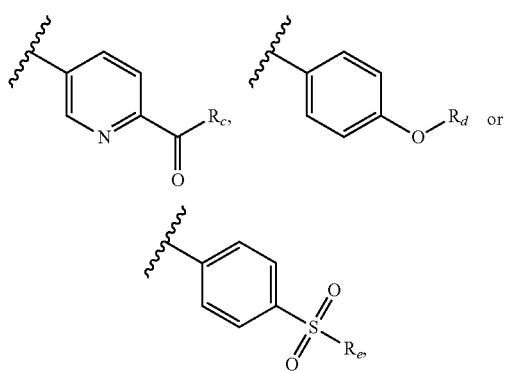

$R_a$ may be

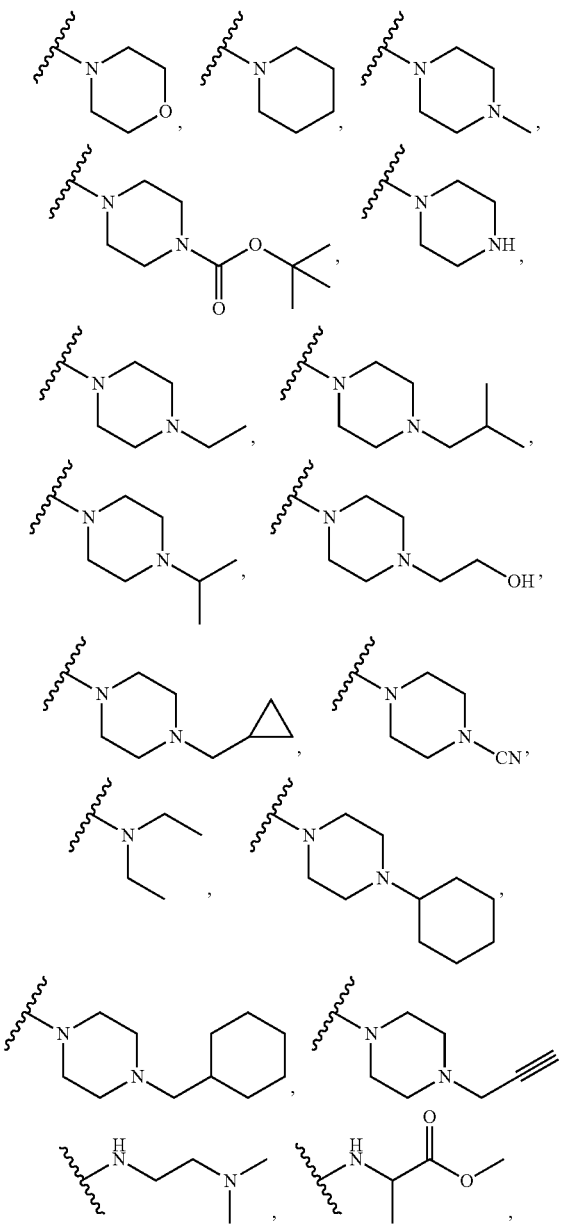

-continued or hydroxy, $R_b$ may be $R_c$ may be $R_d$ may be hydrogen or $R_e$ may be and $R_3$ may be hydrogen or fluorine.

Exemplary examples of the compound represented by Formula 1 according to the present invention are as follows: tert-butyl 4-(4-(3-(N-phenylpentaneamido)prop-1-ynyl)benzoyl)piperazine-1-carboxylate; N-phenyl-N-(3-(4-(piperazine-1-carbonyl)phenyl)prop-2-ynyl)pentaneamide; N-(3-(4-(4-methylpiperazine-1-carbonyl)phenyl)prop-2-ynyl)-N-phenylpentaneamide; N-(3-(4-(4-ethylpiperazine-1-carbonyl)phenyl)prop-2-ynyl)-N-phenylpentaneamide; N-(3-(4-(4-isopropylpiperazine-1-carbonyl)phenyl)prop-2-ynyl)-N-phenylpentaneamide; N-(3-(4-(4-(2-hydroxyethyl)piperazine-1-carbonyl)phenyl)prop-2-ynyl)-N-phenylpentaneamide; N-(3-(4-(4-(cyclopropylmethyl)piperazine-1-carbonyl)phenyl)prop-2-ynyl)-N-phenylpentaneamide; N-(3-(4-(4-cyclohexylpiperazine-1-carbonyl)phenyl)prop-2-ynyl)-N-phenylpentaneamide; N-(3-(4-(4-(cyclohexylmethyl)piperazine-1-carbonyl)phenyl)prop-2-ynyl)-N-phenylpentaneamide; N-(3-(4-(4-isobutylpiperazine-1-carbonyl)phenyl)prop-2-ynyl)-N-phenylpentaneamide; N-phenyl-N-(3-(4-(4-(prop-2-ynyl)piperazine-1-carbonyl)phenyl)prop-2-ynyl)pentaneamide; N-(3-(4-(4-cyanopiperazine-1-carbonyl)phenyl)prop-2-ynyl)-N-phenylpentaneamide; tert-butyl 4-(4-(3-(N-(3-fluorophenyl)pentaneamido)prop-1-ynyl)benzoyl)piperazine-1-carboxylate; N-(3-fluorophenyl)-N-(3-(4-(piperazine-1-carbonyl)phenyl)prop-2-ynyl)pentaneamide; N-(3-fluorophenyl)-N-(3-(4-(4-isopropylpiperazine-1-carbonyl)phenyl)prop-2-ynyl)pentaneamide; tert-butyl 4-(4-(3-(N-(4-fluorophenyl)pentaneamido)prop-1-ynyl)benzoyl)piperazine-1-carboxylate; N-(4-fluorophenyl)-N-(3-(4-(piperazine-1-carbonyl)phenyl)prop-2-ynyl)pentaneamide; N-(4-fluorophenyl)-N-(3-(4-(4-isopropylpiperazine-1-carbonyl)phenyl)prop-2-ynyl)pentaneamide; N-(3-(4-(morpholine-4-carbonyl)phenyl)prop-2-ynyl)-N-phenylpentaneamide; N-phenyl-N-(3-(4-(piperidine-1-carbonyl)phenyl)prop-2-ynyl)pentaneamide; N,N-diethyl-4-(3-(N-phenylpentaneamido)prop-1-ynyl)benzamide; N-phenyl-N-(3-(3-(piperazine-1-carbonyl)phenyl)prop-2-ynyl)pentaneamide; N-(3-(3-(4-methylpiperazine-1-carbonyl)phenyl)prop-2-ynyl)-N-phenylpentaneamide; N-(3-(3-(4-isopropylpiperazine-1-carbonyl)phenyl)prop-2-ynyl)-N-phenylpentaneamide; tert-butyl-4-(3-(3-(N-(4-fluorophenyl)pentaneamido)prop-1-ynyl)benzoyl)piperazine-1-carboxylate; N-(4-fluorophenyl)-N-(3-(3-(piperazine-1-carbonyl)phenyl)prop-2-ynyl)pentaneamide; N-(4-fluorophenyl)-N-(3-(3-(4-isopropylpiperazine-1-carbonyl)phenyl)prop-2-ynyl)pentaneamide; N-(3-(4-hydroxyphenyl)prop-2-ynyl)-N-phenylpentaneamide; 2-(4-(3-(N-phenylpentaneamido)prop-1-ynyl)phenoxy)acetic acid; tert-butyl 4-(5-(3-(N-phenylpentaneamido)prop-1-yn-1-yl)picolinoyl)piperazine-1-carboxylate; N-phenyl-N-(3-(6-(piperazine-1-carbonyl)pyridine-3-yl)prop-2-yn-1-yl)pentaneamide; N-(3-(6-isopropylpiperazine-1-carbonyl)pyridine-3-yl)prop-2-yn-1-yl)pentaneamide; N,N-diethyl-4-(3-(N-(3-fluorophenyl)pentamido)prop-1-yn-1-yl)benzamide; N,N-diethyl-4-(3-(N-(4-fluorophenyl)

pentamido)prop-1-yn-1-yl)benzamide; N-(3-(4-(N,N-diethylsulfamoyl)phenyl)prop-2-ynyl)-N-phenylpentamide; N-(3-(4-(N-isopropylsulfamoyl)phenyl)prop-2-ynyl)-N-phenylpentamide; tert-butyl 4-(3-(N-phenylpentaneamido)prop-1-yn-1-yl)benzoate; 4-(3-(N-phenylpentaneamido)pro-1-yn-1-yl)benzoic acid; N-ethyl-4-(3-(N-phenylpentaneamido)prop-1-yn-1-yl)benzamide; N-(2-(diethylamino)ethyl)-4-(3-(N-phenylpentaneamido)prop-1-yn-1-yl)benzamide; ethyl 2-(4-(3-(N-phenylpentaneamido)prop-1-yn-1-yl)benzamido)acetate; 2-(4-(3-(N-phenylpentaneamido)prop-1-yn-1-yl)benzamido)acetic acid; methyl 2-(4-(3-(N-phenylpentaneamido)prop-1-yn-1-yl)benzamido)propanoate; 2-(4-(3-(N-phenylpentaneamido)prop-1-yn-1-yl)benzamido)propionic acid; 2-(4-(3-(N-(3-fluorophenyl)pentaneamido)prop-1-ynyl)phenoxy)acetic acid; and 2-(4-(3-(N-(4-fluorophenyl)pentaneamido)prop-1-ynyl)phenoxy)acetic acid.

The term "pharmaceutically acceptable" used herein refers to a compound or composition that is suitable to be used in contact with a subject's (e.g., a human) tissue due to a reasonable benefit/risk ratio without excessive toxicity, irritation, allergic reactions, or other problems or complications, and included within the scope of sound medical judgment.

The term "salt" used herein is an acid addition salt formed by a pharmaceutically acceptable free acid. The acid addition salt is obtained from inorganic acids such as hydrochloric acid, nitric acid, phosphoric acid, sulfuric acid, hydrogen bromide, hydrogen iodide, nitride and phosphorous acid, and non-toxic organic acids such as aliphatic mono and dicarboxylates, phenyl-substituted alkanoates, hydroxyl alkanoates and alkandioates, aromatic acids, aliphatic and aromatic sulfonic acids. Such pharmaceutically non-toxic salts include sulfates, pyrosulfates, bisulfates, sulfites, bisulfites, nitrates, phosphates, monohydrogen phosphates, dihydrogen phosphates, metaphosphates, pyrophosphate chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methylbenzoates, dinitrobenzoates, hydroxylbenzoates, methoxybenzoates, phthalates, terephthalates, benzenesulfonates, toluenesulfonates, chlorobenzenesulfonates, xylenesulfonates, phenylacetates, phenylpropionates, phenylburyrates, citrates, lactates, β-hydroxylbutyrates, glycolates, malates, tartrates, methanesulfonates, propanesulfonates, naphthalene-1-sulfonates, naphthalene-2-sulfonates, and mandelates.

The acid addition salt according to the present invention may be prepared by a conventional method, for example, dissolving compounds represented by Formulas 1 to 4 in an excessive acid aqueous solution, and precipitating the resulting salt using a water-miscible organic solvent, for example, methanol, ethanol, acetone or acetonitrile. In addition, the acid addition salt according to the present invention may be prepared by evaporating a solvent or an excessive acid from this mixture, and then dehydrating the resulting mixture or suction-filtrating a precipitated salt.

In addition, the pharmaceutically acceptable metal salt may be prepared using a base. An alkali metal or alkali earth metal salt may be obtained by, for example, dissolving a compound in an excessive amount of an alkali metal hydroxide or alkali earth metal hydroxide solution, filtering an insoluble compound salt, and dehydrating the remaining solution through evaporation. Here, a sodium, potassium or calcium salt is pharmaceutically appropriate for the metal salt. Also, a silver salt corresponding to the metal salt is obtained by a reaction between an alkali metal or alkali earth metal salt and a suitable silver salt (e.g., silver nitrate).

In an exemplary embodiment of the present invention, novel compounds exhibiting a BLT2 inhibitory activity were prepared (see Examples 1 to 46), and it was confirmed that the growth of BLT2-expressing cells were inhibited by the treatment of the novel compound (see Experimental Example 2). In addition, it was confirmed that chemotactic motility of the BLT2-expressing cells can be inhibited (see Experimental Example 3). In addition, an $LTB_4$ and BLT2 binding inhibitory effect was confirmed using the compound (see Experimental Example 4), the inhibition of reactive oxygen species in cells, the inhibition of IL-8 expression, the inhibition of cancer cell invasion, and the inhibition of cancer cell metastasis were confirmed (see Experimental Example 5), and it was also specifically confirmed that the compounds have effects of reducing airway hyperresponsiveness (AHR), inhibiting IL-4 generation and inhibiting the influx of immune cells into a mouse abdominal cavity in asthma-induced mice (see Experimental Example 6), and therefore it was confirmed that the compounds can be very effectively used as pharmaceutical composition for an inflammatory disease.

Thus, the present invention provides a pharmaceutical composition for preventing or treating an inflammatory disease, which includes the compound or a pharmaceutically acceptable salt thereof.

Meanwhile, the term "prevention" used herein refers to all actions of inhibiting an inflammatory disease or delaying the onset thereof by administration of the pharmaceutical composition according to the present invention.

The term "treatment" used herein refers to all actions involved in alleviating or beneficially changing symptoms of an inflammatory disease by administration of the pharmaceutical composition according to the present invention.

In the present invention, the inflammatory disease is a disease caused by the overexpression of BLT2, and may be one or more selected from asthma, atherosclerosis, cancer, pruritus, rheumatoid arthritis and inflammatory enteropathy, but the present invention is not limited thereto. Other than the diseases presented in the specification, all BLT2-associated inflammatory diseases known in the art are included as inflammatory diseases which can be prevented or treated with a compound having the structure of Formula 1 of the present invention. In a particular example, the cancer may be any cancer caused by the overexpression of BLT2 or Ras, which is a tumor gene. The cancer may be, but is not limited to, selected from the group consisting of kidney cancer, prostatic cancer, pancreatic cancer, breast cancer, brain tumors, skin cancer and liver cancer.

In the present invention, BLT2, as one among the G protein-coupled receptor (GPCR) family, is a receptor having low affinity to $LTB_4$, and therefore the composition of the present invention inhibits cell growth caused by BLT2 to prevent or treat an inflammatory disease. More specifically, $LTB_4$-induced chemotactic motility may be inhibited by inhibiting the generation of ROS induced by BLT2 activity.

The term "inhibition" used herein refers to inhibition of a certain step among gene transcription, mRNA processing, translation, translocation and maturation, or inhibition of binding between proteins, activation of a protein or signal transmission therethrough.

The pharmaceutical composition of the present invention may include a pharmaceutically acceptable carrier in addition to an active ingredient. Here, the pharmaceutically acceptable carrier is conventionally used in formulation, and includes, but is not limited to, lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil. In addition, other than the components, a lubricant, a wetting agent, a sweetening agent, a flavoring agent, an emulsifier, a suspending agent or a preservative may be further included.

The pharmaceutical composition of the present invention may be administered orally or parenterally (e.g., intravenously, subcutaneously, intraperitoneally or locally) depending on a desired method, and a dose of the pharmaceutical composition may vary depending on the condition and body weight of a patient, the severity of a disease, a drug type, an administration route and time, and may be suitably selected by one of ordinary skill in the art.

The pharmaceutical composition of the present invention is administered at a pharmaceutically effective amount. The "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present invention may be administered separately or in combination with other therapeutic agents, and may be sequentially or simultaneously administered with a conventional therapeutic agent, or administered in a single or multiple dose(s). In consideration of all the above-mentioned parameters, it is important to achieve the maximum effect with the minimum dose without a side effect, and such a dose may be easily determined by one of ordinary skill in the art.

Specifically, the effective amount of the pharmaceutical composition of the present invention may be dependent on a patient's age, sex, condition and body weight, an absorption rate of the active ingredient in the body, an inactivation rate, an excretion rate, a type of disease, or a drug used in combination, and may be generally administered at 0.001 to 150 mg, and preferably 0.01 to 100 mg per kg of body weight daily or every other day, or divided into one or three daily administrations. However, the effective amount may vary depending on an administration route, the severity of obesity, sex, body weight or age, and therefore, the scope of the present invention is not limited by the dose in any way.

In addition, the present invention provides a method for treating an inflammatory disease, which includes administering the pharmaceutical composition to a subject. The term "subject" refers to a target disease to be treated, and more specifically, a mammal such as a human, or a non-human primate, a mouse, a rat, a dog, a cat, a horse and a cow.

Hereinafter, to help in understanding the present invention, exemplary embodiments will be disclosed. However, the following examples are merely provided to more easily understand the present invention, and the scope of the present invention is not limited to the examples.

EXAMPLES

Example 1. Preparation of tert-butyl 4-(4-(3-(N-phenylpentanamido)prop-1-ynyl)benzoyl)piperazine-1-carboxylate (LMT-693)

Step 1: Preparation of N-phenylpentaneamide

Aniline (0.98 ml, 10.74 mmol) was dissolved in dichloromethane (20 ml), and then cooled on ice. Triethylamine (3.00 ml, 21.48 mmol) was added to the mixture, and then stirred for 5 minutes. Valeroyl chloride (2.60 ml, 21.48 mmol) was added at the same temperature, the ice was removed, and the mixture was stirred at room temperature for 2 hours. The reaction solution was concentrated under reduced pressure, and the residue obtained thereby was diluted with dichloromethane and washed with water and brine. An organic solvent layer was collected, dehydrated with anhydrous magnesium sulfate ($MgSO_4$), filtered, and then concentrated under reduced pressure. The concentrate was purified by silica gel column chromatography (Hex:EA=10:1), thereby obtaining N-phenylpentaneamide (1.88 g, 99% yield).

Step 2: Preparation of tert-butyl 4-(4-bromobenzoyl)piperazine-1-carboxylate 4-bromobenzoic acid (901 mg, 4.48 mmol) and tert-butyl piperazine-1-carboxylate (1.00 g, 5.37 mmol) were diluted in N,N-dimethylformamide (DMF; 15 ml), and stirred for 5 minutes. 1-[bis(dimethylamino)methylene]-1H-1,2,3-triazolo [4,5-b]pyridinium 3-oxid hexafluorophosphate (HATU; 2.04 g, 5.37 mmol) and N,N-diisopropylethylamine (DIPEA; 2.34 ml, 13.44 mmol) were added to the mixture, and stirred at room temperature for 15 hours. The reaction solution was concentrated under reduced pressure, and the residue obtained thereby was diluted with ethyl acetate and washed with water and brine. An organic solvent layer was collected, dehydrated with anhydrous magnesium sulfate ($MgSO_4$), filtered, and then concentrated under reduced pressure. The concentrate was purified by silica gel column chromatography (Hex:EA=2:1), thereby obtaining tert-butyl 4-(4-bromobenzoyl)piperazine-1-carboxylate (1.56 g, 94% yield).

Step 3: Preparation of tert-butyl 4-(4-(3-hydroxyprop-1-ynyl)benzoyl)piperazine-1-carboxylate The tert-butyl 4-(4-bromobenzoyl)piperazine-1-carboxylate (1.00 g, 2.71 mmol) obtained in Step 2 and propargyl alcohol (0.32 ml, 5.42 mmol) were dissolved in triethylamine (12 ml), and stirred for 5 minutes. Bis(triphenylphosphine)palladium (II) dichloride (190 mg, 0.271 mmol) and copper iodide (I) (52 mg, 0.271 mmol) were added to the mixture, heated at 60° C., and refluxed to be stirred for 17 hours. The reaction mixture was cooled at room temperature, concentrated under reduced pressure, and the residue obtained thereby was diluted with ethyl acetate and washed with water and brine. An organic solvent layer was collected, dehydrated with anhydrous magnesium sulfate ($MgSO_4$), filtered, and then concentrated under reduced pressure. The concentrate was purified by silica gel column chromatography (Hex:EA=2:1), thereby obtaining tert-butyl 4-(4-(3-hydroxyprop-1-ynyl)benzoyl)piperazine-1-carboxylate (850 mg, 91% yield).

Step 4: Preparation of tert-butyl 4-(4-(3-(methylsulfonyloxy)prop-1-ynyl)benzoyl)piperazine-1-carboxylate The tert-butyl 4-(4-(3-hydroxyprop-1-ynyl)benzoyl)piperazine-1-carboxylate (600 mg, 1.74 mmol) obtained in Step 3 was dissolved in dichloromethane (8 ml), and cooled on ice. Triethylamine (0.36 ml, 2.61 mmol) was added to the mixture, and stirred for 5 minutes. Methanesulfonyl chloride (0.15 ml, 1.92 mmol) was added at the same temperature, the ice was removed, and the mixture was stirred at room temperature for 30 minutes. The reaction solution was concentrated under reduced pressure, and the residue obtained thereby was diluted with dichloromethane and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=2:1), thereby obtaining tert-butyl 4-(4-(3-(methylsulfonyloxy)prop-1-ynyl)benzoyl)piperazine-1-carboxylate (662 mg, 90% yield).

Step 5: Preparation of tert-butyl 4-(4-(3-(N-phenylpentaneamido)prop-1-ynyl)benzoyl)piperazine-1-carboxylate The N-phenylpentaneamide (185 mg, 1.04 mmol) obtained in Step 1 and sodium hydride (NaH; 75 mg, 3.12 mmol) were cooled on ice, and then tetrahydrofuran (THF; 8 ml) was added, followed by stirring for 30 minutes. The tert-butyl 4-(4-(3-(methylsulfonyloxy)prop-1-ynyl)benzoyl) piperazine-1-carboxylate (662 mg, 1.57 mmol) obtained in Step 4 was added to the mixture, the ice was removed, and the mixture was stirred at room temperature for 17 hours. The reaction solution was concentrated under reduced pressure, and the residue obtained thereby was diluted with dichloromethane and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=4:1), thereby obtaining a final product, tert-butyl 4-(4-(3-(N-phenylpentaneamido)prop-1-ynyl)benzoyl)piperazine-1-carboxylate (382 mg, 73% yield).

$^1$H NMR (CDCl$_3$, 500 MHz) δ 7.40-7.20 (9H, m), 4.65 (2H, s), 3.62-3.32 (8H, br), 2.02-1.97 (2H, t), 1.52-1.48 (2H, m), 1.40 (9H, s), 1.19-1.12 (2H, m), 0.76-0.72 (3H, t).

Example 2. Preparation of N-phenyl-N-(3-(4-(piperazine-1-carbonyl)phenyl)prop-2-ynyl)pentanamide (LMT-694)

The tert-butyl 4-(4-(3-(N-phenylpentaneamido)prop-1-ynyl)benzoyl)piperazine-1-carboxylate (754 mg, 1.50 mmol) obtained in Example 1 was dissolved in acetonitrile (15 ml), and stirred at room temperature for 5 minutes. Dioxane-mixed hydrochloride (4N; 3.73 ml) was added to the mixture, and stirred at the same temperature for 1.5 hours. The reaction solution was concentrated under reduced pressure, and a residue obtained thereby was purified by silica gel column chromatography (CH$_2$Cl$_2$:MeOH=50:1), thereby obtaining a final product, N-phenyl-N-(3-(4-(piperazine-1-carbonyl)phenyl)prop-2-ynyl)pentaneamide (363 mg, 60% yield).

$^1$H NMR (CDCl$_3$, 500 MHz) δ 7.48-7.30 (9H, m), 4.73 (2H, s), 3.73-3.39 (4H, br), 2.97-2.86 (4H, br), 2.09-2.06 (2H, t), 1.60-1.54 (2H, m), 1.25-1.19 (2H, m), 0.83-0.80 (3H, t).

Example 3. Preparation of N-(3-(4-(4-methylpiperazine-1-carbonyl)phenyl)prop-2-ynyl)-N-phenylpentanamide (LMT-692)

The N-phenyl-N-(3-(4-(piperazine-1-carbonyl)phenyl) prop-2-ynyl)pentaneamide (33.3 mg, 0.072 mmol) obtained in Example 2 and potassium hydroxide (KOH; 9.09 mg, 0.108 mmol) were dissolved in N,N-dimethylformamide (DMF; 1 ml), and stirred at room temperature for 5 minutes. Iodomethane (9 μl, 0.144 mmol) was added to the mixture, and stirred at the same temperature for 17 hours. The reaction solution was concentrated under reduced pressure, and a residue obtained thereby was diluted with dichloromethane and washed with water and brine. An organic solvent layer was collected, dehydrated with anhydrous magnesium sulfate (MgSO$_4$), filtered, and then concentrated under reduced pressure. The concentrate was purified by silica gel column chromatography (CH$_2$Cl$_2$:MeOH=20:1), thereby obtaining a final product, N-(3-(4-(4-methylpiperazine-1-carbonyl)phenyl)prop-2-ynyl)-N-phenylpentaneamide (6 mg, 20% yield).

$^1$H NMR (CDCl$_3$, 400 MHz) δ 7.40-7.21 (9H, m), 4.65 (2H, s), 3.71-3.34 (4H, br), 2.41-2.25 (4H, br), 2.25 (3H, s), 2.02-1.99 (2H, t), 1.54-1.46 (2H, m), 1.18-1.12 (2H, m), 0.76-0.71 (3H, t).

Example 4. Preparation of N-(3-(4-(4-ethylpiperazine-1-carbonyl)phenyl)prop-2-ynyl)-N-phenylpentaneamide (LMT-695)

The N-phenyl-N-(3-(4-(piperazine-1-carbonyl)phenyl) prop-2-ynyl)pentaneamide (24.8 mg, 0.061 mmol) obtained in Example 3 and potassium hydroxide (8.62 mg, 0.154 mmol) were dissolved in N,N-dimethylformamide (DMF; 1 ml), and stirred at room temperature for 5 minutes. Iodoethane (20 μl, 0.246 mmol) was added to the mixture, and stirred at the same temperature for 17 hours. The reaction solution was concentrated under reduced pressure, and a residue obtained thereby was diluted with dichloromethane and washed with water and brine. An organic solvent layer was collected, dehydrated with anhydrous magnesium sulfate (MgSO$_4$), filtered, and then concentrated under reduced pressure. The concentrate was purified by silica gel column chromatography (CH$_2$Cl$_2$:MeOH=20:1), thereby obtaining a final product, N-(3-(4-(4-ethylpiperazine-1-carbonyl)phenyl)prop-2-ynyl)-N-phenylpentaneamide (17.9 mg, 68% yield).

$^1$H NMR (CDCl$_3$, 400 MHz) δ 7.40-7.20 (9H, m), 4.65 (2H, s), 3.73-3.35 (4H, br), 2.44-2.31 (6H, m), 2.03-1.99 (2H, t), 1.54-1.46 (2H, m), 1.20-1.13 (2H, m), 1.05-1.01 (3H, t), 0.78-0.73 (3H, t).

Example 5. Preparation of N-(3-(4-(4-isopropylpiperazine-1-carbonyl)phenyl)prop-2-ynyl)-N-phenylpentaneamide (LMT-696)

The N-phenyl-N-(3-(4-(piperazine-1-carbonyl)phenyl) prop-2-ynyl)pentaneamide (106 mg, 0.263 mmol) obtained in Example 2 and sodium bicarbonate (27 mg, 0.316 mmol) were cooled on ice, and then N,N-dimethylformamide (DMF; 2 ml) was added, followed by stirring for 1 hour. 2-iodopropane (30 μl, 0.316 mmol) was added to the mixture, the ice was removed, and then the mixture was heated at 60° C., refluxed and stirred for 24 hours. The reaction solution was cooled at room temperature and concentrated under reduced pressure, and a residue obtained thereby was diluted with ethylacetate and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA: MeOH:TEA=12:12:1:0.1), thereby obtaining a final product, N-(3-(4-(4-isopropylpiperazine-1-carbonyl)phenyl) prop-2-ynyl)-N-phenylpentaneamide (66.8 mg, 57% yield).

$^1$H NMR (CDCl$_3$, 500 MHz) δ 7.47-7.30 (9H, m), 4.73 (2H, s), 3.78-3.40 (4H, br), 2.75-2.72 (1H, m), 2.59-2.44

(4H, br), 2.09-2.06 (2H, t), 1.59-1.56 (2H, m), 1.25-1.20 (2H, m), 1.06-1.04 (6H, d), 0.83-0.80 (3H, t).

Example 6. Preparation of N-(3-(4-(4-(2-hydroxyethyl)piperazine-1-carbonyl)phenyl)prop-2-ynyl)-N-phenylpentaneamide (LMT-827)

The N-phenyl-N-(3-(4-(piperazine-1-carbonyl)phenyl)prop-2-ynyl)pentaneamide (56 mg, 0.139 mmol) obtained in Example 2 and potassium carbonate (77 mg, 0.556 mmol) were dissolved in acetonitrile (3 ml), and stirred at room temperature for 5 minutes. 2-bromoethanol (99 µl, 1.39 mmol) was added to the mixture, the ice was removed, and then the mixture was heated at 60° C., refluxed and stirred for 17 hours. An organic solvent layer was collected, dehydrated with anhydrous magnesium sulfate ($MgSO_4$), filtered, and then concentrated under reduced pressure. The concentrate was purified by silica gel column chromatography ($CH_2Cl_2$:MeOH=50:1), thereby obtaining a final product, N-(3-(4-(4-(2-hydroxyethyl)piperazine-1-carbonyl)phenyl)prop-2-ynyl)-N-phenylpentaneamide (52 mg, 84% yield).

$^1$H NMR ($CDCl_3$, 500 MHz) δ 7.48-7.30 (9H, m), 4.73 (2H, s), 3.79 (2H, br), 3.66-3.64 (2H, t), 3.43 (2H, br), 2.60-2.46 (7H, br), 2.10-2.07 (2H, t), 1.59-1.56 (2H, m), 1.25-1.22 (2H, m), 0.83-0.80 (3H, t).

Example 7. Preparation of N-(3-(4-(4-(cyclopropylmethyl)piperazine-1-carbonyl)phenyl)prop-2-ynyl)-N-phenylpentaneamide (LMT-828)

The N-phenyl-N-(3-(4-(piperazine-1-carbonyl)phenyl)prop-2-ynyl)pentaneamide (50 mg, 0.124 mmol) obtained in Example 2 and potassium carbonate (51 mg, 0.372 mmol) were dissolved in N,N-dimethylformamide (DMF; 2 ml), and stirred at room temperature for 5 minutes. Cyclopropylmethyl bromide (15 µl, 0.145 mmol) was added to the mixture, heated at 80° C., refluxed and stirred for 4 hours. An organic solvent layer was collected, dehydrated with anhydrous magnesium sulfate ($MgSO_4$), filtered, and then concentrated under reduced pressure. The concentrate was purified by silica gel column chromatography ($CH_2Cl_2$:MeOH=50:1), thereby obtaining a final product, N-(3-(4-(4-(cyclopropylmethyl)piperazine-1-carbonyl)phenyl)prop-2-ynyl)-N-phenylpentaneamide (16 mg, 28% yield).

$^1$H NMR ($CDCl_3$, 500 MHz) δ 7.48-7.28 (9H, m), 4.73 (2H, s), 3.82-3.45 (4H, br), 2.63-2.49 (4H, br), 2.32-2.31 (2H, d), 2.09-2.06 (2H, t), 1.60-1.56 (2H, m), 1.25-1.20 (3H, m), 0.83-0.80 (3H, t), 0.55-0.53 (2H, m), 0.12-0.11 (2H, m).

Example 8. Preparation of N-(3-(4-(4-cyclohexylpiperazine-1-carbonyl)phenyl)prop-2-ynyl)-N-phenylpentaneamide (LMT-830)

A final product, N-(3-(4-(4-cyclohexylpiperazine-1-carbonyl)phenyl)prop-2-ynyl)-N-phenylpentaneamide, was obtained (20 mg, 33% yield) by the same method described in Example 7 using the N-phenyl-N-(3-(4-(piperazine-1-carbonyl)phenyl)prop-2-ynyl)pentaneamide (50 mg, 0.124 mmol) obtained in Example 2 and iodocyclohexane (19 µl, 0.145 mmol).

$^1$H NMR ($CDCl_3$, 500 MHz) δ 7.48-7.31 (9H, m), 4.73 (2H, s), 3.77-3.39 (4H, br), 2.63-2.49 (4H, br), 2.31-2.28 (1H, m), 2.09-2.06 (2H, m), 1.91-1.79 (4H, m), 1.65-1.54 (3H, m), 1.28-1.16 (6H, m), 1.13-1.08 (1H, m), 0.83-0.80 (3H, t).

Example 9. Preparation of N-(3-(4-(4-(cyclohexylmethyl)piperazine-1-carbonyl)phenyl)prop-2-ynyl)-N-phenylpentanamide (LMT-831)

A final product, N-(3-(4-(4-(cyclohexylmethyl)piperazine-1-carbonyl)phenyl)prop-2-ynyl)-N-phenylpentaneamide, was obtained (35 mg, 56% yield) by the same method as described in Example 7 using the N-phenyl-N-(3-(4-(piperazine-1-carbonyl)phenyl)prop-2-ynyl)pentaneamide (50 mg, 0.124 mmol) obtained in Example 2 and bromomethylcyclohexane (20 µl, 0.145 mmol).

$^1$H NMR ($CDCl_3$, 500 MHz) δ 7.48-7.28 (9H, m), 4.73 (2H, s), 3.76-3.38 (4H, br), 2.45-2.31 (4H, br), 2.15-2.13 (2H, m), 2.09-2.06 (2H, m), 1.77-1.66 (5H, m), 1.59-1.56 (2H, m), 1.47-1.45 (1H, m), 1.25-1.17 (5H, m), 0.90-0.80 (5H, t).

Example 10. Preparation of N-(3-(4-(4-isobutylpiperazine-1-carbonyl)phenyl)prop-2-ynyl)-N-phenylpentanamide (LMT-832)

A final product, N-(3-(4-(4-isobutylpiperazine-1-carbonyl)phenyl)prop-2-ynyl)-N-phenylpentaneamide, was obtained (34 mg, 60% yield) by the method as described in Example 7 using the N-phenyl-N-(3-(4-(piperazine-1-carbonyl)phenyl)prop-2-ynyl)pentaneamide (50 mg, 0.124 mmol) obtained in Example 2 and 1-iodo-2-methylpropane (17 µl, 0.145 mmol).

$^1$H NMR ($CDCl_3$, 500 MHz) δ 7.47-7.28 (9H, m), 4.73 (2H, s), 3.76-3.39 (4H, br), 2.46-2.32 (4H, br), 2.11-2.07 (4H, m), 1.79-1.76 (1H, m), 1.59-1.56 (2H, m), 1.25-1.20 (2H, m), 0.91-0.89 (6H, d), 0.83-0.80 (3H, t).

Example 11. Preparation of N-phenyl-N-(3-(4-(4-(prop-2-ynyl)piperazine-1-carbonyl)phenyl)prop-2-ynyl)pentanamide (LMT-833)

The N-phenyl-N-(3-(4-(piperazine-1-carbonyl)phenyl)prop-2-ynyl)pentaneamide (50 mg, 0.124 mmol) obtained in Example 2 and potassium carbonate (51 mg, 0.372 mmol) were dissolved in N,N-dimethylformamide (DMF; 2 ml), and stirred at room temperature for 5 minutes. Propargyl bromide (12 µl, 0.145 mmol) was added to the mixture, and stirred at room temperature for 17 hours. The reaction solution was filtered to remove a solid and concentrated under reduced pressure, and the concentrate was purified by silica gel column chromatography ($CH_2Cl_2$:MeOH=100:1), thereby obtaining a final product, N-phenyl-N-(3-(4-(4-(prop-2-ynyl)piperazine-1-carbonyl)phenyl)prop-2-ynyl)pentaneamide (28 mg, 51% yield).

$^1$H NMR ($CDCl_3$, 500 MHz) δ 7.48-7.28 (9H, m), 4.73 (2H, s), 3.82-3.44 (4H, br), 3.36 (2H, s), 2.65-2.51 (4H, br), 2.30 (1H, s), 2.10-2.07 (2H, m), 1.60-1.54 (2H, m), 1.26-1.19 (2H, m), 0.83-0.80 (3H, t).

Example 12. Preparation of N-(3-(4-(4-cyanopiperazine-1-carbonyl)phenyl)prop-2-ynyl)-N-phenylpentanamide (LMT-829)

The N-phenyl-N-(3-(4-(piperazine-1-carbonyl)phenyl)prop-2-ynyl)pentaneamide (50 mg, 0.124 mmol) obtained in Example 2 and trimethylsilyl cyanide (49 µl, 0.372 mmol) were dissolved in acetonitrile (2 ml), and stirred at room temperature for 5 minutes. Sodium hypochloride (43 al, 0.620 mmol) was added to the mixture, heated at 80° C., refluxed, and stirred for 12 hours. The reaction solution was cooled at room temperature, filtered to remove a solid, and concentrated under reduced pressure. The obtained residue was diluted with ethyl acetate, and washed with water and brine. An organic solvent layer was collected, dehydrated with anhydrous magnesium sulfate (MgSO$_4$), filtered, and then concentrated under reduced pressure. The concentrate was purified by silica gel column chromatography (CH$_2$Cl$_2$: MeOH=200:1), thereby obtaining a final product, N-(3-(4-(4-cyanopiperazine-1-carbonyl)phenyl)prop-2-ynyl)-N-phenylpentanamide (11 mg, 21% yield).

$^1$H NMR (CDCl$_3$, 500 MHz) δ 7.48-7.30 (9H, m), 4.73 (2H, s), 3.81-3.26 (8H, br), 2.09-2.06 (2H, t), 1.60-1.54 (2H, m), 1.25-1.19 (2H, m), 0.83-0.80 (3H, t).

Example 13. Preparation of tert-butyl 4-(4-(3-(N-(3-fluorophenyl)pentanamido)prop-1-ynyl)benzoyl)piperazine-1-carboxylate (LMT-884)

Step 1: Preparation of N-(3-fluorophenyl)pentanamide

N-(3-fluorophenyl)pentaneamide was obtained (1.74 g, 99% yield) using 3-fluoroaniline (0.87 ml, 9.00 mmol) and valeroyl chloride (2.18 ml, 18.00 mmol).

Step 2: Preparation of tert-butyl 4-(4-(3-(N-(3-fluorophenyl)pentanamido)prop-1-ynyl)benzoyl)piperazine-1-carboxylate A final product, tert-butyl 4-(4-(3-(N-(3-fluorophenyl)pentaneamido)prop-1-ynyl)benzoyl)piperazine-1-carboxylate, was obtained (197 mg, 73% yield) by the same method as described in Step 5 of Example 1 using the N-(3-fluorophenyl)pentaneamide (101 mg, 0.519 mmol) obtained in Step 1 and the tert-butyl 4-(4-(3-(methylsulfonyloxy)prop-1-ynyl)benzoyl)piperazine-1-carboxylate (329 mg, 0.779 mmol) obtained in Step 4 of Example 1.

$^1$H NMR (CDCl$_3$, 400 MHz) δ 7.44-7.32 (5H, m), 7.12-7.06 (3H, m), 4.72 (2H, s), 3.73-3.38 (8H, br), 2.10-2.07 (2H, t), 1.59-1.57 (2H, m), 1.47 (9H, s), 1.23-1.20 (2H, m), 0.83-0.80 (3H, t).

Example 14. Preparation of N-(3-fluorophenyl)-N-(3-(4-(piperazine-1-carbonyl)phenyl)prop-2-ynyl)pentaneamide (LMT-885)

A final product, N-(3-fluorophenyl)-N-(3-(4-(piperazine-1-carbonyl)phenyl)prop-2-ynyl)pentaneamide, was obtained (94 mg, 58% yield) by the same method as described in Example 12 using the tert-butyl 4-(4-(3-(N-(3-fluorophenyl)pentaneamido)prop-1-ynyl)benzoyl)piperazine-1-carboxylate (200 mg, 0.383 mmol) obtained in Example 13.

$^1$H NMR (CDCl$_3$, 400 MHz) δ 7.45-7.32 (5H, m), 7.15-7.07 (3H, m), 4.72 (2H, s), 3.75-3.37 (4H, br), 2.94-2.80 (4H, br), 2.10-2.07 (2H, t), 1.89 (1H, br), 1.60-1.57 (2H, m), 1.25-1.24 (2H, m), 0.84-0.82 (3H, t).

Example 15. Preparation of N-(3-fluorophenyl)-N-(3-(4-(4-isopropylpiperazine-1-carbonyl)phenyl)prop-2-ynyl)pentaneamide (LMT-886)

A final product, N-(3-fluorophenyl)-N-(3-(4-(4-isopropylpiperazine-1-carbonyl)phenyl)prop-2-ynyl)pentaneamide, was obtained (20 mg, 40% yield) using the N-(3-fluorophenyl)-N-(3-(4-(piperazine-1-carbonyl)phenyl)prop-2-ynyl)pentaneamide (46 mg, 0.109 mmol) obtained in Example 14 and 2-iodopropane (0.375 ml, 3.77 mmol).

$^1$H NMR (CDCl$_3$, 400 MHz) δ 7.44-7.32 (5H, m), 7.15-7.06 (3H, m), 4.72 (2H, s), 3.78-3.41 (4H, br), 2.75-2.72 (1H, m), 2.59-2.45 (4H, br), 2.11-2.09 (2H, t), 1.60-1.57 (2H, m), 1.25-1.22 (2H, m), 1.06-1.05 (6H, d), 0.85-0.82 (3H, t).

Example 16. Preparation of tert-butyl 4-(4-(3-(N-(4-fluorophenyl)pentaneamido)prop-1-ynyl)benzoyl)piperazine-1-carboxylate (LMT-839)

Step 1: Preparation of N-(4-fluorophenyl)pentaneamide

N-(4-fluorophenyl)pentaneamide was obtained (174 mg, 99% yield) by the same method as described in Step 1 of Example 1 using 4-fluoroaniline (85 µl, 0.90 mmol) and valeroyl chloride (0.22 ml, 1.80 mmol).

Step 2: Preparation of tert-butyl 4-(4-(3-(N-(4-fluorophenyl)pentanamido)prop-1-ynyl)benzoyl)piperazine-1-carboxylate A final product, tert-butyl 4-(4-(3-(N-(4-fluorophenyl)pentaneamido)prop-1-ynyl)benzoyl)piperazine-1-carboxylate, was obtained (2.28 g, 73% yield) by the same method as described in Step 5 of Example 1 using the N-(4-fluorophenyl)pentaneamide (1.17 g, 6.00 mmol) obtained in Step 1 and the tert-butyl 4-(4-(3-(methylsulfonyloxy)prop-1-ynyl)benzoyl)piperazine-1-carboxylate (3.80 g, 8.99 mmol) obtained in Step 4 of Example 1.

$^1$H NMR (CDCl$_3$, 400 MHz) δ 7.39-7.29 (6H, m), 7.17-7.14 (2H, m), 4.71 (2H, s), 3.73-3.38 (8H, br), 2.07-2.04 (2H, t), 1.60-1.54 (2H, m), 1.47 (9H, s), 1.25-1.19 (2H, m), 0.84-0.81 (3H, t).

Example 17. Preparation of N-(4-fluorophenyl)-N-(3-(4-(piperazine-1-carbonyl)phenyl)prop-2-ynyl)pentaneamide (LMT-840)

A final product, N-(4-fluorophenyl)-N-(3-(4-(piperazine-1-carbonyl)phenyl)prop-2-ynyl)pentaneamide, was obtained (1.06 g, 58% yield) by the same method as described in Example 12 using the tert-butyl 4-(4-(3-(N-(4-fluorophenyl)pentaneamido)prop-1-ynyl)benzoyl)piperazine-1-carboxylate (2.28 g, 4.37 mmol) obtained in Example 16.

$^1$H NMR (CDCl$_3$, 400 MHz) δ 7.38-7.30 (6H, m), 7.17-7.15 (2H, m), 4.71 (2H, s), 3.77-3.40 (4H, br), 2.96-2.79 (5H, br), 2.06-2.03 (2H, t), 1.57-1.54 (2H, m), 1.25-1.22 (2H, m), 0.84-0.82 (3H, t).

Example 18. Preparation of N-(4-fluorophenyl)-N-(3-(4-(4-isopropylpiperazine-1-carbonyl)phenyl)prop-2-ynyl)pentaneamide (LMT-841)

A final product, N-(4-fluorophenyl)-N-(3-(4-(4-isopropylpiperazine-1-carbonyl)phenyl)prop-2-ynyl)pentaneamide, was obtained (465 mg, 40% yield) by the same method as described in Example 15 using the N-(4-fluorophenyl)-N-(3-(4-(piperazine-1-carbonyl)phenyl)prop-2-ynyl)pentaneamide (1.06 g, 2.51 mmol) obtained in Example 17 and 2-iodopropane (0.375 ml, 3.77 mmol).

$^1$H NMR (CDCl$_3$, 400 MHz) δ 7.37-7.28 (6H, m), 7.17-7.13 (2H, m), 4.71 (2H, s), 3.78-3.40 (4H, br), 2.75-2.72 (1H, m), 2.59-2.45 (4H, br), 2.07-2.04 (2H, t), 1.58-1.55 (2H, m), 1.25-1.21 (2H, m), 1.06-1.04 (6H, d), 0.84-0.81 (3H, t).

Example 19. Preparation of N-(3-(4-(morpholine-4-carbonyl)phenyl)prop-2-ynyl)-N-phenylpentaneamide (LMT-682)

Step 1: (4-bromophenyl)(morpholino)methanone (4-bromophenyl)(morpholino)methanone was obtained (455 mg, yield 99%) by the same method as described in Step 2 of Example 1 using 4-bromobenzoic acid (340 mg, 1.70 mmol) and morpholine (0.18 ml, 2.04 mmol).

Step 2: Preparation of (4-(3-hydroxyprop-1-ynyl)phenyl)(morpholino)methanone (4-(3-hydroxyprop-1-ynyl)phenyl)(morpholino)methanone was obtained (371 mg, yield 90%) by the same method as described in Step 3 of Example 1 using the (4-bromophenyl)(morpholino)methanone (455 mg, 1.68 mmol) obtained in Step 1 and propargyl alcohol (0.196 ml, 3.36 mmol).

Step 3: Preparation of 3-(4-(morpholine-4-carbonyl)phenyl)prop-2-ynyl methanesulfonate 3-(4-(morpholine-4-carbonyl)phenyl)prop-2-ynyl methanesulfonate was obtained (391 mg, yield 80%) by the same method as described in Step 4 of Example 1 using the (4-(3-hydroxyprop-1-ynyl)phenyl)(morpholino)methanone (371 mg, 1.51 mmol) obtained in Step 2 and methanesulfonyl chloride (0.128 ml, 1.66 mmol).

Step 4: Preparation of N-(3-(4-(morpholine-4-carbonyl)phenyl)prop-2-ynyl)-N-phenylpentaneamide A final product, N-(3-(4-(morpholine-4-carbonyl)phenyl)prop-2-ynyl)-N-phenylpentaneamide, was obtained (371 mg, yield 90%) by the same method as described in Step 5 of Example 1 using the N-phenylpentaneamide (143 mg, 0.81 mmol) obtained in Step 1 of Example 1 and the 3-(4-(morpholine-4-carbonyl)phenyl)prop-2-ynyl methanesulfonate (391 mg, 1.21 mmol) obtained in Step 3.

$^1$H NMR (400 MHz, CDCl$_3$) δ 7.48-7.28 (m, 9H), 4.73 (s, 2H), 3.74-3.66 (br, 6H), 3.43 (br, 2H), 2.08 (m, 2H), 1.57 (m, 2H), 1.22 (m, 2H), 0.81 (t, 3H).

Example 20. Preparation of N-phenyl-N-(3-(4-(piperidine-1-carbonyl)phenyl)prop-2-ynyl)pentaneamide (LMT-683)

Step 1: Preparation of (4-bromophenyl)(piperidin-1-yl)methanone (4-bromophenyl)(piperidin-1-yl)methanone was obtained (458.2 mg, 100% yield) by the same method as described in Step 2 of Example 1 using 4-bromobenzoic acid (318 mg, 1.58 mmol) and piperidine (0.21 ml, 1.90 mmol).

Step 2: Preparation of (4-(3-hydroxyprop-1-ynyl)phenyl)(piperidin-1-yl)methanone (4-(3-hydroxyprop-1-ynyl)phenyl)(piperidin-1-yl)methanone was obtained (374 mg, yield 90%) by the same method as described in Step 3 of Example 1 using the (4-bromophenyl)(piperidine-1-yl)methanone (458.2 mg, 1.71 mmol) obtained in Step 1 and propargyl alcohol (0.199 ml, 3.42 mmol).

Step 3: Preparation of 3-(4-(piperidine-1-carbonyl)phenyl)prop-2-ynyl methanesulfonate 3-(4-(piperidine-1-carbonyl)phenyl)prop-2-ynyl methanesulfonate was obtained (396 mg, yield 80%) by the same method as described in Step 4 of Example 1 using the (4-(3-hydroxyprop-1-ynyl)phenyl)pyridine-1-yl)methanone (374 mg, 1.54 mmol) obtained in Step 2 and methanesulfonyl chloride (0.131 ml, 1.69 mmol).

Step 4: Preparation of N-phenyl-N-(3-(4-(piperidine-1-carbonyl)phenyl)prop-2-ynyl)pentaneamide A final product, N-phenyl-N-(3-(4-(piperidine-1-carbonyl)phenyl)prop-2-ynyl)pentaneamide, was obtained (50 mg, 15% yield) by the same method as described in Step 5 of Example 1 using the N-phenylpentaneamide (146 mg, 0.82 mmol) obtained in Step 1 of Example 1 and the 3-(4-(pyridine-1-carbonyl)phenyl)prop-2-ynyl methanesulfonate (396 mg, 1.23 mmol) obtained in Step 3.

$^1$H NMR (CDCl$_3$, 400 MHz) δ 7.40-7.13 (9H, m), 4.65 (2H, s, CH$_2$), 3.62-3.24 (4H, br), 2.02-1.99 (2H, t), 1.60 (4H, br), 1.52-1.46 (2H, m), 1.44 (2H, br), 1.20-1.08 (2H, m), 0.78-0.73 (3H, t).

Example 21. Preparation of N,N-diethyl-4-(3-(N-phenylpentaneamido)prop-1-ynyl)benzamide (LMT-883)

Step 1: Preparation of 4-bromo-N,N-diethylbenzamide 4-bromo-N,N-diethylbenzamide was obtained (700 mg, 69% yield) by the same method as described in Step 2 of Example 1 using 4-bromobenzoic acid (800 mg, 3.98 mmol) and diethylamine (0.49 ml, 4.78 mmol).

Step 2: Preparation of N,N-diethyl-4-(3-hydroxyprop-1-ynyl)benzamide

N,N-diethyl-4-(3-hydroxyprop-1-ynyl)benzamide was obtained (425 mg, 67% yield) by the same method as described in Step 3 of Example 1 using the 4-bromo-N,N-diethylbenzamide (700 mg, 2.73 mmol) obtained in Step 1 and propargyl alcohol (0.32 ml, 5.47 mmol).

Step 3: Preparation of 3-(4-(diethylcarbamoyl)phenyl)prop-2-ynyl methanesulfonate 3-(4-(diethylcarbamoyl)phenyl)prop-2-ynyl methanesulfonate was obtained (483 mg, 85% yield) by the same method as described in Step 4 of Example 1 using the N,N-diethyl-4-(3-hydroxyprop-1-ynyl)benzamide (425 mg, 1.84 mmol) obtained in Step 2 and methanesulfonyl chloride (0.16 ml, 2.02 mmol).

Step 4: Preparation of N,N-diethyl-4-(3-(N-phenylpentanamido)prop-1-ynyl)benzamide A final product, N,N-diethyl-4-(3-(N-phenylpentaneamido)prop-1-ynyl)benzamide, was obtained (81 mg, 39% yield) by the same method as described in Step 5 of Example 1 using the N-phenylpentaneamide (94 mg, 0.530 mmol) obtained in Step 1 of Example 1 and the 3-(4-

(diethylcarbamoyl)phenyl)prop-2-ynyl methanesulfonate (246 mg, 0.795 mmol) obtained in Step 3.

$^1$H NMR (CDCl$_3$, 400 MHz) δ 7.48-7.30 (9H, m), 4.73 (2H, s), 3.53-3.23 (4H, br), 2.10-2.07 (2H, t), 1.59-1.57 (2H, m), 1.23-1.10 (8H, m), 0.83-0.80 (3H, t).

Example 22. Preparation of N-phenyl-N-(3-(3-(piperazine-1-carbonyl)phenyl)prop-2-ynyl)pentaneamide (LMT-837)

Step 1: Preparation of tert-butyl 4-(3-bromobenzoyl)piperazine-1-carboxylate

Tert-butyl 4-(3-bromobenzoyl)piperazine-1-carboxylate was obtained (2.75 g, 99% yield) by the same method described in Step 2 of Example 1 using 3-bromobenzoic acid (1.50 g, 7.46 mmol) and tert-butyl piperazine-1-carboxylate (1.67 g, 8.95 mmol).

Step 2: Preparation of tert-butyl 4-(3-(3-hydroxyprop-1-ynyl)benzoyl)piperazine-1-carboxylate Tert-butyl 4-(3-(3-hydroxyprop-1-ynyl)benzoyl)piperazine-1-carboxylate was obtained (2.32 g, 90% yield) by the same method as described in Step 3 of Example 1 using the tert-butyl 4-(3-bromobenzoyl)piperazine-1-carboxylate (2.75 g, 7.45 mmol) obtained in Step 1 and propargyl alcohol (0.87 ml, 14.89 mmol).

Step 3: Preparation of tert-butyl 4-(3-(3-(methylsulfonyloxy)prop-1-ynyl)benzoyl)piperazine-1-carboxylate Tert-butyl 4-(3-(3-(methylsulfonyloxy)prop-1-ynyl)benzoyl)piperazine-1-carboxylate was obtained (1.78 g, 63% yield) by the same method as described in Step 4 of Example 1 using the tert-butyl 4-(3-(3-hydroxyprop-1-ynyl)benzoyl)piperazine-1-carboxylate (2.32 g, 6.75 mmol) obtained in Step 2 and methanesulfonyl chloride (0.58 ml, 7.42 mmol).

Step 4: Preparation of tert-butyl 4-(3-(3-(N-phenylpentaneamido)prop-1-ynyl)benzoyl)piperazine-1-carboxylate A final product tert-butyl 4-(3-(3-(N-phenylpentaneamido)prop-1-ynyl)benzoyl)piperazine-1-carboxylate was obtained (323 mg, 70% yield) by the same method as described in Step 5 of Example 1 using the N-phenylpentaneamide (275 mg, 1.55 mmol) obtained in Step 1 of Example 1 and the tert-butyl 4-(3-(3-(methylsulfonyloxy)prop-1-ynyl)benzoyl)piperazine-1-carboxylate (982 mg, 2.33 mmol) obtained in Step 3.

Step 5: Preparation of N-phenyl-N-(3-(3-(piperazine-1-carbonyl)phenyl)prop-2-ynyl)pentaneamide (LMT-837)

A final product, N-phenyl-N-(3-(3-(piperazine-1-carbonyl)phenyl)prop-2-ynyl)pentaneamide, was obtained (152 mg, 58% yield) by the same method as described in Example 2 using the tert-butyl 4-(3-(3-(N-phenylpentaneamido)prop-1-ynyl)benzoyl)piperazine-1-carboxylate (323 mg, 0.62 mmol) obtained in Step 4.

$^1$H NMR (CDCl$_3$, 400 MHz) δ 7.45-7.26 (9H, m), 4.69 (2H, s), 3.75-3.36 (4H, br), 2.94-2.80 (4H, br), 2.59 (1H, br), 2.07-2.04 (2H, t), 1.56-1.53 (2H, m), 1.22-1.18 (2H, m), 0.80-0.77 (3H, t).

Example 23. Preparation of N-(3-(3-(4-methylpiperazine-1-carbonyl)phenyl)prop-2-ynyl)-N-phenylpentaneamide (LMT-838)

The N-phenyl-N-(3-(3-(piperazine-1-carbonyl)phenyl)prop-2-ynyl)pentaneamide (50 mg, 0.124 mmol) obtained in Example 22 and formaldehyde (37% in H$_2$O; 1.5 ml) were dissolved in formic acid (2.0 ml), heated at 100° C., refluxed, and stirred for 4 hours. The reaction solution was concentrated under reduced pressure, and titrated by adding a sodium hydroxide aqueous solution (2.0 M). Afterward, the reaction product was diluted with dichloromethane, and washed with water and brine. An organic solvent layer was collected, dehydrated with anhydrous magnesium sulfate (MgSO$_4$), filtered, and then concentrated under reduced pressure. The concentrate was purified by silica gel column chromatography (CH$_2$Cl$_2$:MeOH=20:1), thereby obtaining N-(3-(3-(4-methylpiperazine-1-carbonyl)phenyl)prop-2-ynyl)-N-phenylpentaneamide (24 mg, 46% yield).

$^1$H NMR (CDCl$_3$, 400 MHz) δ 7.46-7.29 (9H, m), 4.70 (2H, s), 3.79-3.39 (4H, br), 2.48-2.32 (7H, br), 2.08-2.05 (2H, t), 1.57-1.54 (2H, m), 1.23-1.19 (2H, m), 0.81-0.78 (3H, t).

Example 24. Preparation of N-(3-(3-(4-isopropylpiperazine-1-carbonyl)phenyl)prop-2-ynyl)-N-phenylpentaneamide (LMT-842)

A final product, N-(3-(3-(4-isopropylpiperazine-1-carbonyl)phenyl)prop-2-ynyl)-N-phenylpentaneamide, was obtained (67 mg, 40% yield) by the same method as described in Example 5 using the N-phenyl-N-(3-(3-(piperazine-1-carbonyl)phenyl)prop-2-ynyl)pentaneamide (152 mg, 0.36 mmol) obtained in Example 22 and 2-iodopropane (90 μl, 0.90 mmol).

$^1$H NMR (CDCl$_3$, 400 MHz) δ 7.47-7.29 (9H, m), 4.71 (2H, s), 3.79-3.40 (4H, br), 2.78-2.75 (1H, m), 2.60-2.46 (4H, br), 2.09-2.06 (2H, t), 1.58-1.55 (2H, m), 1.24-1.20 (2H, m), 1.07-1.05 (6H, d), 0.82-0.79 (3H, t).

Example 25. Preparation of tert-butyl 4-(3-(3-(N-(4-fluorophenyl)pentaneamido)prop-1-ynyl)benzoyl)piperazine-1-carboxylate (LMT-887)

A final product, tert-butyl-4-(3-(3-(N-(4-fluorophenyl)pentaneamido)prop-1-ynyl)benzoyl)piperazine-1-carboxylate, was obtained (625 mg, 85% yield) by the same method as described in Step 5 of Example 1 using the N-(4-fluorophenyl)pentaneamide (275 mg, 1.41 mmol) obtained in Step 1 of Example 16 and the tert-butyl 4-(3-(3-(methylsulfonyloxy)prop-1-ynyl)benzoyl)piperazine-1-carboxylate (894 mg, 2.12 mmol) obtained in Step 3 of Example 22.

$^1$H NMR (CDCl$_3$, 400 MHz) δ 7.33-7.20 (6H, m), 7.09-7.06 (2H, m), 4.62 (2H, s), 3.66-3.31 (8H, br), 2.00-1.97 (2H, t), 1.52-1.49 (2H, m), 1.47 (9H, s), 1.18-1.13 (2H, m), 0.76-0.73 (3H, t).

Example 26. Preparation of N-(4-fluorophenyl)-N-(3-(3-(piperazine-1-carbonyl)phenyl)prop-2-ynyl)pentaneamide (LMT-888)

A final product, N-(4-fluorophenyl)-N-(3-(3-(piperazine-1-carbonyl)phenyl)prop-2-ynyl)pentaneamide, was obtained (356 mg, 58% yield) by the same method as described in Example 2 using the tert-butyl-4-(3-(3-(N-(4- fluorophenyl)pentaneamido)prop-1-ynyl)benzoyl)piperazine-1-carboxylate (762 mg, 1.46 mmol) obtained in Example 25.

$^1$H NMR (CDCl$_3$, 400 MHz) δ 7.39-7.29 (6H, m), 7.17-7.14 (2H, m), 4.70 (2H, s), 3.77-3.39 (4H, br), 2.98-2.85 (4H, br), 2.08-2.05 (2H, t), 1.60-1.54 (2H, m), 1.25-1.19 (2H, m), 0.84-0.81 (3H, t).

Example 27. Preparation of N-(4-fluorophenyl)-N-(3-(3-(4-isopropylpiperazine-1-carbonyl)phenyl)prop-2-ynyl)pentaneamide (LMT-889)

A final product, N-(4-fluorophenyl)-N-(3-(3-(4-isopropylpiperazine-1-carbonyl)phenyl)prop-2-ynyl)pentaneamide, was obtained (66 mg, 40% yield) by the same method as described in Example 5 using the N-(4-fluorophenyl)-N-(3-(3-(piperazine-1-carbonyl)phenyl)prop-2-ynyl)pentaneamide (150 mg, 0.356 mmol) obtained in Example 26 and 2-iodopropane (53 μl, 0.534 mmol).

$^1$H NMR (CDCl$_3$, 400 MHz) δ 7.37-7.29 (6H, m), 7.16-7.13 (2H, m), 4.70 (2H, s), 3.79-3.39 (4H, br), 2.75-2.73 (1H, m), 2.59-2.45 (4H, br), 2.07-2.04 (2H, t), 1.58-1.55 (2H, m), 1.25-1.21 (2H, m), 1.06-1.05 (6H, d), 0.84-0.81 (3H, t).

Example 28. Preparation of N-(3-(4-hydroxyphenyl)prop-2-ynyl)-N-phenylpentaneamide (LMT-890)

Step 1: Preparation of N-(prop-2-ynyl)aniline

Aniline (2.94 ml, 32.21 mmol) and potassium carbonate (4.90 g, 35.43 mmol) were dissolved in acetonitrile (40 ml), and stirred for 5 minutes. Propargyl bromide (3.05 ml, 35.43 mmol) was added to the mixture, and stirred at room temperature for 17 hours. The reaction solution was filtered to remove a solid, and concentrated under reduced pressure. The concentrate was purified by silica gel column chromatography (Hex), thereby obtaining N-(prop-2-ynyl)aniline (2.23 g, 53% yield).

Step 2: Preparation of N-phenyl-N-(prop-2-ynyl)pentaneamide

N-phenyl-N-(prop-2-ynyl)pentaneamide was obtained (1.29 g, 95% yield) by the same method as described in Step 1 of Example 1 using the N-(prop-2-ynyl)aniline (828 mg, 6.31 mmol) obtained in Step 1 and valeroyl chloride (1.53 ml, 12.62 mmol).

Step 3: Preparation of N-(3-(4-hydroxyphenyl)prop-2-ynyl)-N-phenylpentaneamide

The N-phenyl-N-(prop-2-ynyl)pentaneamide (550 mg, 2.55 mmol) obtained in Step 2 and 4-iodophenol (422 mg, 1.92 mmol) were dissolved in triethylamine (15 ml), and stirred for 5 minutes. Bis(triphenylphosphine)palladium (II) dichloride (89 mg, 0128 mmol) and copper iodide (I) (49 mg, 0.255 mmol) were added to the mixture, heated at 50° C., refluxed, and stirred for 5 hours. The reaction solution was cooled at room temperature and concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=10:1), thereby obtaining a final product, N-(3-(4-hydroxyphenyl)prop-2-ynyl)-N-phenylpentaneamide (590 mg, 75% yield).

$^1$H NMR (CDCl$_3$, 400 MHz) δ 8.15 (1H, br), 7.47-6.83 (9H, m), 4.66 (2H, s), 2.13-2.10 (2H, t), 1.60-1.54 (2H, m), 1.22-1.17 (2H, m), 0.80-0.77 (3H, t).

Example 29. Preparation of 2-(4-(3-(N-phenylpentaneamido)prop-1-ynyl)phenoxy)acetic acid (LMT-891)

Step 1: Preparation of ethyl (2-(4-(3-(N-phenylpentaneamido)prop-1-ynyl)phenoxy)acetate The N-(3-(4-hydroxyphenyl)prop-2-ynyl)-N-phenylpentaneamide (590 mg, 1.92 mmol) obtained in Example 28 and potassium carbonate (796 mg, 5.76 mmol) were dissolved in acetonitrile (15 ml), and stirred for 30 minutes. Ethyl bromoacetate (0.23 ml, 2.11 mmol) was added to the mixture, and stirred at room temperature for 17 hours. The reaction solution was filtered to remove a solid and concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=10:1), thereby obtaining ethyl 2-(4-(3-(N-phenylpentaneamido)prop-1-ynyl)phenoxy)acetate (530 mg, 70% yield).

Step 2: Preparation of 2-(4-(3-(N-phenylpentaneamido)prop-1-ynyl)phenoxy)acetic acid The ethyl 2-(4-(3-(N-phenylpentaneamido)prop-1-ynyl)phenoxy)acetate (530 mg, 1.35 mmol) obtained in Step 1 was dissolved in ethanol (15 ml), and stirred at room temperature for 5 minutes. 2N sodium hydroxide (NaOH; 0.50 ml) was added to the mixture, heated at 80° C., refluxed and stirred for 3 hours. The reaction solution was cooled at room temperature and concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified by silica gel column chromatography (CH$_2$Cl$_2$:MeOH=100:1), thereby obtaining a final product, 2-(4-(3-(N-phenylpentaneamido)prop-1-ynyl)phenoxy)acetic acid (246 mg, 50% yield).

$^1$H NMR (CDCl$_3$, 400 MHz) δ 7.47-6.78 (9H, m), 4.68 (2H, s), 4.58 (2H, s), 2.11-2.08 (2H, t), 1.58-1.53 (2H, m), 1.23-1.18 (2H, m), 0.81-0.78 (3H, t).

Example 30. Preparation of tert-butyl 4-(5-(3-(N-phenylpentanamido)prop-1-yn-1-yl)picolinoyl)piperazine-1-carboxylate (LMT-834)

A final product, tert-butyl 4-(5-(3-(N-phenylpentaneamido)prop-1-yn-1-yl)picolinoyl)piperazine-1-carboxylate, was obtained (36 mg, 35% yield) using the same method as described in Step 3 of Example 28 using the N-phenyl-N-(prop-2-ynyl)pentaneamide obtained in Step 2 of Example 28 and tert-butyl 4-(5-bromopicolinoyl)piperazine-1-carboxylate (86 mg, 0.4 mmol).

$^1$H NMR (400 MHz, CDCl$_3$) δ 8.43 (s, 1H), 7.64 (dd, 1H), 7.54 (dd, 1H), 7.36 (dd, 3H), 7.18 (m, 2H), 4.68 (s, 2H), 3.69 (br, 2H), 3.53-3.38 (br, 6H), 2.01 (m, 2H), 1.52 (m, 2H), 1.39 (s, 9H), 1.18 (m, 2H), 0.73 (t, 3H).

Example 31. Preparation of N-phenyl-N-(3-(6-(piperazine-1-carbonyl)pyridine-3-yl)prop-2-yn-1-yl)pentaneamide (LMT-835)

The tert-butyl 4-(5-(3-((N-phenylpentaneamido)prop-1-yn-1-yl)picolinoyl)piperazine-1-carboxylate (35 mg, 0.69 mmol) obtained in Example 30 was dissolved in acetonitrile (15 ml), and stirred at room temperature for 5 minutes. Dioxane-mixed hydrochloride (4N; 3.73 ml) was added to the mixture, and stirred at the same temperature for 1.5 hours. The reaction solution was concentrated under reduced pressure, and the obtained residue was purified by silica gel column chromatography ($CH_2Cl_2$:MeOH=50:1), thereby obtaining a final product, N-phenyl-N-(3-(6-(piperazine-1-carbonyl)pyridine-3-yl)prop-2-yn-1-yl)pentaneamide (18 mg, 64% yield).

$^1$H NMR (400 MHz, $CDCl_3$) δ 8.43 (s, 1H), 7.66 (dd, 1H), 7.49 (dd, 1H), 7.36 (dd, 3H), 7.21 (m, 2H), 4.67 (s, 2H), 3.70 (br, 2H), 3.48 (br, 2H), 2.90 (br, 2H), 2.81 (br, 2H), 2.01 (m, 2H), 1.49 (m, 2H), 1.17 (m, 2H), 0.73 (t, 3H).

Example 32. Preparation of N-(3-(6-(4-isopropylpiperazine-1-carbonyl)pyridine-3-yl)prop-2-yn-1-yl)-N-phenylpentaneamide (LMT-836)

The N-phenyl-N-(3-(6-(piperazine-1-carbonyl)pyridine-3-yl)prop-2-yn-1-yl)pentaneamide (57.7 mg, 0.14 mmol) obtained in Example 31 and sodium bicarbonate (27 mg, 0.316 mmol) were cooled on ice, and N,N-dimethylformamide (DMF; 2 ml) was added, followed by stirring for 1 hour. 2-iodopropane (30 μl, 0.316 mmol) was added to the mixture, the ice was removed, and the resulting product was heated at 60° C., refluxed, and stirred for 24 hours. The reaction solution was cooled at room temperature and concentrated under reduced pressure, and the obtained residue was diluted with ethyl acetate and washed with water and brine. An organic solvent layer was collected, dehydrated with anhydrous magnesium sulfate ($MgSO_4$), filtered, and then concentrated under reduced pressure. The concentrate was purified by silica gel column chromatography (Hex:EA:MeOH:TEA=12:12:1:0.1), thereby obtaining a final product, N-(3-(6-isopropylpiperazine-1-carbonyl)pyridine-3-yl)prop-2-yn-1-yl)-N-phenylpentaneamide (32.3 mg, 51% yield).

$^1$H NMR (400 MHz, $CDCl_3$) δ 8.44 (s, 1H), 7.65 (dd, 1H), 7.51 (dd, 1H), 7.39 (dd, 3H), 7.22 (m, 2H), 4.68 (s, 2H), 3.74 (br, 2H), 3.52 (br, 2H), 2.67 (m, 1H), 2.55 (br, 2H), 2.41 (br, 2H), 2.02 (m, 2H), 1.50 (m, 2H), 1.15 (m, 2H), 0.98 (d, 6H), 0.74 (t, 3H).

Example 33. Preparation of N,N-diethyl-4-(3-(N-(3-fluorophenyl)pentaneamido)prop-1-yn-1-yl)benzamide (LMT-926)

Step 1: Preparation of 4-bromo-N,N-diethylbenzamide

4-Bromobenzoic acid (5.00 g, 24.9 mmol) was dissolved in N,N-dimethylformamide (100.00 ml), and mixed with diisopropylamine (13 ml, 74.6 mmol). 1-Hydroxybenzotriazole hydrate (7.15 mg, 37.30 mmol) and 1-ethyl-3-(3-dimethylaminopropyl)carbodiimide hydrochloride (5.04 mg, 37.30 mmol) were added to the mixture, and stirred for 5 minutes. Diethylamine (3.1 ml, 37.3 mmol) was added to the mixture, and stirred at room temperature for 12 hours. The reaction solution was concentrated under reduced pressure, and the obtained residue was diluted with dichloromethane and washed with water and brine. An organic solvent layer was collected, dehydrated with anhydrous magnesium sulfate ($MgSO_4$), filtered, and then concentrated under reduced pressure. The concentrate was purified by silica gel column chromatography (Hex:EA=3:1), thereby obtaining 4-bromo-N,N-diethylbenzamide (5.70 g, 89% yield).

Step 2: Preparation of N,N-diethyl-4-(3-hydroxyprop-1-ynyl)benzamide

The 4-bromo-N,N-diethylbenzamide (5.70 mg, 22.3 mmol) obtained in Step 1 and propargyl alcohol (2.60 ml, 44.5 mmol) were dissolved in triethylamine (100.00 ml), and stirred for 5 minutes. Bis(triphenylphosphine)palladium (II) dichloride (1.60 mg, 2.23 mmol) and copper iodide (I) (1.60 mg, 2.23 mmol) were added to the mixture, heated at 60° C., refluxed, and stirred for 17 hours. The reaction solution was cooled at room temperature, concentrated under reduced pressure, and the obtained residue was diluted with ethyl acetate and washed with water and brine. An organic solvent layer was collected, dehydrated with anhydrous magnesium sulfate ($MgSO_4$), filtered, and then concentrated under reduced pressure. The concentrate was purified by silica gel column chromatography (Hex:EA=1:1), thereby obtaining N,N-diethyl-4-(3-hydroxyprop-1-ynyl)benzamide (5.16 mg, 99.9% yield).

Step 3: Preparation of 3-(4-(diethylcarbamoyl)phenyl)prop-2-yn-1-yl methanesulfonate N,N-diethyl-4-(3-hydroxyprop-1-ynyl)benzamide (5.16 mg, 22.3 mmol) was dissolved in dichloromethane (100 ml), and cooled on ice. Triethylamine (4.80 ml, 34.4 mmol) was added to the mixture, and stirred for 5 minutes. Methanesulfonyl chloride (1.95 ml, 25.2 mmol) was added at the same temperature, the ice was removed, and the mixture was stirred at room temperature for 30 minutes. The reaction solution was concentrated under reduced pressure, and the obtained residue was diluted with ethyl acetate and washed with water and brine. An organic solvent layer was collected, dehydrated with anhydrous magnesium sulfate ($MgSO_4$), filtered, and then concentrated under reduced pressure. The concentrate was purified by silica gel column chromatography (Hex:EA=2:1), thereby obtaining 3-(4-(diethylcarbamoyl)phenyl)prop-2-yn-1-yl methanesulfonate (4.2 mg, 59% yield).

Step 4: Preparation of N,N-diethyl-4-(3-(N-(3-fluorophenyl)pentaneamido)prop-1-yn-1-yl)benzamide N-(3-fluorophenyl)pentaneamide (200 mg, 1.02 mmol) was dissolved in tetrahydrofuran (10.00 ml), and cooled on ice. Sodium hydroxide (73 mg, 3.06 mmol) was added to the mixture, and stirred for 1 hour. The 3-(4-(N,N-diethylcarbamoyl)phenyl)prop-2-ynyl methanesulfonate (475 mg, 1.54 mmol) obtained in Step 3 was added at the same temperature, and the mixture was stirred at room temperature for 4 hours. The reaction solution was concentrated under reduced pressure, and the obtained residue was diluted with dichloromethane and washed with water and brine. An organic solvent layer was collected, dehydrated with anhydrous magnesium sulfate ($MgSO_4$), filtered, and then concentrated under reduced pressure. The concentrate was purified by silica gel column chromatography (Hex:EA=2:1), thereby obtaining N,N-diethyl-4-(3-(N-(3-fluorophenyl)pentaneamido)prop-1-yn-1-yl)benzamide (291.7 mg, 70% yield).

1H NMR (CDCl$_3$, 500 MHz) δ 7.43 (1H, t, J=7.5 Hz and 15.0 Hz, aromatic), 7.33 (4H, m, aromatic), 7.09 (3H, m, aromatic), 4.71 (2H, s, CH$_2$), 3.53 (2H, s, CH$_2$), 3.23 (2H, s, CH$_2$), 2.10 (2H, m, CH$_2$), 1.59 (2H, m, CH$_2$), 1.24 (2H, m, CH$_2$), 1.10 (6H, m, (CH$_3$)$_2$), 0.83 (3H, t, J=7.5 Hz and 15.0 Hz, CH$_3$).

Example 34. Preparation of N,N-diethyl-4-(3-(N-(4-fluorophenyl)pentaneamido)prop-1-yn-1-yl)benzamide (LMT-927)

N,N-diethyl-4-(3-(N-(4-fluorophenyl)pentaneamido)prop-1-yn-1-yl)benzamide was obtained (291.7 mg, 70% yield) by the same method as described in Step 4 of Example 33 using N-(4-fluorophenyl)pentaneamide (200 mg, 1.02 mmol) and 3-(4-N,N-(diethylcarbamoyl)phenyl)prop-2-yn-1-yl methanesulfonate.

$^1$H NMR (CDCl$_3$, 500 MHz) δ 7.31 (2H, d, J=3.5 Hz, aromatic), 7.29 (4H, d, J=3.0 Hz, aromatic), 7.15 (2H, t, J=8.5 Hz and 17.0 Hz, aromatic), 4.71 (2H, s, CH$_2$), 3.53 (2H, s, CH$_2$), 3.23 (2H, s, CH$_2$), 2.06 (2H, t, J=7.5 Hz and 15.0 Hz, CH$_2$), 1.57 (2H, m, CH$_2$), 1.22 (2H, m, CH$_2$), 1.10 (6H, s, (CH$_3$)$_2$), 0.82 (3H, t, J=7.5 Hz and 15.0 Hz, CH$_3$).

Example 35. Preparation of N-(3-(4-(N,N-diethylsulfamoyl)phenyl)prop-2-ynyl)-N-phenylpentaneamide (LMT-946)

Step 1: Preparation of 4-bromo-N,N-diethylbenzenesulfonamide

4-Bromobenzenesulfonyl chloride (1.00 g, 3.91 mmol) was dissolved in dichloromethane (30.00 ml), and cooled on ice. Diethylamine (1.19 ml, 11.54 mmol) was added to the mixture and stirred for 5 minutes, the ice was removed, and then the mixture was stirred at room temperature for 12 hours. The reaction solution was concentrated under reduced pressure, and the obtained residue was diluted with dichloromethane and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=3:1), thereby obtaining 4-bromo-N,N-diethylbenzenesulfonamide (1.10 g, 96% yield).

$^1$H NMR (CDCl$_3$, 500 MHz) δ 7.67 (4H, m), 3.23 (4H, q, J=7.0 Hz), 1.13 (6H, t).

Step 2: Preparation of N,N-diethyl-4-(3-hydroxyprop-1-ynyl)benzenesulfonamide

The 4-bromo-N,N-diethylbenzenesulfonamide (500.00 mg, 1.71 mmol) obtained in Step 1 and propargyl alcohol (0.20 ml, 3.42 mmol) were dissolved in triethylamine (10.00 ml), and stirred for 5 minutes. Bis(triphenylphosphine)palladium (II) dichloride (119.32 mg, 0.17 mmol) and copper iodide (I)(32.37 mg, 0.17 mmol) were added to the mixture, heated at 60° C., refluxed, and stirred for 17 hours. The reaction solution was cooled at room temperature and concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=1:1), thereby obtaining N,N-diethyl-4-(3-hydroxyprop-1-ynyl)benzenesulfonamide (286.00 mg, 63% yield).

$^1$H NMR (CDCl$_3$, 500 MHz) δ 7.66 (2H, d, J=8.0 Hz), 7.42 (2H, d, J=8.0 Hz), 4.44 (2H, s), 3.16 (4H, q, J=7.0 Hz), 1.05 (6H, t).

Step 3: Preparation of 3-(4-(N,N-diethylsulfamoyl)phenyl)prop-2-ynyl methanesulfonate The N,N-diethyl-4-(3-hydroxyprop-1-ynyl)benzenesulfonamide (273.00 mg, 1.02 mmol) obtained in Step 2 was dissolved in dichloromethane (10 ml), and cooled on ice. Triethylamine (0.21 ml, 1.53 mmol) was added to the mixture, and stirred for 5 minutes. Methanesulfonyl chloride (0.09 ml, 1.12 mmol) was added at the same temperature, the ice was removed, and the mixture was stirred at room temperature for 30 minutes. The reaction solution was concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=2:1), thereby obtaining 3-(4-(N,N-diethylsulfamoyl)phenyl)prop-2-ynyl methanesulfonate (285.00 mg, 80% yield).

$^1$H NMR (CDCl$_3$, 500 MHz) δ 7.73 (2H, d, J=8.5 Hz), 7.53 (2H, d, J=8.5 Hz), 5.05 (2H, s), 3.19 (4H, q, J=7.0 Hz), 3.12 (3H, s), 1.07 (6H, t).

Step 4: Preparation of 4-(3-bromoprop-1-ynyl)-N,N-diethylbenzenesulfonamide

The 3-(4-(N,N-diethylsulfamoyl)phenyl)prop-2-ynyl methanesulfonate (260.00 mg, 0.75 mmol) obtained in Step 3 was dissolved in tetrahydrofuran (20.00 ml), and cooled on ice. Lithium bromide (196.28 mg, 2.26 mmol) was added to the mixture at the same temperature, and stirred for 4 hours. The reaction solution was concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified using a filter, thereby obtaining 4-(3-bromoprop-1-ynyl)-N,N-diethylbenzenesulfonamide (240.00 mg, 97%).

Step 5: Preparation of N,N-diethyl-4-(3-(phenylamino)prop-1-ynyl)benzenesulfonamide The 4-(3-bromoprop-1-ynyl)-N,N-diethylbenzenesulfonamide (248.00 mg, 0.75 mmol) obtained in Step 4 and potassium carbonate (93.98 mg, 0.68 mmol) were dissolved in acetonitrile (15.00 ml), and stirred for 30 minutes. Aniline (0.06 ml, 0.68 mmol) was added to the mixture, and stirred at room temperature for 9 hours. The reaction solution was concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=2:1), thereby obtaining N,N-diethyl-4-(3-(phenylamino)prop-1-ynyl)benzenesulfonamide (190.00 mg, 81% yield).

$^1$H NMR (CDCl$_3$, 500 MHz) δ 7.71 (2H, d, J=8.5 Hz), 7.46 (2H, d, J=8.5 Hz), 7.23 (2H, t), 6.80 (1H, t), 6.73 (2H, d, J=7.5 Hz), 4.15 (2H, s), 3.21 (4H, m), 1.10 (6H, t).

Step 6: Preparation of N-(3-(4-(N,N-diethylsulfamoyl)phenyl)prop-2-ynyl)-N-phenylpenteamide The N,N-diethyl-4-(3-(phenylamino)prop-1-ynyl)benzenesulfonamide (174.00 mg, 0.51 mmol) obtained in Step 5 was dissolved in dichloromethane (15.00 ml), and cooled on ice. Triethylamine (0.14 ml, 1.02 mmol) was added to the mixture, and stirred for 5 minutes. Valeroyl chloride (0.06 ml, 0.53 mmol) was added at the same temperature, the ice was removed, and the mixture was stirred at room temperature for 4 hours. The reaction solution was concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=2:1), thereby obtaining N-(3-(4-(N,N-diethylsulfamoyl)phenyl)prop-2-ynyl)-N-phenylpentaneamide (153.00 mg, 70% yield).

$^1$H NMR (CDCl$_3$, 500 MHz) δ 7.74 (2H, d, J=8.0 Hz), 7.51 (4H, m), 7.43 (3H, m), 4.73 (2H, s), 3.21 (4H, s), 2.11 (2H, t), 1.52 (2H, m), 1.21 (2H, m), 0.10 (6H, t), 0.80 (3H, t).

Example 36. Preparation of N-(3-(4-(N-isopropylsulfamoyl)phenyl)prop-2-ynyl)-N-phenylpentaneamide (LMT-947)

Step 1: Preparation of 4-bromo-N-isopropylbenzenesulfonamide

4-Bromobenzenesulfonyl chloride (1.00 g, 3.91 mmol) was dissolved in dichloromethane (10.00 ml), and isopropylamine (0.40 ml, 4.69 mmol) and pyridine (0.41 ml, 5.09 mmol) were added to the mixture and stirred at room temperature for 2 hours. The reaction solution was concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=3:1), thereby obtaining 4-bromo-N-isopropylbenzenesulfonamide (730.00 mg, 67% yield).

$^1$H NMR (CDCl$_3$, 500 MHz) δ 7.76-7.64 (4H, m), 3.47 (1H, m), 1.09 (6H, d, J=7.0 Hz).

Step 2: Preparation of 4-(3-hydroxyprop-1-ynyl)-N-isopropylbenzenesulfonamide 4-(3-hydroxyprop-1-ynyl)-N-isopropylbenzenesulfonamide was obtained (420.00 mg, 92% yield) by the same method as described in Step 2 of Example 35 using the 4-bromo-N-isopropylbenzenesulfonamide (500.00 mg, 1.80 mmol) obtained in Step 1 and propargyl alcohol (0.21 ml, 3.59 mmol).

$^1$H NMR (CDCl$_3$, 500 MHz) δ 7.81 (2H, d, J=8.0 Hz), 7.49 (2H, d, J=8.5 Hz), 4.51 (2H, s), 3.44 (1H, m), 1.06 (6H, d, J=6.5 Hz).

Step 3: Preparation of 3-(4-(N-isopropylsulfamoyl)phenyl)prop-2-ynyl methanesulfonate 3-(4-(N-isopropylsulfamoyl)phenyl)prop-2-ynyl methanesulfonate was obtained (330.00 mg, 61% yield) by the same method as described in Step 3 of Example 35 using the 4-(3-hydroxyprop-1-ynyl)-N-isopropylbenzenesulfonamide (410.00 mg, 1.62 mmol) obtained in Step 2 and methanesulfonyl chloride (0.14 ml, 1.78 mmol).

$^1$H NMR (CDCl$_3$, 500 MHz) δ 7.86 (2H, d, J=8.5 Hz), 7.59 (2H, d, J=8.5 Hz), 5.10 (2H, s), 3.47 (1H, m) 3.17 (3H, s), 1.08 (6H, d, J=6.5 Hz).

Step 4: Preparation of 4-(3-bromoprop-1-ynyl)-N-isopropylbenzenesulfonamide 4-(3-bromoprop-1-ynyl)-N-isopropylbenzenesulfonamide was obtained (190.00 mg, 95% yield) by the same method as described in Step 4 of Example 35 using the 3-(4-(N-isopropylsulfamoyl)phenyl)prop-2-ynyl methanesulfonate (210.00 mg, 0.63 mmol) obtained in Step 3 and lithium bromide (165.00 mg, 1.90 mmol).

Step 5: Preparation of N-isopropyl-4-(3-(phenylamino)prop-1-ynyl)benzenesulfonamide N-isopropyl-4-(3-(phenylamino)prop-1-ynyl)benzenesulfonamide was obtained (157 mg, 83% yield) using the 4-(3-bromoprop-1-ynyl)-N-isopropylbenzenesulfonamide (199.00 mg, 0.63 mmol) obtained in Step 4 and aniline (0.05 ml, 0.57 mmol).

$^1$H NMR (CDCl$_3$, 500 MHz) δ 7.80 (2H, d, J=9.0 Hz), 7.50 (2H, d, J=8.5 Hz), 7.25 (2H, m), 6.82 (1H, t), 6.76 (2H, d, J=8.0 Hz), 4.64 (1H, d, J=8.0 Hz), 4.19 (2H, s), 3.45 (1H, m), 1.06 (6H, d, J=6.0 Hz).

Step 6: Preparation of N-(3-(4-(N-isopropylsulfamoyl)phenyl)prop-2-ynyl)-N-phenylpentaneamide N-(3-(4-(N-isopropylsulfamoyl)phenyl)prop-2-ynyl)-N-phenylpentaneamide was obtained (94.00 mg, 49.5% yield) by the same method as described in Step 6 of Example 35 using the N-isopropyl-4-(3-(phenylamino)prop-1-ynyl)benzenesulfonamide (150.00 mg, 0.46 mmol) obtained in Step 2 and valeroyl chloride (0.06 ml, 0.48 mmol).

$^1$H NMR (CDCl$_3$, 500 MHz) δ 7.78 (2H, d, J=8.5 Hz), 7.51-7.37 (7H, m), 4.72 (2H, s), 3.33 (1H, m), 2.10 (2H, t), 1.51 (2H, m), 1.19 (2H, m), 0.99 (6H, d, J=6.5 Hz), 0.78 (3H, t)

Example 37. Preparation of tert-butyl 4-(3-(N-phenylpentaneamido)prop-1-yn-1-yl)benzoate (LMT-1012)

Step 1: Preparation of N-phenylpentaneamide

Aniline (10.00 ml, 107.40 mmol) was dissolved in dichloromethane (150 ml), and cooled on ice. Triethylamine (30.00 ml, 214.80 mmol) was added to the mixture, and stirred for 5 minutes. Valeroyl chloride (16.00 ml, 128.90 mmol) was added at the same temperature, the ice was removed, and the mixture was stirred at room temperature for 2 hours. The reaction solution was concentrated under reduced pressure, and the obtained residue was diluted with ethyl acetate and washed with water and brine. An organic solvent layer was collected, dehydrated with anhydrous magnesium sulfate (MgSO$_{04}$), filtered, and then concentrated under reduced pressure. The concentrate was purified by silica gel column chromatography (Hex:EA=10:1), thereby obtaining N-phenylpentaneamide (19.1 g, 99.9% yield).

$^1$H NMR (CDCl$_3$, 500 MHz) δ 7.55 (2H, d, J=8.0 Hz, aromatic), 7.29 (2H, t, J=7.5 Hz and 15.0 Hz, aromatic), 7.09 (1H, t, J=7.0 Hz and 14.5 Hz, aromatic), 2.35 (2H, t, J=8.0 Hz and 15.5 Hz, CH$_2$), 1.70 (2H, m, CH$_2$), 1.37 (2H, m, CH$_2$), 0.92 (3H, t, J=7.0 Hz and 14.5 Hz, CH$_3$).

Step 2: Preparation of N-phenyl-N-(prop-2-yn-1-yl)pentaneamide

The N-phenylpentaneamide (19.10 g, 107.40 mmol) obtained in Step 1 was dissolved in N,N-dimethylformamide (DMF; 100 ml), and a reaction system was substituted with nitrogen, sodium hydride (5.20 g, 214.80 mmol) was added at a sub-zero temperature and then stirred for 2 hours. Propargyl bromide (18.10 ml, 214.80 mmol) was added to the mixture, and stirred at a sub-zero temperature for 2 hours. Water was added to the reaction solution at a sub-zero temperature, which was then diluted with ethyl acetate, and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=9:1), thereby obtaining N-phenyl-N-(prop-2-yn-1-yl)pentanamide (19.20 g, 83% yield).

$^1$H NMR (CDCl$_3$, 500 MHz) δ 7.42 (2H, m, aromatic), 7.37 (1H, d, J=7.0 Hz, aromatic), 7.26 (2H, m, aromatic), 4.47 (2H, d, J=2.0 Hz, CH$_2$), 2.03 (2H, t, J=7.0 Hz and 15.5 Hz, CH$_2$), 1.53 (2H, m, CH$_2$), 1.20 (2H, m, CH$_2$), 0.77 (3H, t, J=7.5 Hz and 15 Hz, CH$_3$).

Step 3: Preparation of tert-butyl 4-iodobenzoate

Thionyl chloride (2.30 ml, 32.30 mmol) and N,N-dimethylformamide (DMF) (0.02 ml, 0.20 mmol) were added to 4-iodobenzoic acid (1.00 g, 4.00 mmol), and then the reaction system was substituted with nitrogen, heated to 75° C., refluxed, and then stirred for 1 hour. The reaction solution was concentrated under reduced pressure, the obtained residue was dissolved in tetrahydrofuran (5 ml), and then a potassium tert-butoxide 1M solution in THF (4.5 ml) was slowly added at a sub-zero temperature, and stirred for 30 minutes. The reaction solution was concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=9:1), thereby obtaining 2-(trimethylsilyl)ethyl 4-iodobenzoate (14.00 g, 99.9% yield).

$^1$H NMR (CDCl$_3$, 400 MHz) δ 7.77 (2H, d, J=7.5 Hz, aromatic), 7.69 (2H, d, J=8.0 Hz, aromatic), 1.59 (9H, s, (CH$_3$)$_3$).

Step 4: Preparation of tert-butyl 4-(3-(N-phenylpentaneamido)prop-1-yn-1-yl)benzoate The N-phenyl-N-(pro-2-yn-1-yl)pentaneamide (2.30 g, 10.70 mmol) obtained in Step 2 was added to a solution in which the tert-butyl 4-iodobenzoate (4.90 g, 16.00 mmol) obtained in Step 3 was dissolved in tetrahydrofuran (30 ml), and a reaction system was substituted with nitrogen, followed by stirring at room temperature for 5 minutes. Triethylamine (24 ml), bis(triphenylphosphine)palladium (II) dichloride (75.00 mg, 0.10 mmol) and copper iodide (I) (41.00 mg, 0.21 mmol) were added to the mixture, and stirred at room temperature for 16 hours. The resulting product was concentrated under reduced pressure, and the obtained residue was diluted with dichloromethane and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=4:1), thereby obtaining tert-butyl 4-(3-(N-phenylpentaneamido)prop-1-yn-1-yl)benzoate (3.30 g, 78.3% yield).

$^1$H-NMR (500 MHz, CDCl$_3$): δ 7.88 (2H, d, J=8.0 Hz, aromatic), 7.45 (2H, m, aromatic), 7.39 (1H, d, J=7.0 Hz, aromatic), 7.35 (2H, d, J=8.0 Hz, aromatic), 7.30 (2H, d, J=5.0 Hz, aromatic), 4.72 (2H, s, CH$_2$), 2.07 (2H, t, J=7.5 Hz and 15 Hz, CH$_2$), 1.56 (2H, m, CH$_2$), 1.51 (9H, s, (CH$_3$)$_3$), 1.22 (2H, m, CH$_2$), 0.80 (3H, t, 7.5 Hz and 15 Hz7.5 Hz and 15 Hz, CH$_3$).

Example 38. Preparation of 4-(3-(N-phenylpentaneamido)prop-1-yn-1-yl)benzoic acid (LMT-1013)

The tert-butyl 4-(3-(N-phenylpentaneamido)prop-1-yn-1-yl)benzoate (2.00 g, 5.10 mmol) obtained in Example 37 was dissolved in acetonitrile (48 ml), and stirred at a sub-zero temperature for 5 minutes. Trifluoroacetic acid (12 ml) was slowly added to the solution, and stirred at room temperature for 48 hours. The reaction solution was concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified by silica gel column chromatography (HEX:EA=2:1), thereby obtaining 4-(3-(N-phenylpentaneamido)pro-1-yn-1-yl)benzoic acid (1.6 g, 95% yield).

$^1$H-NMR (500 MHz, MeOD): δ 7.95 (2H, d, J=8.5 Hz, aromatic), 7.51 (2H, m, aromatic), 7.45 (1H, m, aromatic), 7.44 (2H, d, J=8.5 Hz, aromatic), 7.39 (2H, d, J=8.0 Hz, aromatic), 4.73 (2H, s, CH$_2$), 2.11 (2H, t, CH$_3$), 1.21 (2H, m, CH$_2$), 0.83 (3H, t, CH$_3$).

Example 39. Preparation of N-ethyl-4-(3-(N-phenylpentaneamido)prop-1-yn-1-yl)benzamide (LMT-1017)

The 4-(3-(N-phenylpentaneamido)prop-1-yn-1-yl)benzoic acid (80.00 mg, 0.24 mmol) obtained in Example 38 was dissolved in N,N-dimethylformamide (DMF; 0.70 ml), ethylaminehydrochloride (29.20 mg, 0.36 mmol) and 1-hydroxybenzotriazole hydrate (48.4 mg, 0.36 mmol), which were stirred in triethylamine (0.70 ml) for 1 hour, and 1-ethyl-3-(3-dimethylaminopropyl)carbodiimide hydrochloride (55.5 mg, 0.36 mmol) were added to the solution and then stirred at room temperature for 16 hours. The reaction solution was diluted with ethyl acetate and washed with water and brine. An organic solvent layer was collected, dehydrated with anhydrous magnesium sulfate (MgSO$_4$), filtered, and then concentrated under reduced pressure. The concentrate was purified by silica gel column chromatography (Hex:EA=1:1), thereby obtaining N-ethyl-4-(3-(N-phenylpentaneamido)prop-1-yn-1-yl)benzamide (56.8 mg, 66% yield).

¹H NMR (CDCl₃, 500 MHz) δ 7.69 (2H, d, J=8.5 Hz, aromatic), 7.39 (7H, m, aromatic), 4.72 (2H, s, CH₂), 3.49 (2H, t, J=6.0 Hz and 13.0 Hz, CH₂), 2.08 (2H, t, J=7.5 Hz and 15.0 Hz, CH₂), 1.57 (2H, m, CH₂), 1.23 (2H, m, CH₂), 0.81 (3H, t, J=7.5 Hz and 14.5 Hz, CH₃).

Example 40. Preparation of N-(2-(dimethylamino) ethyl)-4-(3-(N-phenylpentaneamido)prop-1-yn-1-yl) benzamide (LMT-1016)

N-(2-(diethylamino)ethyl)-4-(3-(N-phenylpentaneamido) prop-1-yn-1-yl)benzamide was obtained (71.72 mg, 74% yield) by the same method as described in Example 39 using the 4-(3-(N-phenylpentaneamido)pro-1-yn-1-yl)benzoic acid (80.00 mg, 0.24 mmol) obtained in Example 38 and N,N-dimethylethane-1,2-diamine (0.04 ml, 0.36 mmol).
¹H NMR (CDCl₃, 500 MHz) δ 7.71 (2H, d, J=8.0 Hz, aromatic), 7.38 (7H, m, aromatic), 4.70 (2H, s, CH₂), 3.48 (2H, m, CH₂), 2.50 (2H, t, J=6.0 Hz and 11.5 Hz, CH₂), 2.24 (6H, s, (CH₃)₂), 2.05 (2H, t, J=7.5 Hz and 15.0 Hz, CH₂), 1.54 (2H, m, CH₂), 1.20 (2H, m, CH₂), 0.78 (3H, t, J=7.0 Hz and 14.0 Hz, CH₃).

Example 41. Preparation of ethyl 2-(4-(3-(N-phenylpentaneamido)prop-1-yn-1-yl)benzamido)acetate (LMT-1014)

Ethyl 2-(4-(3-(N-phenylpentaneamido)prop-1-yn-1-yl) benzamido)acetate was obtained (102.18 mg, 54% yield) by the same method as described in Example 39 using the 4-(3-(N-phenylpentaneamido)pro-1-yn-1-yl)benzoic acid (150.00 mg, 0.45 mmol) obtained in Example 38 and glycineethylester hydrochloride (93.70 mg, 0.67 mmol).
¹H NMR (CDCl₃, 500 MHz) δ 7.74 (2H, d, J=8.0 Hz, aromatic), 7.37 (7H, m, aromatic), 4.22 (4H, m, (CH₂)₂), 2.07 (2H, t, J=7.5 Hz and 15.0 Hz, CH₂), 1.56 (2H, m, CH₂), 1.30 (5H, m, CH₃, CH₂), 1.22 (2H, m, CH₂), 0.80 (3H, t, J=7.5 Hz and 14.5 Hz, CH₃).

Example 42. Preparation of 2-(4-(3-(N-phenylpentaneamido)prop-1-yn-1-yl)benzamido)acetic acid (LMT-1015)

The ethyl 2-(4-(3-(N-phenylpentaneamido)prop-1-yn-1-yl)benzamido)acetate (46.20 mg, 0.10 mmol) obtained in Example 41 and a 2M sodium hydroxide aqueous solution (0.07 ml, 0.14 mmol) were dissolved in methanol (0.1 ml), and stirred at room temperature for 30 minutes. The acidity of the reaction solution was increased using hydrochloric acid, which was then diluted with ethylacetate, and washed with water and brine. An organic solvent layer was collected, dehydrated with anhydrous magnesium sulfate (MgSO₄), filtered, and then concentrated under reduced pressure. The concentrate was recrystallized using hexene and ethylacetate, thereby obtaining 2-(4-(3-(N-phenylpentaneamido) prop-1-yn-1-yl)benzamido)acetic acid (20.80 mg, 53% yield).
¹H NMR (CDCl₃, 500 MHz) δ 7.71 (2H, d, J=8.5 Hz, aromatic), 7.40 (7H, m, aromatic), 4.71 (2H, s, CH₂), 4.23 (2H, d, J=5.0 Hz, CH₂), 2.10 (2H, t, J=7.5 Hz and 15.5 Hz, CH₂), 1.56 (2H, m, CH₂), 1.22 (2H, m, CH₂), 0.80 (3H, t, J=7.0 Hz and 14.5 Hz, CH₃).

Example 43. Preparation of methyl 2-(4-(3-(N-phenylpentaneamido)prop-1-yn-1-yl)benzamido)propanoate (LMT-1018)

Methyl 2-(4-(3-(N-phenylpentaneamido)prop-1-yn-1-yl) benzamido)propanoate was obtained (110.00 mg, 42% yield) using the 4-(3-(N-phenylpentaneamido)pro-1-yn-1-yl)benzoic acid (100.00 mg, 0.30 mmol) obtained in Example 38 and L-alaninemethylester hydrochloride (83.70 mg, 0.60 mmol).
¹H NMR (CDCl₃, 500 MHz) δ 7.72 (2H, d, J=8.5 Hz, aromatic), 7.37 (7H, m, aromatic), 4.76 (1H, t, J=7.5 Hz and 14.5 Hz CH), 4.71 (2H, s, CH₂), 3.76 (3H, s, CH₃), 2.06 (2H, t, J=7.5 Hz and 15.5 Hz, CH₂), 1.53 (2H, m, CH₂), 1.50 (3H, d, J=7.5 Hz, CH₃), 1.20 (2H, m, CH₂), 0.79 (3H, t, J=7.5 Hz and 15.0 Hz, CH₃).

Example 44. Preparation of 2-(4-(3-(N-phenylpentaneamido)prop-1-yn-1-yl)benzamido)propanoic acid (LMT-1019)

2-(4-(3-(N-phenylpentaneamido)prop-1-yn-1-yl)benzamido)propanoic acid was obtained (45.00 mg, 55% yield) using the methyl 2-(4-(3-(N-phenylpentaneamido)prop-1-yn-1-yl)benzamido)propanoate (86.50 mg, 0.20 mmol) obtained in Example 43.
¹H NMR (CDCl₃, 500 MHz) δ 7.71 (2H, d, J=8.0 Hz, aromatic), 7.40 (7H, m, aromatic), 4.76 (1H, t, J=7.5 Hz and 14.5 Hz, CH), 4.72 (2H, s, CH₂), 2.10 (2H, t, J=7.5 Hz and 15.5 Hz, CH₂), 1.57 (5H, m, CH₃, CH₂), 1.22 (2H, m, CH₂), 0.80 (3H, t, J=7.5 Hz and 15.0 Hz, CH₃).

Example 45. Preparation of 2-(4-(3-(N-(3-fluorophenyl)pentaneamido)prop-1-ynyl)phenoxy)acetic acid (LMT-1009)

Step 1: Preparation of N-(3-fluorophenyl)pentaneamide

N-(3-fluorophenyl)pentaneamide was obtained (349.00 mg, 99% yield) by the same method as described in Step 1 of Example 37 using 3-fluoroaniline (200.00 mg, 1.79 mmol).
¹H NMR (CDCl₃, 500 MHz) δ 8.10 (1H, s), 7.51 (1H, d, J=11.0 Hz), 7.20 (2H, m), 6.79 (1H, m), 2.36 (2H, t), 1.68 (2H, m), 1.36 (2H, m), 0.91 (3H, t)

Step 2: Preparation of N-(3-fluorophenyl)-N-(prop-2-ynyl)pentaneamide

The N-(3-fluorophenyl)pentaneamide (400.00 mg, 2.05 mmol) obtained in Step 1, potassium hydroxide (230.61 mg, 4.11 mmol), and tetrabutyl ammonium iodide (37.87 mg, 0.20 mmol) were dissolved in tetrahydrofuran (20.00 ml), and stirred for 20 minutes. Propargyl bromide (0.19 ml, 2.30 mmol) was added to the mixture at the same temperature, and stirred for 20 hours. The reaction solution was concentrated under reduced pressure, and the obtained residue was diluted with ethyl acetate and washed with water and brine. An organic solvent layer was collected, dehydrated with anhydrous magnesium sulfate (MgSO₄), filtered, and then concentrated under reduced pressure. The concentrate was purified by silica gel column chromatography (Hex:EA=10:1), thereby obtaining N-(3-fluorophenyl)-N-(prop-2-ynyl) pentaneamide (450.00 mg, 94% yield).
1H NMR (CDCl₃, 500 MHz) δ 7.42 (1H, m), 7.11 (2H, m), 7.20 (1H, d, J=9.0 Hz), 4.46 (2H, s), 2.07 (2H, t), 1.56 (2H, m), 1.22 (2H, m), 0.82 (3H, t)

Step 3: Preparation of N-(3-fluorophenyl)-N-(3-(4-hydroxyphenyl)prop-2-ynyl)pentaneamide N-(3-fluorophenyl)-N-(3-(4-hydroxyphenyl)prop-2-ynyl) pentaneamide was obtained (128.00 mg, 67.8% yield) using the N-(3-fluorophenyl)-N-(prop-2-ynyl)pentaneamide (270.00 mg, 1.16 mmol) obtained in Step 2 and 4-iodophenol (127.60 mg, 0.58 mmol).

$^1$H NMR (CDCl$_3$, 500 MHz) δ 7.51 (1H, m), 7.21 (5H, m), 6.71 (2H, d, J=9.0 Hz), 7.65 (2H, s), 2.13 (2H, t), 1.54 (2H, m), 1.26 (2H, m), 0.82 (3H, t)

Step 4: Preparation of ethyl 2-(4-(3-(N-(3-fluorophenyl)pentaneamido)prop-1-ynyl)phenoxy)acetate Ethyl 2-(4-(3-(N-(3-fluorophenyl)pentaneamido)prop-1-ynyl)phenoxy)acetate was obtained (113.00 mg, 74% yield) using the N-(3-fluorophenyl)-N-(3-(4-hydroxyphenyl)prop-2-ynyl)pentaneamide (120.00 mg, 0.37 mmol) obtained in Step 3 and potassium carbonate (153.41 mg, 1.11 mmol).

$^1$H NMR (CDCl$_3$, 500 MHz) δ 7.42 (1H, m), 7.28 (2H, d, J=9.0 Hz), 7.09 (3H, m), 6.81 (2H, d, J=9.0 Hz), 4.68 (2H, s), 4.61 (2H, s), 4.27 (2H, m), 2.05 (2H, t), 1.58 (2H, m), 1.26 (5H, m), 0.82 (3H, t)

Step 5: Preparation of 2-(4-(3-(N-(3-fluorophenyl)pentaneamido)prop-1-ynyl)phenoxy)acetic acid The ethyl 2-(4-(3-(N-(3-fluorophenyl)pentaneamido) prop-1-ynyl)phenoxy)acetate (100.00 mg, 0.24 mmol) obtained in Step 4 was dissolved in ethanol (9.00 ml), and stirred for 5 minutes. 2M sodium hydroxide (0.30 ml) was added to the mixture, heated at 80° C., refluxed, and stirred for 3 hours. The reaction solution was cooled at room temperature and concentrated under reduced pressure, and the obtained residue was diluted with ethyl acetate and washed with water and brine. An organic solvent layer was collected, dehydrated with anhydrous magnesium sulfate (MgSO$_4$), filtered, and then concentrated under reduced pressure. The concentrate was purified by ODS column chromatography (MeOD:H2O=2:1), thereby obtaining 2-(4-(3-(N-(3-fluorophenyl)pentaneamido)prop-1-ynyl)phenoxy)acetic acid (15.00 mg, 16% yield)

$^1$H NMR (CDCl$_3$, 500 MHz) δ 7.52 (1H, d, J=7.0 Hz), 7.24 (5H, m), 6.88 (2H, d, J=8.5 Hz), 4.68 (2H, s), 4.66 (2H, s), 2.14 (2H, t), 1.55 (2H, m), 1.24 (2H, m), 0.83 (3H, t)

Example 46. Preparation of 2-(4-(3-(N-(4-fluorophenyl)pentaneamido)prop-1-ynyl)phenoxy)acetic acid (LMT-1010)

Step 1: Preparation of N-(4-fluorophenyl)pentaneamide

N-(4-fluorophenyl)pentaneamide was obtained (870.00 mg, 99% yield) by the same method as described in Step 1 of Example 37 using 4-fluoroaniline (500.00 mg, 4.49 mmol) and valeroyl chloride (1.10 ml, 8.99 mmol).

$^1$H NMR (CDCl$_3$, 400 MHz) δ 8.16 (1H, br), 7.48-7.45 (2H, m), 6.97-6.94 (2H, m), 2.34-2.31 (2H, t), 1.68-1.65 (2H, m), 1.38-1.33 (2H, m), 0.92-0.89 (3H, t).

Step 2: Preparation of N-(4-fluorophenyl)-N-(prop-2-ynyl)pentaneamide

N-(4-fluorophenyl)-N-(prop-2-ynyl)pentaneamide was obtained (347.60 mg, 57% yield) by the same method as described in Step 2 of Example 45 using the N-(4-fluorophenyl)pentaneamide (500.00 mg, 2.56 mmol) obtained in Step 1 and propargyl bromide (0.24 ml, 2.81 mmol).

$^1$H NMR (CDCl$_3$, 500 MHz) δ 7.27 (2H, m), 7.14 (2H, m), 4.46 (2H, s), 2.04 (2H, t), 1.55 (2H, m), 1.21 (2H, m), 0.81 (3H, t)

Step 3: Preparation of N-(4-fluorophenyl)-N-(3-(4-hydroxyphenyl)prop-2-ynyl)pentaneamide N-(4-fluorophenyl)-N-(3-(4-hydroxyphenyl)prop-2-ynyl) pentaneamide was obtained (117.00 mg, 56% yield) using the N-(4-fluorophenyl)-N-(prop-2-ynyl)pentaneamide (300.00 mg, 1.29 mmol) obtained in Step 3 and 4-iodophenol (140.80 mg, 0.64 mmol).

$^1$H NMR (CDCl$_3$, 500 MHz) δ 7.22 (6H, m), 6.84 (2H, d, J=8.0 Hz), 4.65 (2H, s), 2.06 (2H, t), 1.55 (2H, m), 1.21 (2H, m), 0.79 (3H, t)

Step 4: Preparation of ethyl 2-(4-(3-(N-(4-fluorophenyl)pentaneamido)prop-1-ynyl)phenoxy)acetate Ethyl 2-(4-(3-(N-(4-fluorophenyl)pentaneamido)prop-1-ynyl)phenoxy)acetate was obtained (113.00 mg, 81% yield) by the same method as described in Step 1 of Example 27 using the N-(4-fluorophenyl)-N-(3-(4-hydroxyphenyl)prop-2-ynyl)pentaneamide (110.00 mg, 0.34 mmol) obtained in Step 3 and ethyl bromoacetate (0.04 ml, 0.37 mmol).

$^1$H NMR (CDCl$_3$, 500 MHz) δ 7.21 (6H, m), 6.79 (2H, d, J=9.0 Hz), 4.65 (2H, s), 4.59 (2H, s), 4.24 (2H, m), 2.01 (2H, t), 1.52 (2H, m), 1.21 (5H, m), 0.79 (3H, t)

Step 5: Preparation of 2-(4-(3-(N-(4-fluorophenyl)pentaneamido)prop-1-ynyl)phenoxy)acetic acid 2-(4-(3-(N-(4-fluorophenyl)pentaneamido)prop-1-ynyl) phenoxy)acetic acid was obtained (25.00 mg, 27% yield) by the same method as described in Step 5 of Example 28 using the ethyl 2-(4-(3-(N-(4-fluorophenyl)pentaneamido)prop-1-ynyl)phenoxy)acetate (100.00 mg, 0.24 mmol) obtained in Step 4.

$^1$H NMR (CDCl$_3$, 500 MHz) δ 7.41 (2H, m), 7.26 (4H, m), 6.88 (2H, d, J=7.0 Hz), 4.66 (2H, s), 4.60 (2H, s), 2.10 (2H, t), 1.52 (2H, m), 1.23 (2H, m), 0.82 (3H, t)

EXPERIMENTAL EXAMPLES

Experimental Example 1. Preparation of BLT2-Expressing Cells or BLT2-Nonexpressing Cells For this experiment, BLT2-nonexpressing cells and BLT2-expressing cells (CHO-BLT2 cells) were prepared by the following method.

CHO cells were obtained from Korean Cell Line Bank (KCLB, 10061), and cultured in an RPMI 1640 medium (Invitrogen) containing 10% fetal bovine serum (FBS; Life Technologies, Inc.), penicillin (50 units/mL) and an antibiotic antimycotic solution (Life Technologies, Inc.) at 37° C. under a 5% CO$_2$ condition. The cells were split for 3 days using Trypsin-EDTA, maintained in a growth phase, washed with phosphate-buffered saline (PBS; 137 mM NaCl, 2.7 mM KCl, 10 mM Na$_2$HPO$_4$, 2 mM KH$_2$PO$_4$), and then added to a new medium, thereby preparing BLT2-nonexpressing cells.

In addition, to prepare stable CHO/BLT2 clones, CHO-K1 cells were transformed with pcDNA3-long form BLT2 encoding HA-tagged human BLT2, and selected with 0.4 mg/ml of G418 (Invitrogen, Carlsbad, Calif., USA). To screen BLT2 expression, the selected clones were analyzed by RT-PCR using a human-specific BLT2 primer, and representative clones used for the experiment were BLT2-expressing cells (CHO-BLT2 cells).

Experimental Example 2. Confirmation of Inhibitory Effect on Growth of BLT2-Expressing Cells Cell viability according to treatment of the compounds prepared in the examples were measured by a 3-(4,5-dimethylthiazol-2-yl)-2,5-diphenyltetrazolium bromide (MTT) method.

More specifically, $1 \times 10^4$ each of the BLT2-nonexpressing cells (CHO-pcDNA3.1 cells) and BLT2-expressing cells (CHO-BLT2 cells), which were prepared in Experimental Example 1, were dispensed in a 96-mm culture dish, and cultured for 24 hours. Afterward, the culture medium was removed, a serum-free RPMI medium was added, and after two hours, the cells were pre-treated with each of the compound prepared in one of the examples (10 μM), 10 μM DMSO (compound solvent) as a control, and 10 μM 1-[5-ethyl-2-hydroxy-4-[[6-methyl-6-(1H-tetrazol-5-yl)heptyl]oxy]phenyl]-ethanone (LY255283; Cayman) as a positive control for 1 hour. Subsequently, after treatment of $LTB_4$ (300 nM), the cells were cultured for 24 hours. 20 μL of an MTT solution (5 mg/mL, Sigma-Aldrich) was added to each well, the cells were cultured in a humid $CO_2$ incubator at 37° C. for 4 hours, a supernatant was removed, and 200 μL of DMSO was added to each well to dissolve insoluble violet formazan crystals. Absorbance was measured using a microplate reader (Molecular Devices, Sunnyvale, Calif.) at 550 nm, and the measurement was repeated three times.

As a result, as shown in FIGS. 1A to 1E, when BLT2-expressing cells (CHO-BLT2 cells) were treated with $LTB_4$ (300 nM), which is a ligand of BLT2 (DMSO+) were compared with BLT2-expressing cells (CHO-BLT2 cells) treated with ethanol (DMSO−), cell growth increased 20% to 35%, and when BLT2-expressing cells (CHO-BLT2 cells) pre-treated with the positive control LY255283, were compared with those treated with the control DMSO, approximately 90% cell growth was exhibited, and therefore, it was confirmed that the inhibitory effect on cell growth was exhibited by the treatment of the compounds of the examples. Specifically, when a compound of the present invention (LMT-692, LMT-694, LMT-696 or LMT-1013) was pre-treated at 10 μM, compared with the control DMSO, 88.0%, 16.7%, 56.6% or 96.3% cell growth was exhibited, respectively, and thus the growth inhibitory effect was confirmed. Likewise, LMT-837 (65%), LMT-841 (60%), LMT-842 (70%), LMT-883 (99%), LMT-886 (99%), LMT-1016 (99%), LMT-1018 (71.6%), and LMT-1019 (99%) compounds also showed the growth inhibitory effect.

The experimental results show that the compounds of the present invention (LMT-692, LMT-696, LMT-837, LMT-841, LMT-842, LMT-883, LMT-886, LMT-1013, LMT-1016, LMT-1018, and LMT-1019) can inhibit BLT2-induced cell growth with very excellent efficiency, and the compounds may be used as pharmaceutical components (BLT2-blocking pharmacological molecules) that can be used as therapeutic agents for inhibiting cancer, asthma or different types of BLT2-associated inflammatory diseases.

Experimental Example 3. Confirmation of $LTB_4$-Induced BLT2-Dependent Chemotactic Motility Inhibitory Effect Chemotactic motility was analyzed using a Transwell chamber including a polycarbonate filter (8-μm pore size, Corning Costar) with a 6.5-mm diameter. Specifically, the lower surface of the filter was coated with 10 μg/mL fibronectin in a serum-free RPMI 1640 medium at 37° C. for 1 hour. The experiment was performed by placing the filter dried and coated with RPMI 1640 media containing various amounts of $LTB_4$ in the lower wells of the Transwell chamber, and loading CHO cells stably expressing BLT1 and BLT2 into the upper wells containing serum-free RPMI 1640 media finally at $2 \times 10^4$ cells/100 μL. To evaluate the effect of inhibitors, the cells were pre-treated with each inhibitor for 30 minutes before dispensing. After the cells were cultured at 37° C. in 5% $CO_2$ for 3 hours, the filters were fixed with methanol for 3 minutes, and stained with hematoxylin and eosin for 10 minutes. In the experiment, the cells were BLT2-expressing cells (CHO-BLT2 cells) and BLT1-expressing cells (CHO-BLT1 cells), and LY255283 and U75302 were used as positive controls for each type of the cells, and BLT2 ligand $LTB_4$, (300 nM), BLT1 ligand $LTB_4$ (10 nM), and lysophosphatidic acid (LPA; 100 nM) were used as comparative controls. The chemotactic motility was quantitatively analyzed by counting the cells on the lower side of the filter under an optical microscope (magnification, 200×). For each analysis, 6 fields were subjected to counting, each sample was analyzed twice, and the analysis was repeated three times.

Figure 2A:
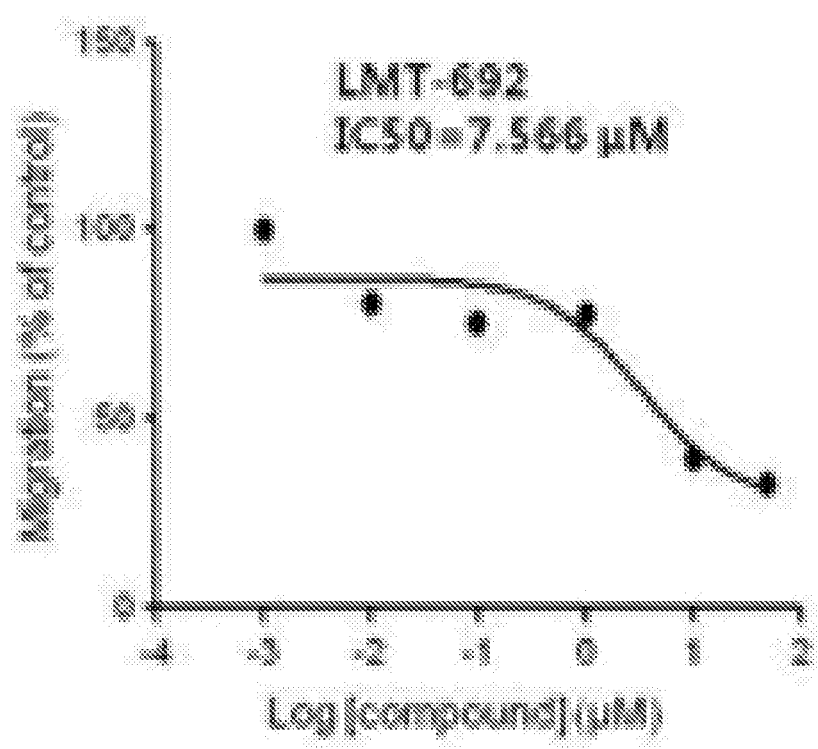
FIGS. 2A and 2B show the results of confirming an effect of inhibiting cell chemotactic motility and the 50% inhibition concentration ($IC_{50}$) in BLT2-expressing cells (CHO-BLT2 cells) by treatment of a compound of the present invention.
Figure 2B:
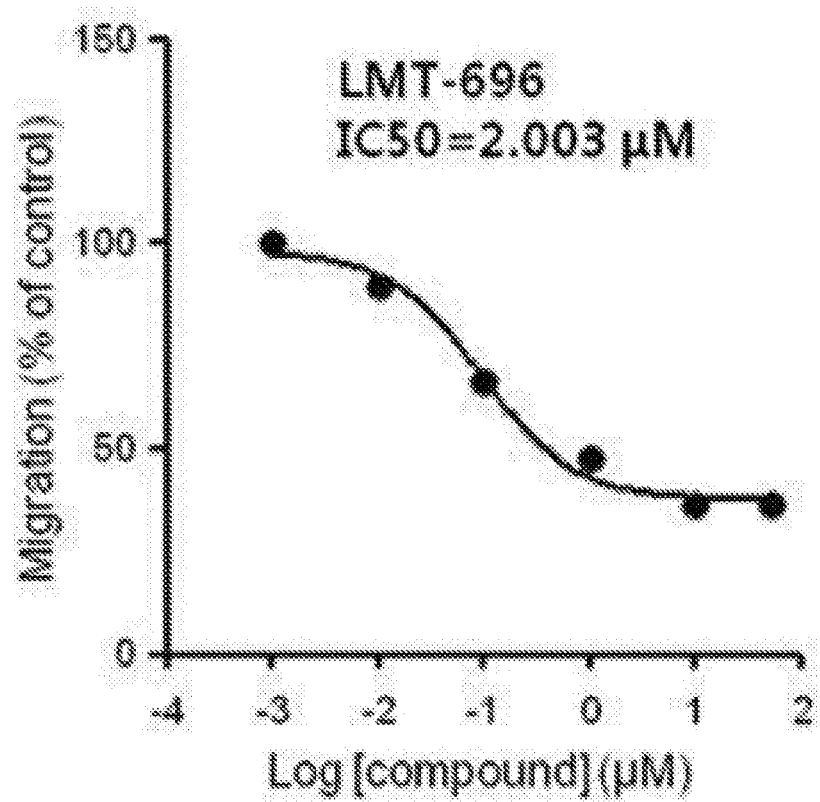

As a result, as shown in FIGS. 2A and 2B and Table 1 below, in the BLT2-expressing cells (CHO-BLT2 cells), as the concentrations of the compound of the present invention (LMT-692 or LMT-696) was increased ($10^{-4}$, $10^{-3}$, $10^{-2}$, $10^{-1}$, 1, 10 and $10^2$), the chemotactic motility of the CHO-BLT2 cells was inhibited under a serum-free condition, and the 50% inhibitory concentrations ($IC_{50}$) of the LMT-692 and LMT-696 compounds were 7.566 μM and 2.003 μM, respectively.

TABLE 1

| | | IC50, μM | |
|---|---|---|---|
| receptor | $LTB_4$, nM | LMT-692 | LMT-696 |
| BLT2 | 300 | 7.566 | 2.003 |

In addition, as shown in Table 2 below, it was confirmed that, in the BLT2-expressing cells (CHO-BLT2 cells), as the concentration of the compound of the present invention LMT-1013 is increased, the chemotactic motility of the CHO-BLT2 cells was inhibited under a serum-free condition, and the $IC_{50}$ of the LMT-1013 compound was 62.35 nM.

Likewise, it was confirmed that, in the BLT1-expressing cells (CHO-BLT1 cells), as the concentration of the compound of the present invention LMT-1013 was increased, the chemotactic motility of the CHO-BLT2 cells was inhibited under a serum-free condition, and the $IC_{50}$ of the LMT-1013 compound was 10 μM or more.

TABLE 2

| Receptor | $LTB_4$, nM | IC50, nM LMT-1013 |
|---|---|---|
| BLT1 | 10 | >10 μM |
| BLT2 | 300 | 62.38 |

Figure 3A:
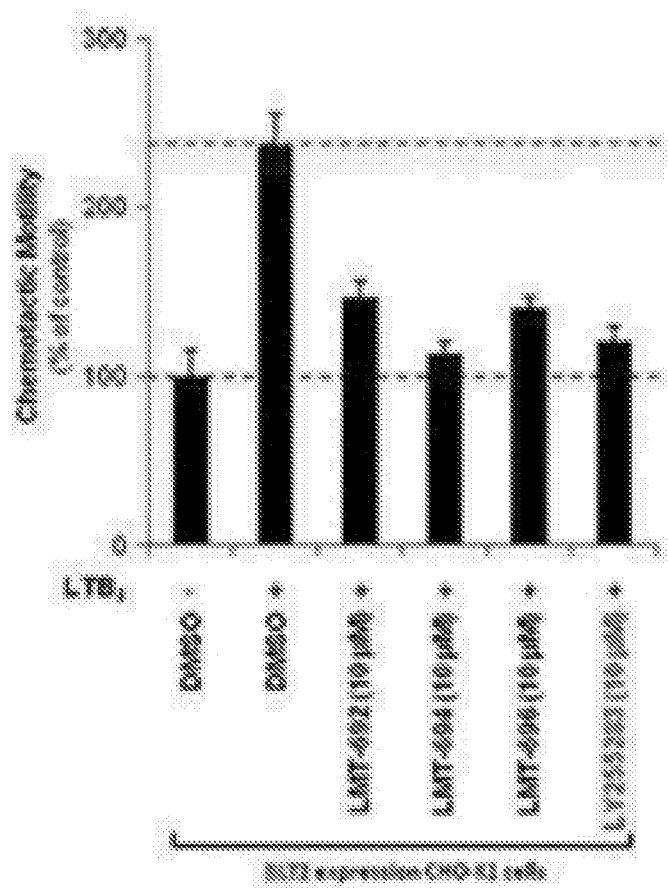
FIGS. 3A and 3B show the results of confirming an effect of inhibiting cell chemotactic motility in BLT2-expressing cells (CHO-BLT2 cells) or BLT1-expressing cells (CHO-BLT1 cells) by treatment of a compound of the present invention.
Figure 3B:
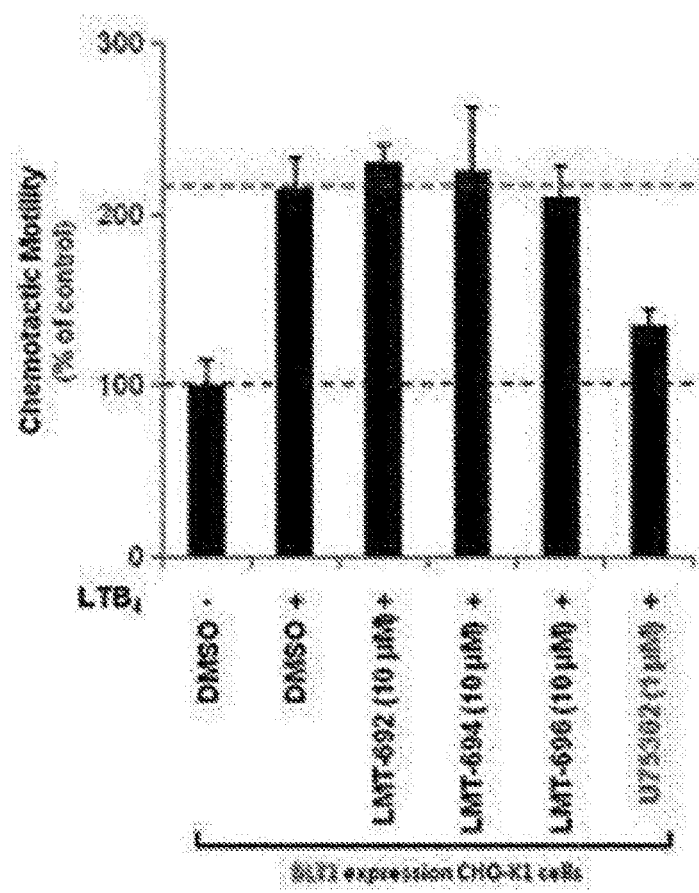

In addition, as shown in FIGS. 3A and 3B, when the BLT2-expressing cells (CHO-BLT2 cells) were treated with the BLT2 ligand $LTB_4$ (300 nM) (DMSO+), compared with those treated with ethanol (DMSO−), cell chemotactic motility increased 2.4-fold, and the cells pre-treated with LY255283 used as a positive control (10 μM) exhibited 90% chemotactic motility as compared with the cells treated with the ligand $LTB_4$. Likewise, it was confirmed that, when the BLT1-expressing cells (CHO-BLT1 cells) were treated with the ligand $LTB_4$ (10 nM) (DMSO+), compared with those treated with ethanol (DMSO−), the cell chemotactic motility was increased 2.2-fold, and the cells pre-treated with U75302 used as a positive control (10 μM) exhibited 90% chemotactic motility as compared with those treated with the ligand $LTB_4$. However, it was confirmed that, when the BLT2-expressing cells were pre-treated with the compound of the present invention (LMT-692, LMT-694 or LMT-696) at 10 μM, compared with those treated with the ligand $LTB_4$ (DMSO+), the chemotactic motility was 66%, 90% or 70.3% inhibited, respectively, but the BLT1-expressing cells (CHO-BLT1 cells), compared with the ligand $LTB_4$ (DMSO+), did not exhibit the inhibitory effect on chemotactic motility.

The results show that, in the cells in which BLT2 was stably expressed (CHO-BLT2 cells), chemotactic motility was increased due to $LTB_4$ stimulus, the compound of the present invention (LMT-692, LMT-696, or LMT-1013) may considerably inhibit chemotactic motility, and thus can be used as a pharmaceutical component to inhibit $LTB_4$-induced BLT2-dependent chemotactic motility.

Experimental Example 4. Confirmation of $LTB_4$ and BLT2 Binding Inhibitory Effect The inhibition of $LTB_4$ and BLT2 binding (ligand binding affinity) was analyzed using radioactive tritium ($^3$H)-labeled $LTB_4$ ([$^3$H]$LTB_4$, ARC; specific activity 160.0 Ci/mmol). After $2 \times 10^6$ of CHO-BLT2 cells were plated into a 100-mm culture dish and cultured for 48 hours, an experimental method was carried out as follows: Collected cells were treated using a homogenizer a total of five times for 1 minute each to separate proteins of the cell membrane. Afterward, the cells were subjected to centrifugation at 4° C. and 45,000 rpm for 40 minutes to only collect the proteins of the cell membrane, and thereby, a protein concentration of 40 μg/45 μL was quantified. When a BLT2-containing cell membrane proteins which were quantified in the same manner was treated with the same amount of [$^3$H]$LTB_4$ (5 nM), and then a different concentration ($10^{-9}$, $10^{-8}$, $10^{-7}$, $10^{-6}$ or $10^{-5}$ M) of a compound, a degree of inhibiting the tritium-labeled $LTB_4$ and BLT2 binding was measured using a Hidex 300sL liquid scintillation counter.

Figure 4A:
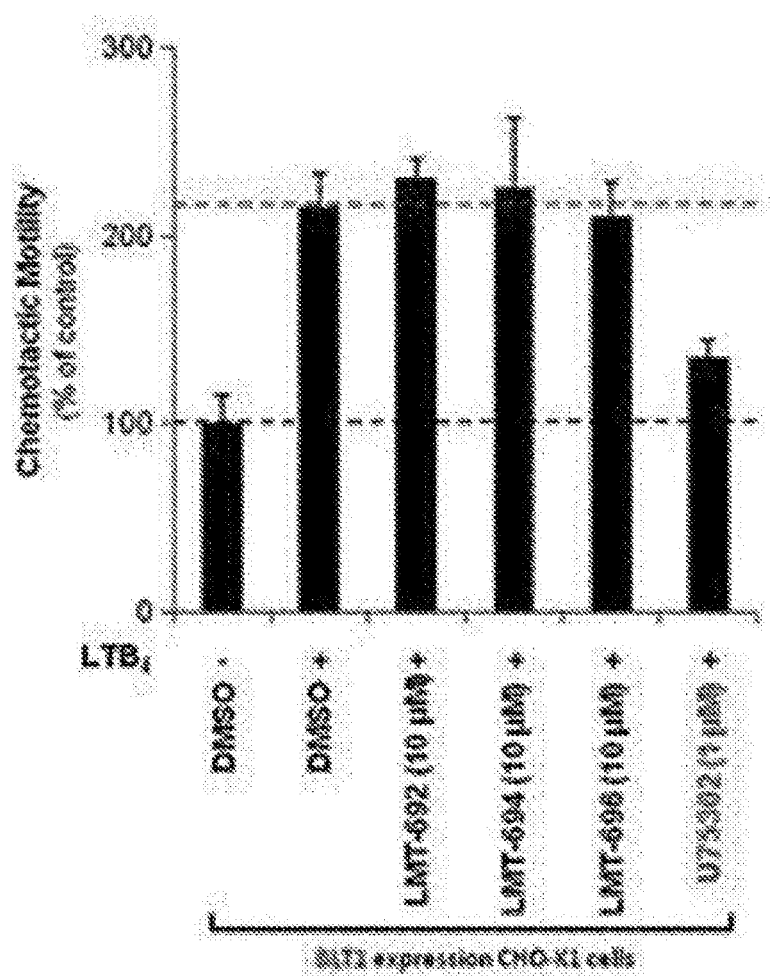
FIGS. 4A and 4B show the results of confirming $LTB_4$ and BLT2 binding inhibitory effects in BLT2-expressing cells (CHO-BLT2 cells) by treatment of a compound of the present invention.
Figure 4B:
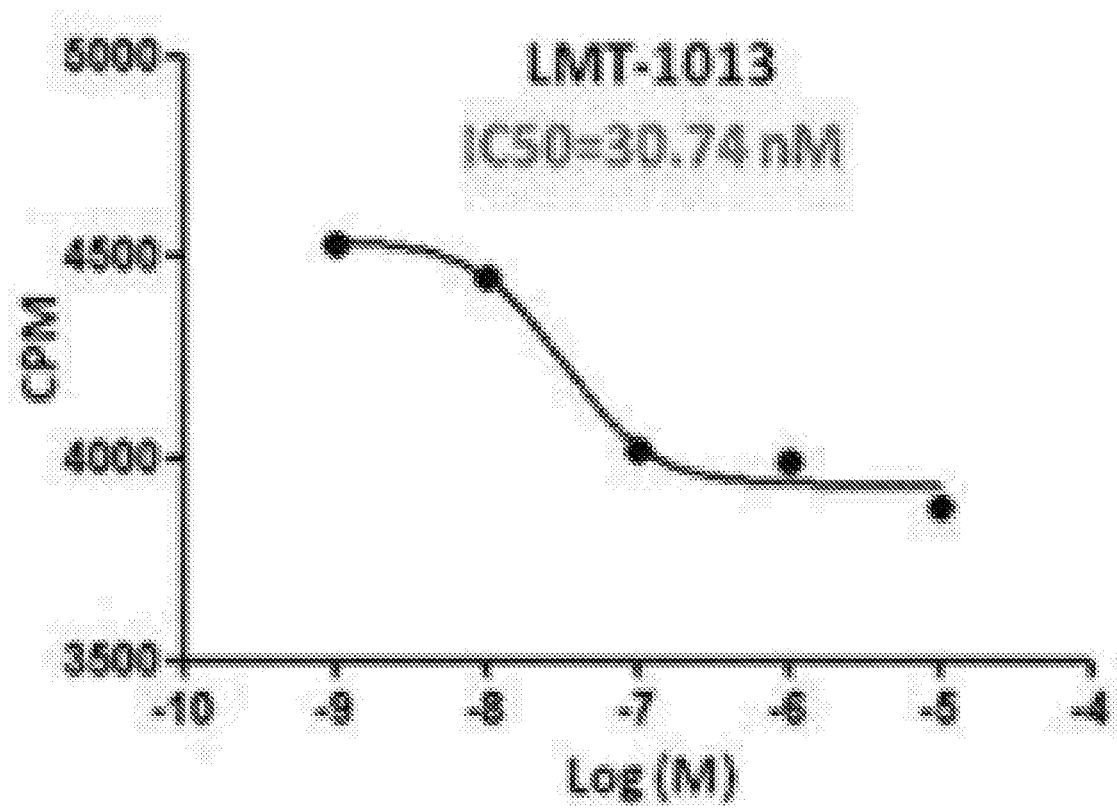

As a result, as shown in FIGS. 4A and 4B, it was confirmed that, in the BLT2-expressing cells (CHO-BLT2 cells), as the concentration of the compound of the present invention (LMT-696 or LMT-1013) was increased ($10^{-9}$, $10^{-8}$, $10^{-7}$, $10^{-6}$ and $10^{-5}$M), $LTB_4$ and BLT2 binding was inhibited, and the $IC_{50}$ of the LMT-696 and LMT-1013 compounds was 5.6 nM and 30.74 nM, respectively.

Experimental Example 5. Confirmation of Anticancer Effect Due to BLT2 Inhibition The inventors have reported from previous research that BLT2 regulates the generation of intracellular reactive oxygen species (ROS) and a cytokine interleukin-8 (IL-8) in breast cancer cells such as MDA-MB-231 and MDA-MB-453 cells, resulting in the control of the invasion and metastasis of cancer cells. Accordingly, it was confirmed that the generation of ROS and IL-8 expression were inhibited according to the treatment of the compound of the present invention in MDA-MB-231 and MDA-MB-453 breast cancer cells.

5-1. Preparation of Breast Cancer Cells

The breast cancer cells such as the MDA-MB-231 cells were obtained from Korean Cell Line Bank (Seoul, Korea), and the MDA-MB-435 cells were provided by J. H. Lee (Asan Medical Center, Seoul, Korea). These cells were cultured in an RPMI 1640 medium (Invitrogen) containing 10% FBS (Life Technologies, Inc.), 1% penicillin (50 units/mL), and an antibiotic antimycotic solution (Life Technologies, Inc.) at 37° C. under a 5% $CO_2$ condition.

5-2. Confirmation of Inhibitory Effect on Intracellular ROS Generation

Intracellular ROS ($H_2O_2$) generated according to the treatment of the compound of the present invention (LMT-696) was measured as a function of DCF fluorescence. Specifically, before ROS measurement, $2 \times 10^5$ cells were grown in 60-mm wells, and cultured in a FBS-supplemented RPMI 1640 medium for 24 hours. To evaluate the effect of the compound of the present invention, the cells were treated with the compound (LMT-696) for 30 minutes. To measure the intracellular ROS, the cells were cultured with 20 μM of a $H_2O_2$-sensitive fluorescent material such as $H_2DCFDA$ [Molecular Probes (Eugene, Oreg.)] at 37° C. in a dark and humidified $CO_2$ incubator for 20 minutes. The $H_2DCFDA$ was hydrolyzed to DCF in the cells, and oxidized to DCF exhibiting high fluorescence in the presence of $H_2O_2$, and thus the ROS amount was measured using as such property. In addition, to confirm the ROS generation using a detector, the cells were harvested using trypsin-EDTA, and resuspended in serum-free RPMI 1640 without phenol red. A DCF fluorescent degree was measured with excitation and emission wavelengths at 488 and 530 nm, respectively, using a FACS Calibur flow cytometer (Becton Dickinson, N.J.).

Figure 5A:
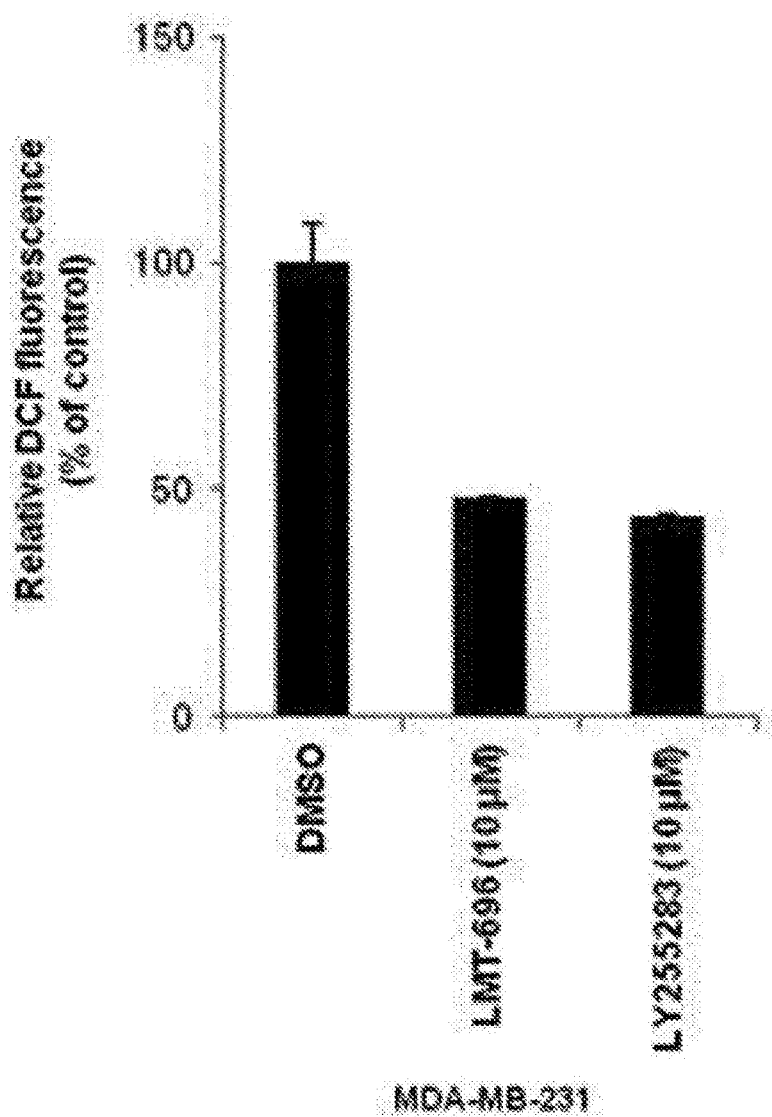
FIGS. 5A and 5B show the results of confirming an effect of inhibiting the generation of reactive oxygen species in MDA-MB-231 cells or MDA-MB-435 cells by treatment of a compound of the present invention.
Figure 5B:
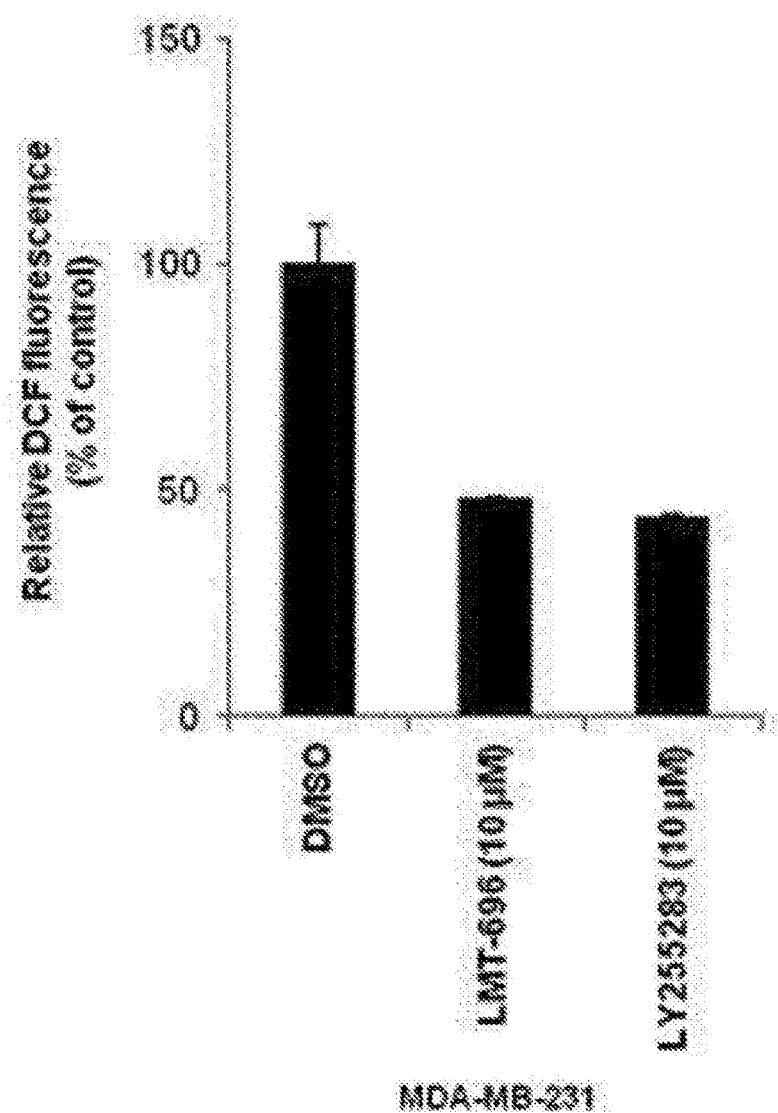

As a result, as shown in FIGS. 5A and 5B, it was confirmed that, when treated with the compound of the present invention (LMT-696), the breast cancer cells such as the MDA-MB-231 and MDA-MB-435 cells exhibited significant inhibition of the ROS generation.

5-3. Confirmation of Inhibitory Effect on IL-8 Expression

To confirm the IL-8 expression according to the treatment of the compound of the present invention, total RNA was isolated from cells using Easy Blue (Intron, Sungnam, Korea), and quantified by absorbance at 260 nm. Complementary DNA (cDNA) was synthesized with the RNA (1.25 μg) through reverse transcription using a polymerase chain reaction (PCR) technique. An expression level was determined using primers specifically binding to IL-8 and glyceraldehyde-3-phosphate dehydrogenase (GAPDH).

Figure 6A:
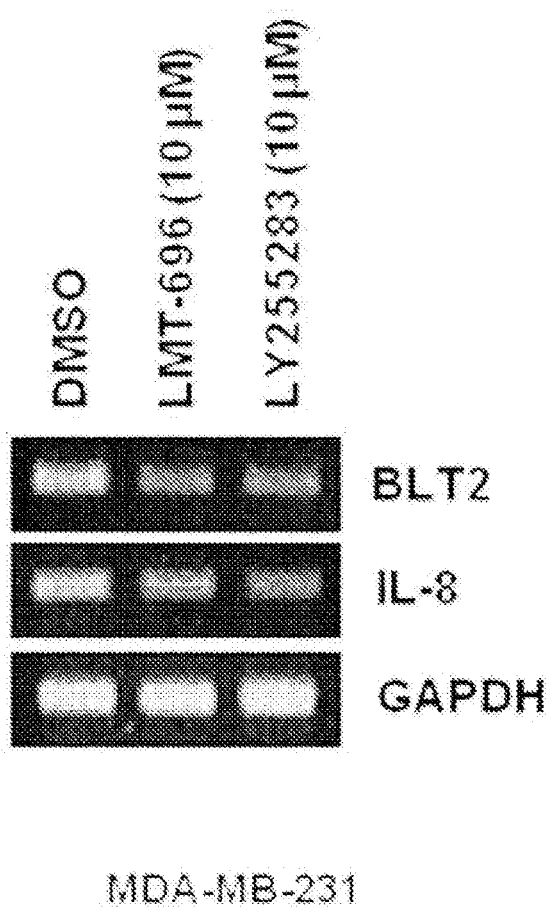
FIGS. 6A and 6B show the results of confirming an effect of inhibiting interleukin-8 (IL-8) expression levels in MDA-MB-231 cells or MDA-MB-435 cells by treatment of a compound of the present invention.
Figure 6B:
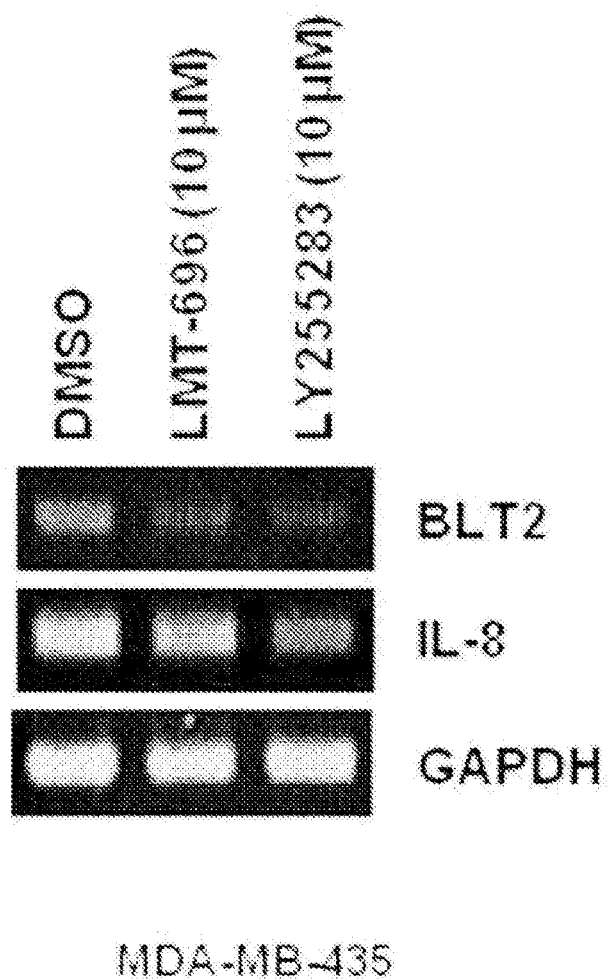

As a result, as shown in FIGS. 6A and 6B, it was confirmed that, when treated with the compound of the present invention (LMT-696), the breast cancer cells such as the MDA-MB-231 and MDA-MB-435 cells exhibited a significantly inhibited IL-8 expression level.

5-4. Confirmation of Inhibitory Effect on Invasion of Breast Cancer Cells

To detect the invasion of breast cancer cells according to the treatment of the compound of the present invention, BioCoat Matrigel Invasion Chambers (BD Biosciences, Bedford, Mass.) were used. $5 \times 10^4$ of the breast cancer cells were harvested with trypsin-EDTA, resuspended in 0.5% serum-containing RPMI 1640, and transferred to Matrigel inserts. Five percent serum-containing RPMI 1640 was added to the lower chamber, and the cells were cultured at 37° C. for 36 hours. Each filter was fixed with methanol for 3 minutes, and stained with hematoxylin and eosin for 10 minutes. The invasiveness of the cancer cells was quantified by cell counts on the lower side of the filter under an optical microscope (magnification, 200×). In each analysis, 6 fields were quantified. Each sample was analyzed twice, and the analysis was repeated three times.

Figure 7A:
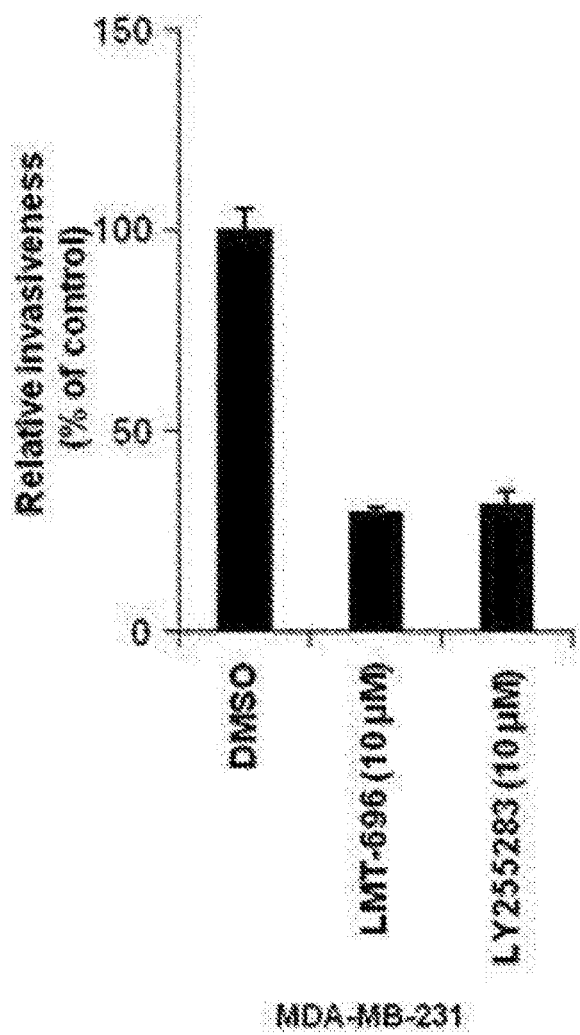
FIGS. 7A and 7B show the results of confirming an effect of inhibiting cancer cell invasion in MDA-MB-231 cells or MDA-MB-435 cells by treatment of a compound of the present invention.
Figure 7B:
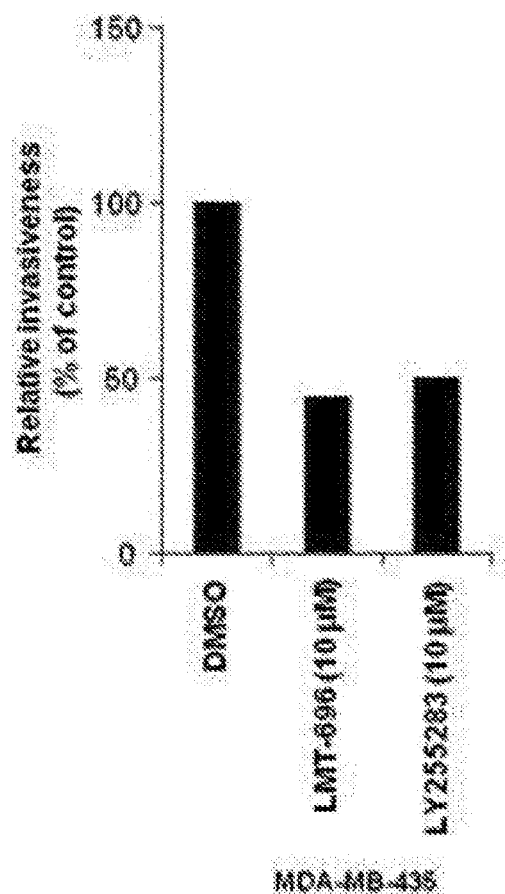

As a result, as shown in FIGS. 7A and 7B, when treated with the compound of the present invention (LMT-696), it was confirmed that the cancer cell invasion was inhibited 70% for the MDA-MB-231 cells, and inhibited 56% for the MDA-MB-435 cells.

5-5. Confirmation of Inhibitory Effect on Metastasis of Breast Cancer Cells

An experiment for the metastasis of breast cancer cells according to the treatment of the compound of the present invention was approved by the Ethics Committee of Korea University, and all experimental animals used in this experiment were treated according to the approved guidelines of the Korea University Animal Care and Use Committee. Six-week-old female nude mice (Charles River, Wilmington, Mass.) were injected with cancer cells to confirm cancer cell metastasis. The breast cancer cells were pre-treated with the compound of the present invention (LMT-696, 10 μM), LY255283, U75302 and DMSO, and 24 hours later, harvested with trypsin-EDTA, resuspended in PBS, and then $2 \times 10^6$ of the breast cancer cells were intraperitoneally injected into mice anesthetized with zoletil (50 mg/kg). After five days, the compound of the present invention (LMT-696; 2.5 mg/kg), LY255283 (2.5 mg/kg), U75302 (0.25 mg/kg) and DMSO were injected intraperitoneally three times every five days. At 15 weeks after the injection of the breast cancer cells, the mice were dissected to observe the cancer cell metastasis.

Figure 8:
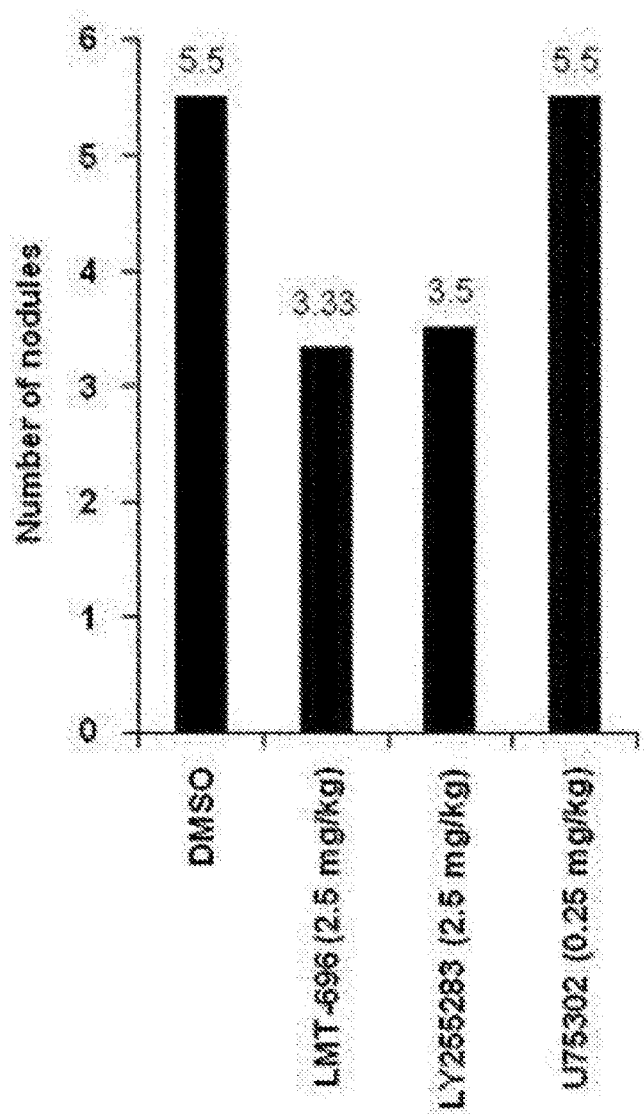
FIGS. 8, 9A and 9B show the results of confirming an effect of inhibiting cancer cell metastasis by treatment of a compound of the present invention.
Figure 9A:
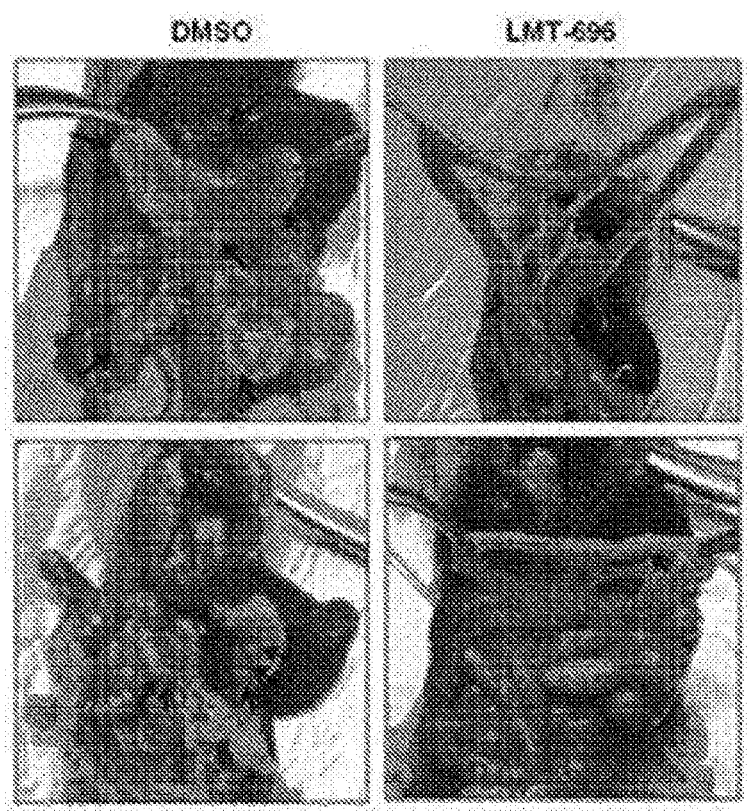
Figure 9B:
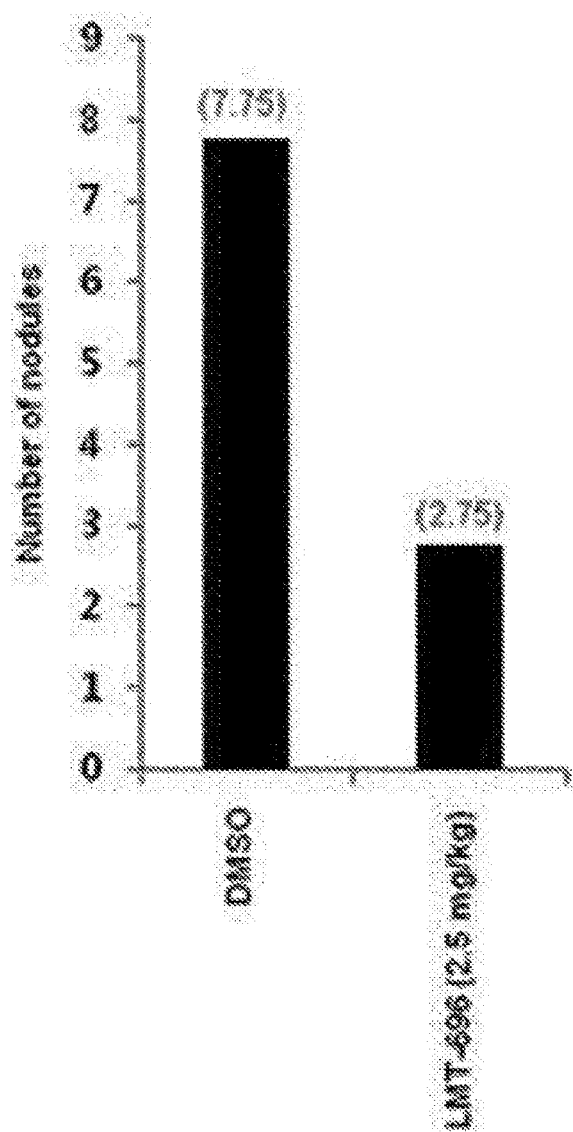

As a result, as shown in FIGS. 8, 9A and 9B, it was confirmed that the metastasis of the cancer cells (MDA-MB-231) was inhibited 40% by the treatment of the compound of the present invention (LMT-696), was inhibited 36% by the treatment of a positive control LY255283, as compared with the control, and was not inhibited by the treatment of U75302.

The results show that the compound of the present invention (LMT-696) can inhibit the generation of intracellular ROS and IL-8 of the cancer cells, and thus inhibit the invasiveness and metastasis of the cancer cells, and therefore the compound can be used as a pharmaceutical component having excellent anticancer efficiency.

Experimental Example 6. Confirmation of Anti-Asthma Effect by LBT2 Inhibition

Mast cells play a pivotal role in the initial reaction to asthma, and when an allergen enters the body from the outside through an airway, the mast cells are activated, thereby secreting various cytokines (interleukin-4 and interleukin-13). Due to the cytokines, the influx of inflammatory cells, the generation of mucus and the airway contraction occur. The inventors used 7-week-old (18 to 20 g) female BALB/c mice provided by Orient (Seoungnam, Korea) for the experiment to confirm the antiasthma effect, and then the asthma was induced in the mice. On the first and $14^{th}$ days, 2.5 mg of an adjuvant, aluminum hydroxide gel (alum; Pierce, Rockford, Ill.) was included in 20 mg of ovalbumin (OVA) to intraperitoneally sensitize female C57BL/6 mice. On the $21^{st}$, $22^{nd}$ and $23^{rd}$ days of two initial sensitizations, 1% OVA was sprayed into the mice using an ultrasonic nebulizer. The compound of the present invention (LMT-696; 5 mg/kg), LY255283 (5 mg/kg, Cayman) or DMSO was intraperitoneally injected at the 1 hour before the 1% OVA spraying. On the $24^{th}$ day of the initial sensitization, airway hyperresponsiveness (AHR) was detected, and on the $25^{th}$ day, the mice were dissected to observe asthma phenotypes, for example, inflammatory cytokine IL-4 expression and the influx of inflammatory cells (neutrophils). In the case of lipopolysaccharide (LPS)-induced severe asthma animal models, on the 0, $1^{st}$, $2^{nd}$ and $7^{th}$ days, 75 μg of OVA and 1 mg of LPS were intranasally injected into Balb/c mice for sensitization. On the $14^{th}$, $15^{th}$, $21^{th}$ and $22^{th}$ days, 50 μg of OVA was injected into the nose for a challenge. The compound of the present invention (LMT-1013) (1, 3, 10 or 30 mg/kg), montelukast (10 mg/kg, DRS) or a control buffer (10% DMA, 5% Tween 80, 85% brine) were treated one hour before the challenge by injecting 50 μg of OVA into the nose. On the $23^{rd}$ day of the initial sensitization, AHR was detected, and on the $24^{th}$ day, the mice were dissected to observe a severe asthma phenotype, for example, the influx of the inflammatory cells (neutrophils). In addition, the AHR detection was performed after an airway constrictor, methacholine (6.25 to 50 mg/ml depending on conditions), was administered to the mice. The administration of the airway constrictor was performed by spraying through an inlet of the chamber using an ultrasonic nebulizer for 3 minutes. The AHR was analyzed using an enhanced pause as the indicator of the asthma phenomenon. Bronchoalveolar lavage fluid cell counts were quantified by counting cells under an optical microscope (magnification, 200×). In each analysis, 4 fields were subjected to counting, each sample was analyzed twice, and the analysis was repeated three times.

Figure 10:
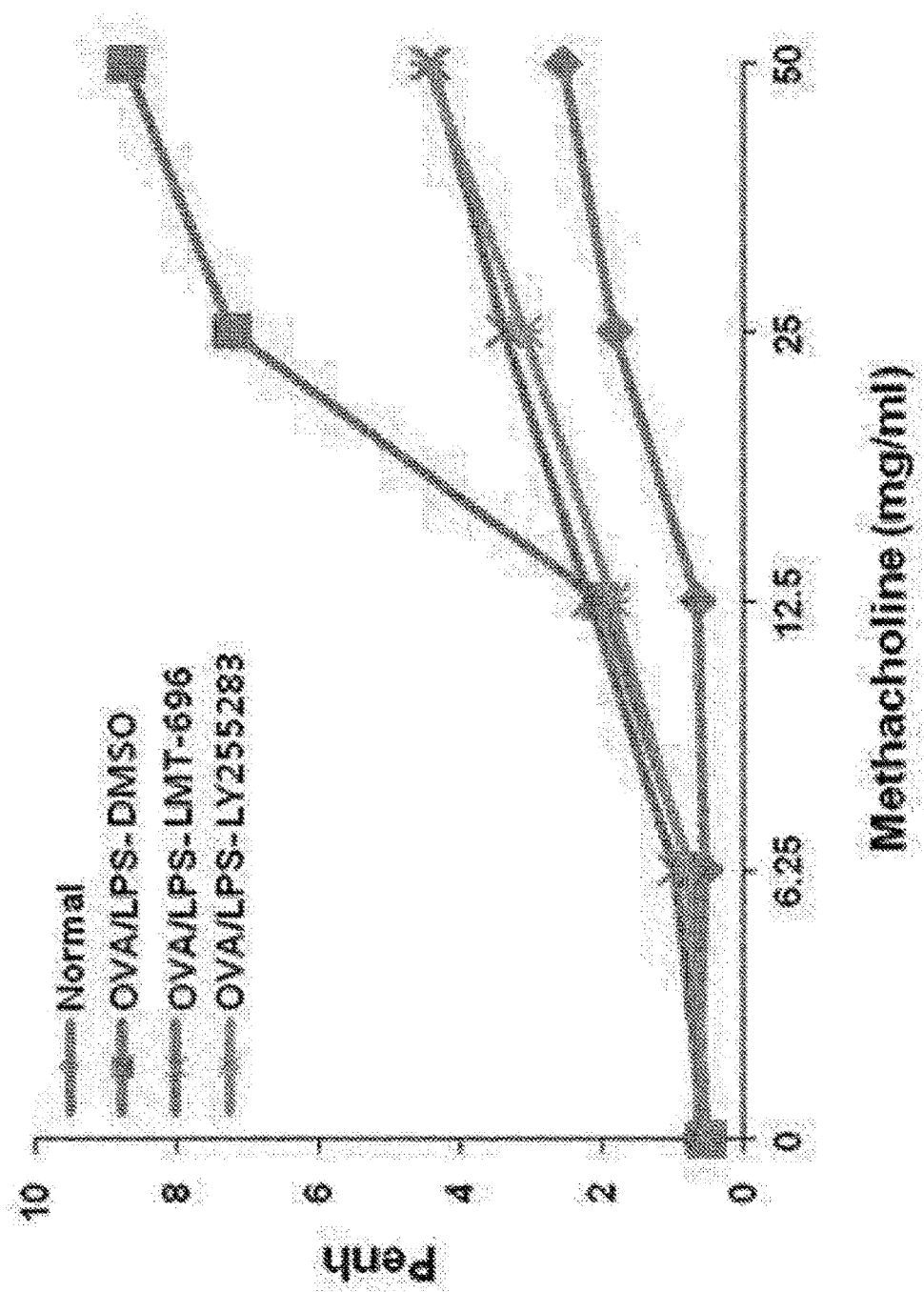
FIG. 10 shows the results of confirming an effect of reducing airway hyperresponsiveness (AHR) in severe asthma-induced mice by treatment of a compound of the present invention.
Figure 11:
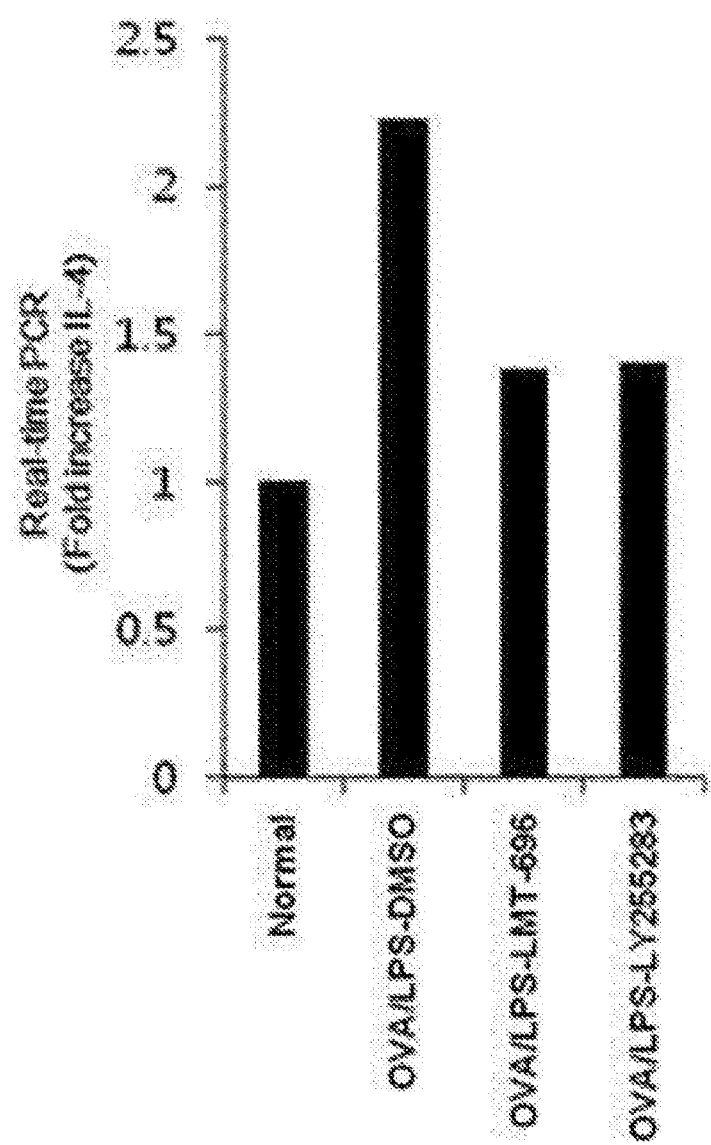
FIG. 11 shows the results of confirming an effect of reducing interleukin-4 (IL-4) generation in severe asthma-induced mice by treatment of a compound of the present invention.

In addition, as shown in FIGS. 10 and 11, it was confirmed that, when pre-treated with a positive control, LY255283, at 10 μM, the AHR of mice in which severe asthma was induced by administering 50 mg/ml of an airway constrictor was reduced by 69.2%, and the generation of IL-4 in the cells isolated from the abdominal cavity of the mice was reduced by 67.2%. Further, when pre-treated with the compound of the present invention (LMT-696) at 10 μM, the AHR of mice in which severe asthma was induced by administering 50 mg/ml of an airway constrictor was reduced by 70%, and the generation of IL-4 of cells isolated from the abdominal cavity of the mice was reduced by 70%.

Figure 12:
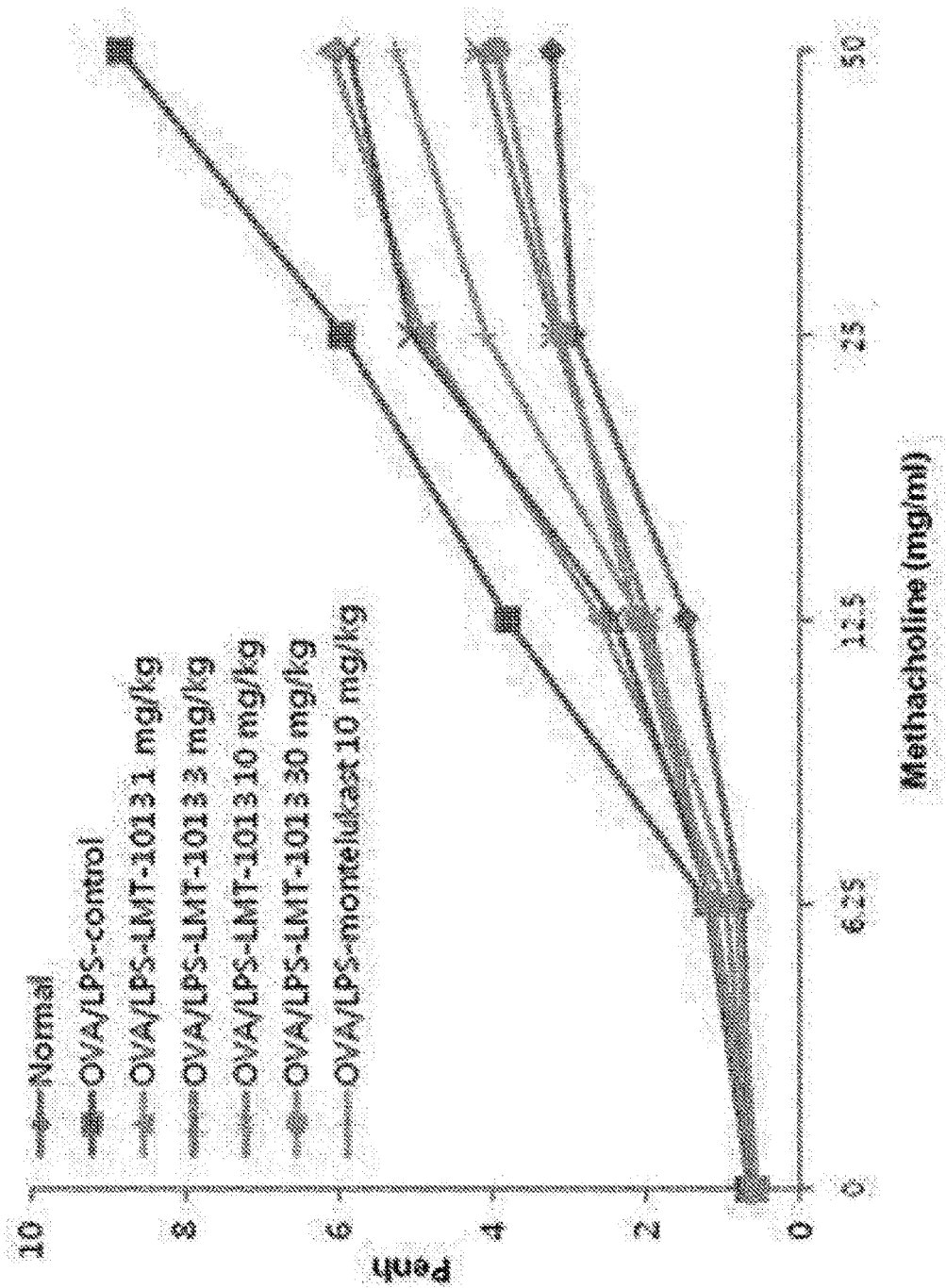
FIG. 12 shows the results of confirming an effect of reducing airway hyperresponsiveness (AHR) in severe asthma-induced mice by treatment of a compound of the present invention.

In addition, as shown in FIG. 12, in the asthma-induced mice (OVA+LPS), compared with mice in which asthma was not induced (Normal), AHR was increased 13-fold, and it was confirmed that, when pre-treated with the compound of the present invention (LMT-1013) at 1, 3, 10 and 30 mg/kg, the asthma-induced mice (OVA+LPS), compared with mice to which 50 mg/ml of the airway constrictor was administered, AHR was reduced 48.6%, 52.9%, 83.2%, and 87.3%, respectively. On the contrary, it was confirmed that, compared with the mice to which 50 mg/ml of the airway constrictor was administered, when pre-treated with a comparative material, montelukast, at 10 mg/kg, the AHR of the asthma-induced mice (OVA+LPS) was reduced 64%.

Figure 13A:
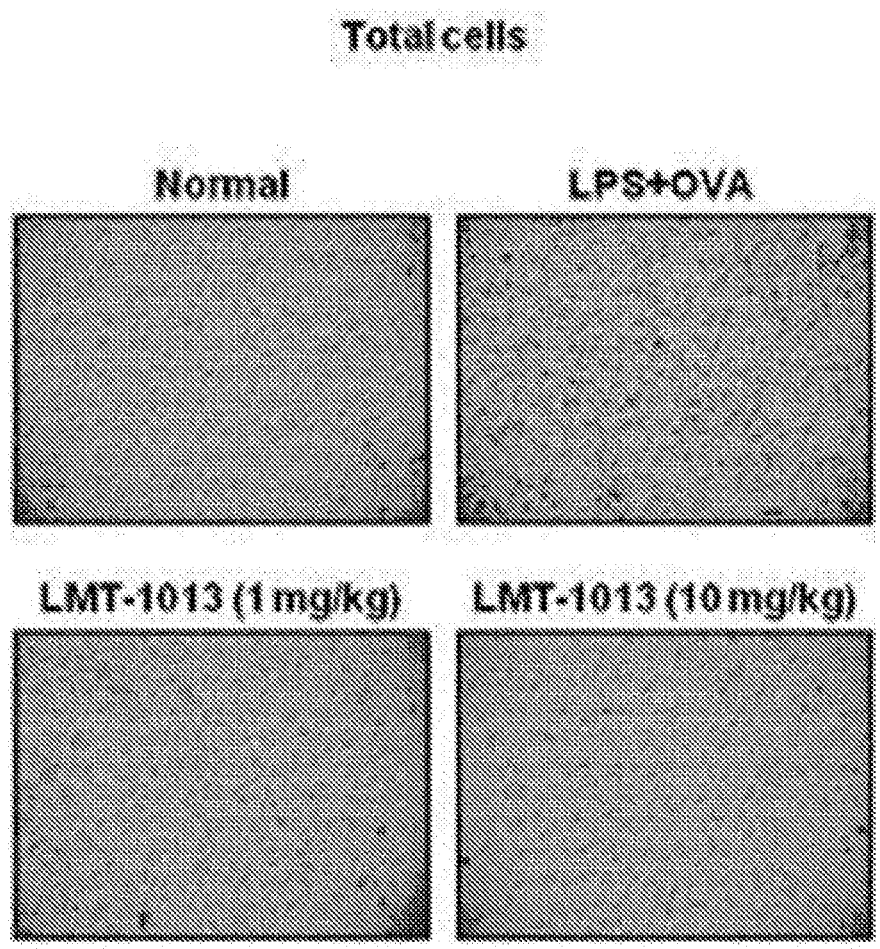
FIGS. 13A to 13C show the results of confirming that the influx of total cells and neutrophils into a mouse abdominal cavity is reduced in asthma-induced mice by treatment of a compound of the present invention.
Figure 13B:
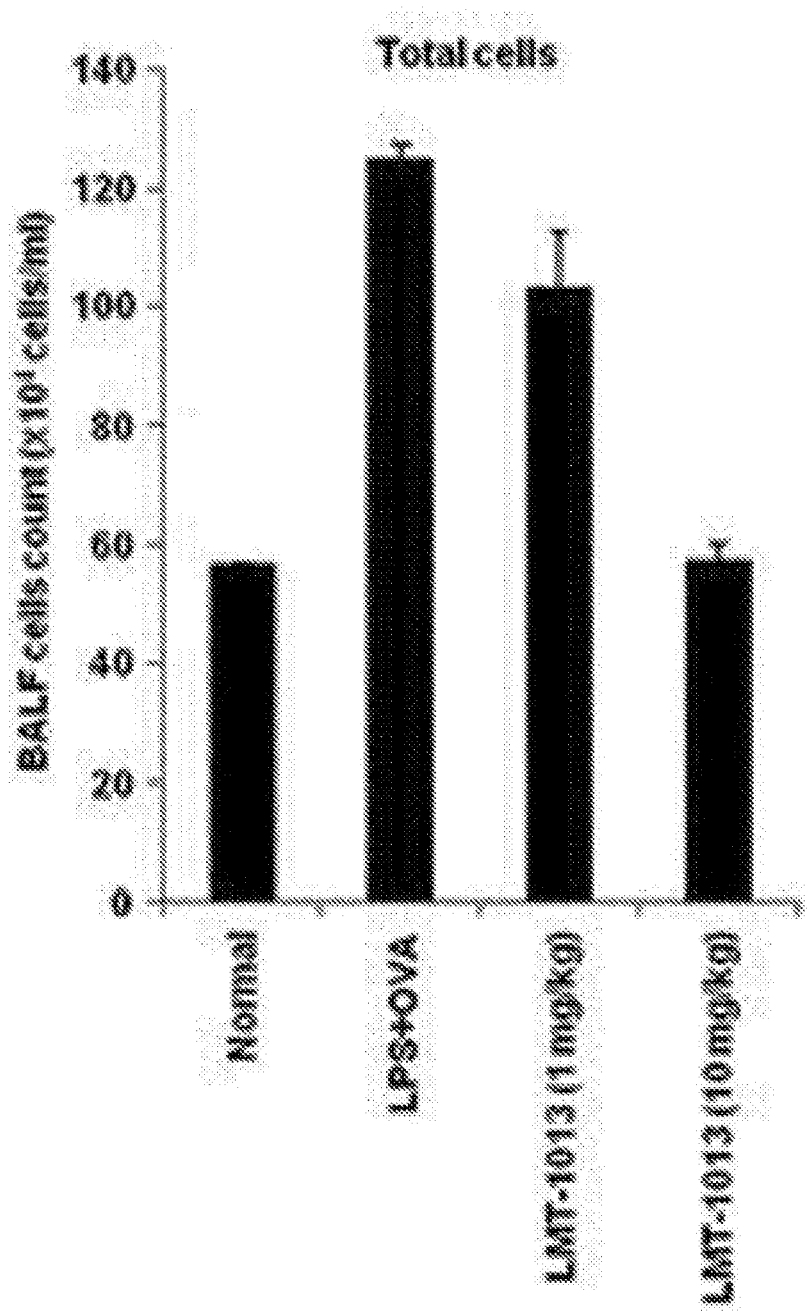
Figure 13C:
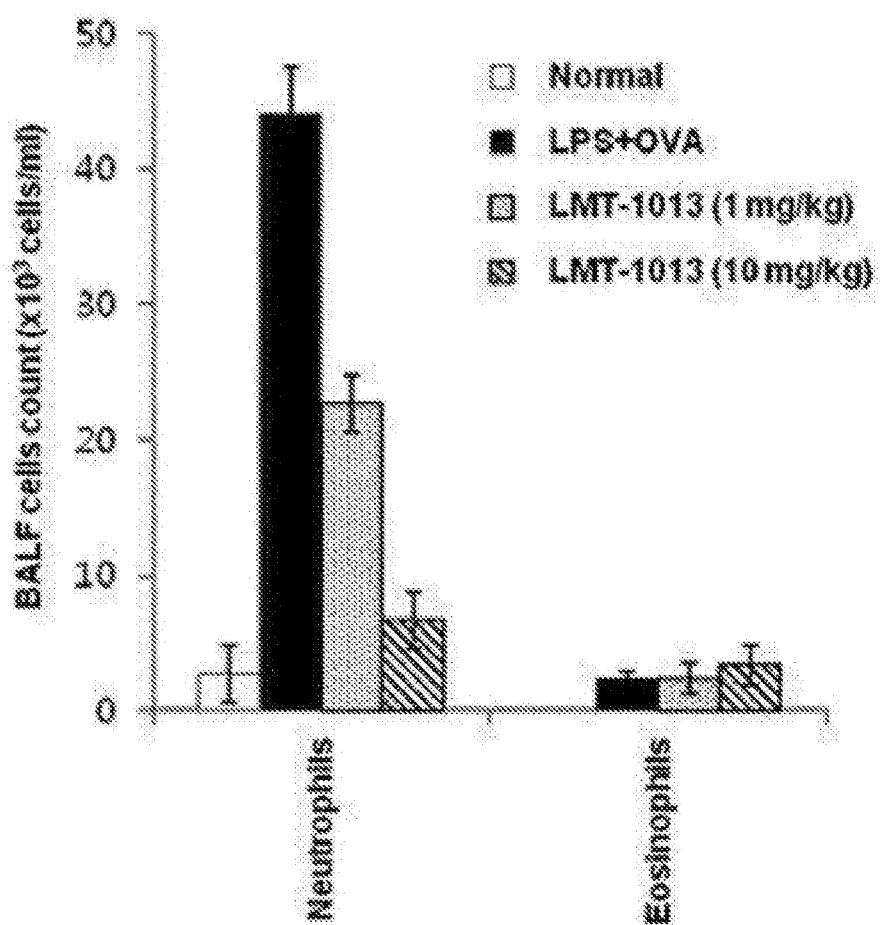

Further, as shown in FIGS. 13A, 13B and 13C, it was confirmed that, when the compound of the present invention (LMT-1013) was pre-treated at 1 and 10 mg/kg, in the asthma-induced mice (OVA+LPS), total cells and neutrophils entering the abdominal cavity of the mice were reduced, and particularly, the immune cells, that is, the neutrophils, were reduced 51.6% and 90.3%, respectively.

Figure 14A:
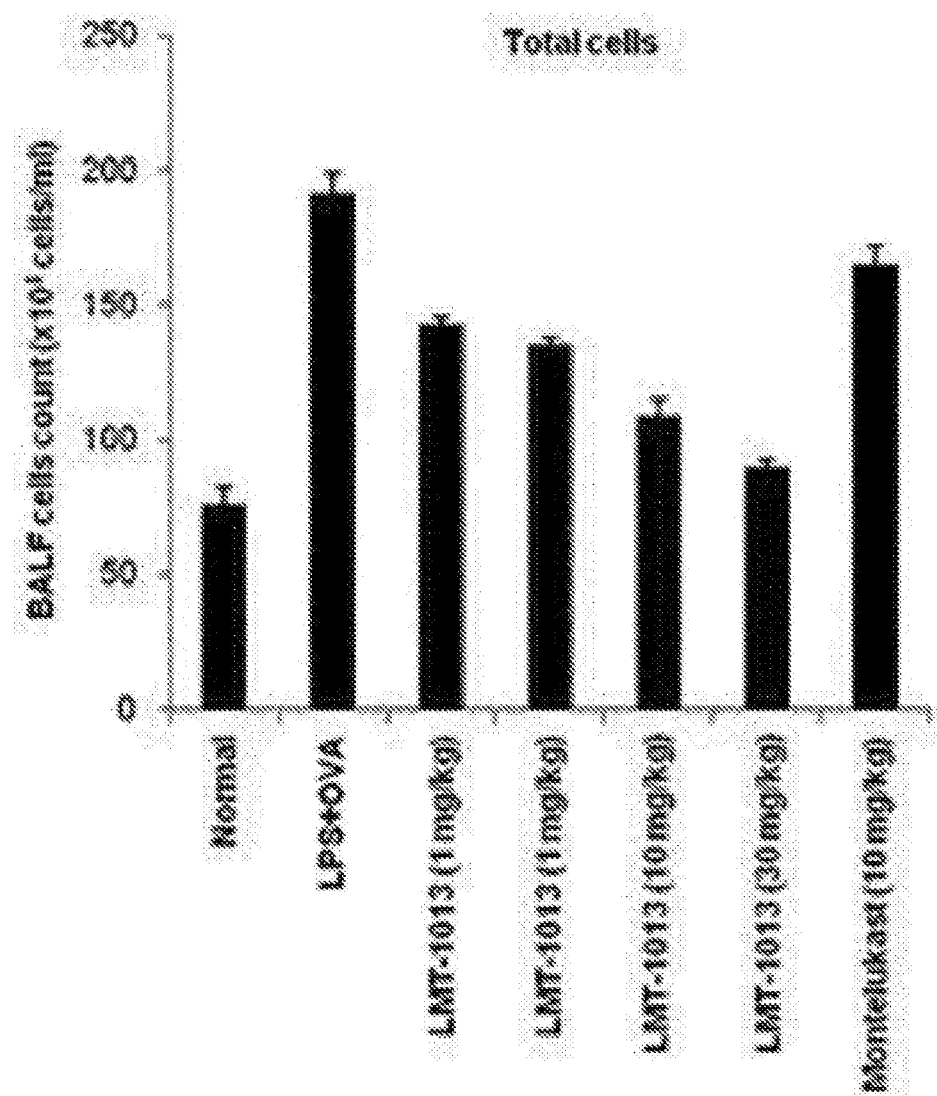
FIGS. 14A and 14B show the results of confirming that the influx of total cells and neutrophils into a mouse abdominal cavity in asthma-induced mice is reduced by treatment of a compound of the present invention.
Figure 14B:
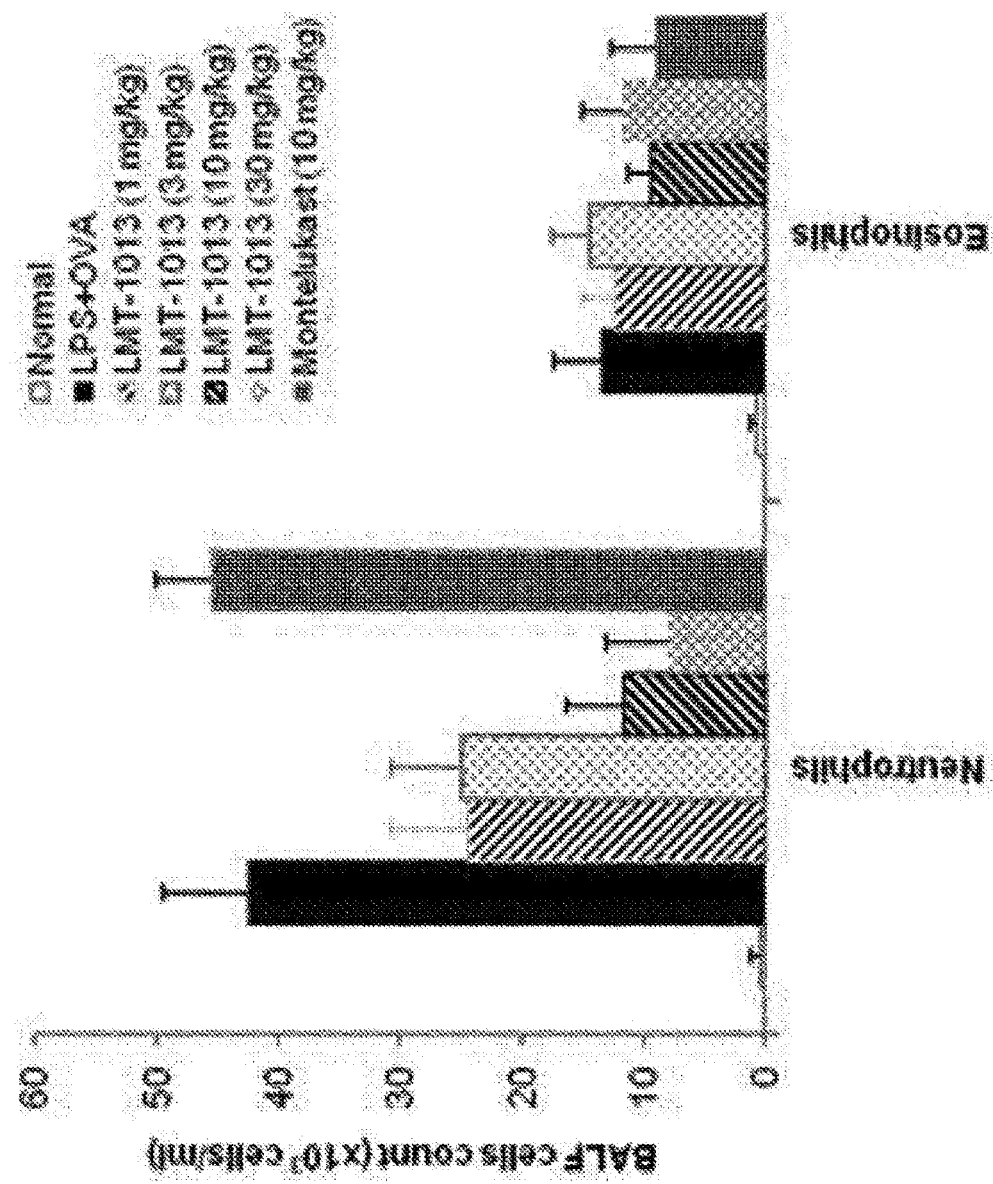

Furthermore, as shown in FIGS. 14A and 14B, it was confirmed that, when the compound of the present invention (LMT-1013) was pre-treated at 1, 3, 10, and 30 mg/kg, in the asthma-induced mice (OVA+LPS), total cells and neutrophils entering the abdominal cavity of the mice were reduced, and particularly, the neutrophils were reduced by 42.2%, 48.8%, 71.8%, and 88.3%, respectively. On the contrary, it was confirmed that, when the comparative material montelukast was pre-treated at 10 mg/kg, the immune cells, that is, the neutrophils, entering the abdominal cavity of the mice were not reduced.

The results showed that the compounds of the present invention (LMT-696 and LMT-1013) inhibited AHR in asthma animal models, the compound LMT-696 inhibited the generation of an inflammatory cytokine IL-4, and the compound LMT-1013 inhibited the influx of immune cells into the abdominal cavity, resulting in the alleviation of the symptoms of asthma, and therefore these compounds can be used as a pharmaceutical component having an antiasthma effect.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL AVAILABILITY

The present invention relates to a novel compound having BLT2 inhibitory activity and a pharmaceutical composition for preventing or treating an inflammatory disease, which includes the compound. The inventors identified a novel compound containing BTL2 inhibitory activity to solve the problems of the conventional compounds that had been designed to treat an inflammatory disease; for example, the instability in living organism and the difficulty on the mass production. In addition, it was experimentally confirmed that the present novel compound had an excellent effect on the enhancement of the cancer cell death, on the inhibition of the metastasis and chemotactic mobility, and on the anti-asthma activity. Therefore, the present novel compound can be used as a very effective pharmaceutical component for treating the inflammatory-related diseases.

The invention claimed is:
1. A method for inhibiting or treating an inflammatory disease in a subject in need thereof, comprising:
administering to the subject an effective amount of a pharmaceutical composition comprising a compound represented by Formula 1 or a pharmaceutically acceptable salt thereof:

[Formula I]

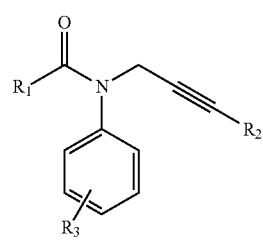

wherein,
$R_1$ is $C_1$ to $C_{10}$ alkyl;
$R_2$ is

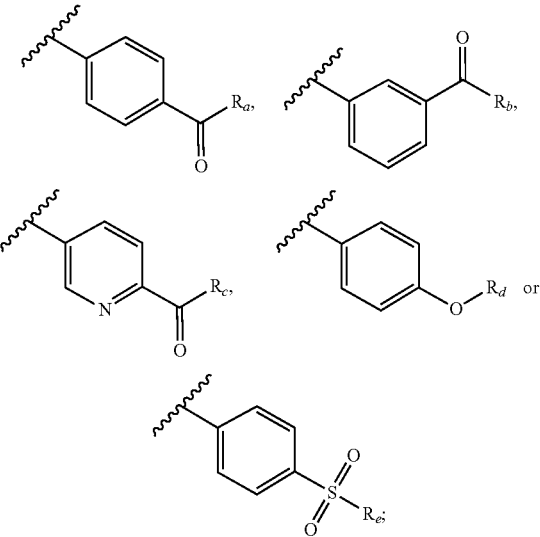

wherein,
$R_a$ is

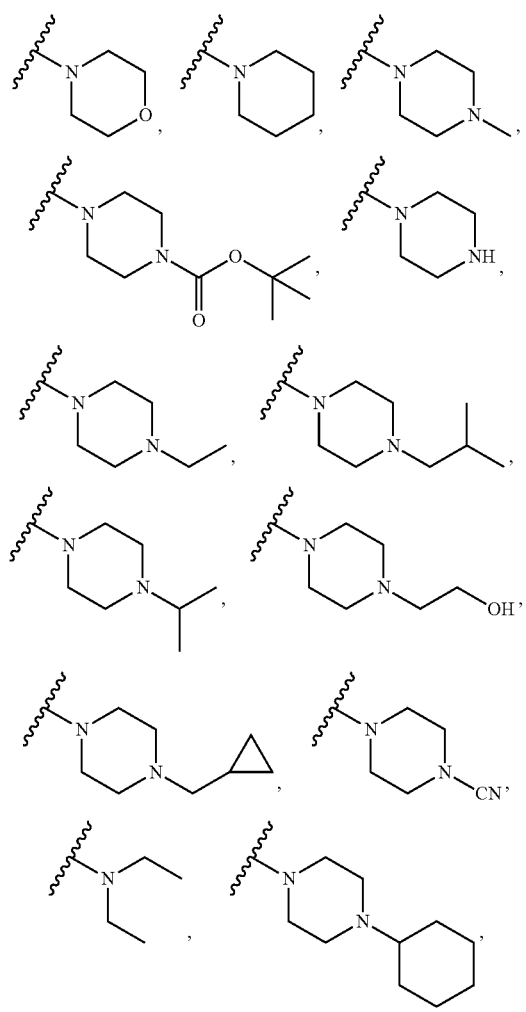

-continued
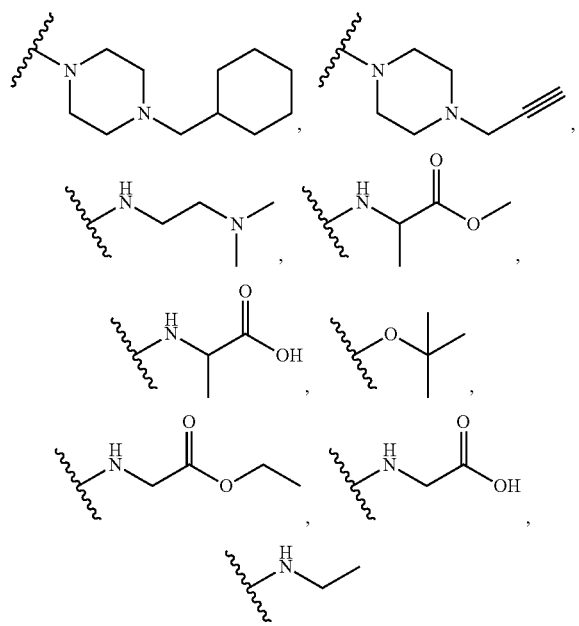
or hydroxy;
$R_b$ is
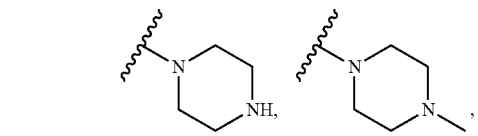
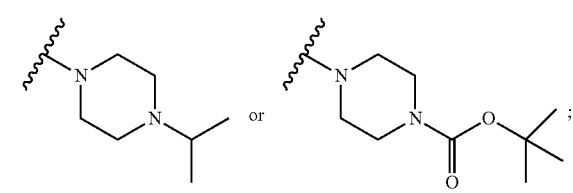
$R_c$ is
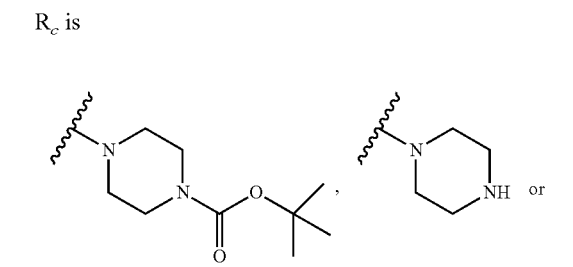
$R_d$ is hydrogen or and
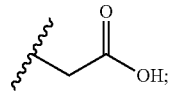 [SMILES: *CC(=O)O]
and
$R_e$ is
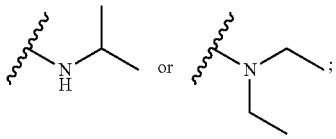
and
$R_3$ is hydrogen or fluorine and;
wherein the inflammatory disease is one that is responsive to inhibition of leukotriene B4 receptor 2 (BLT2) activity.
2. The method of claim 1, wherein
$R_1$ is n-Butyl;
$R_2$ is
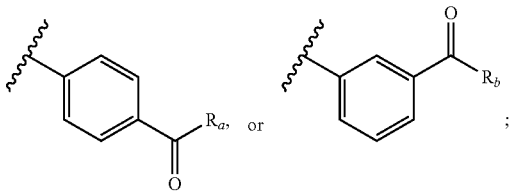
wherein,
$R_a$ is
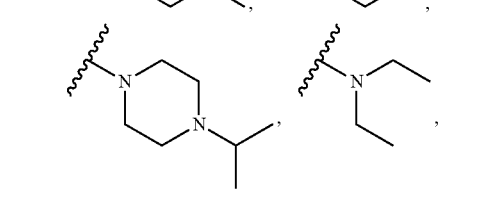
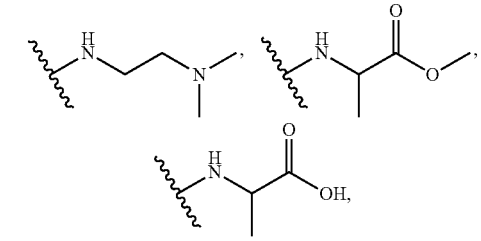

or hydroxy; and
R_b is

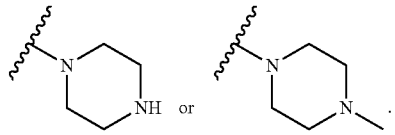

3. The method of claim 1, wherein the compound represented by Formula 1 is selected from the group consisting of:
tert-butyl 4-(4-(3-(N-phenylpentaneamido)prop-1-ynyl)benzoyl)piperazine-1-carboxylate;
N-phenyl-N-(3-(4-(piperazine-1-carbonyl)phenyl)prop-2-ynyl)pentaneamide;
N-(3-(4-(4-methylpiperazine-1-carbonyl)phenyl)prop-2-ynyl)-N-phenylpentaneamide;
N-(3-(4-(4-ethylpiperazine-1-carbonyl)phenyl)prop-2-ynyl)-N-phenylpentaneamide;
N-(3-(4-(4-isopropylpiperazine-1-carbonyl)phenyl)prop-2-ynyl)-N-phenylpentaneamide;
N-(3-(4-(4-(2-hydroxyethyl)piperazine-1-carbonyl)phenyl)prop-2-ynyl)-N-phenylpentaneamide;
N-(3-(4-(4-(cyclopropylmethyl)piperazine-1-carbonyl)phenyl)prop-2-ynyl)-N- phenylpentaneamide;
N-(3-(4-(4-cyclohexylpiperazine-1-carbonyl)phenyl)prop-2-ynyl)-N-phenylpentaneamide;
N-(3-(4-(4-(cyclohexylmethyl)piperazine-1-carbonyl)phenyl)prop-2-ynyl)-N-phenylpentaneamide;
N-(3-(4-(4-isobutylpiperazine-1-carbonyl)phenyl)prop-2-ynyl)-N-phenylpentaneamide;
N-phenyl-N-(3-(4-(4-(prop-2-ynyl)piperazine-1-carbonyl)phenyl)prop-2-ynyl)pentaneamide;
N-(3-(4-(4-cyanopiperazine-1-carbonyl)phenyl)prop-2-ynyl)-N-phenylpentaneamide;
tert-butyl 4-(4-(3-(N-(3-fluorophenyl)pentaneamido)prop-1-ynyl)benzoyl)piperazine-1-carboxylate;
N-(3-fluorophenyl)-N-(3-(4-(piperazine-1-carbonyl)phenyl)prop-2-ynyl)pentaneamide;
N-(3-fluorophenyl)-N-(3-(4-(4-isopropylpiperazine-1-carbonyl)phenyl)prop-2-ynyl)pentaneamide;
tert-butyl 4-(4-(3-(N-(4-fluorophenyl)pentaneamido)prop-1-ynyl)benzoyl)piperazine-1-carboxylate;
N-(4-fluorophenyl)-N-(3-(4-(piperazine-1-carbonyl)phenyl)prop-2-ynyl)pentaneamide;
N-(4-fluorophenyl)-N-(3-(4-(4-isopropylpiperazine-1-carbonyl)phenyl)prop-2-ynyl)pentaneamide;
N-(3-(4-(morpholine-4-carbonyl)phenyl)prop-2-ynyl)-N-phenylpentaneamide;
N-phenyl-N-(3-(4-(piperidine-1-carbonyl)phenyl)prop-2-ynyl)pentaneamide;
N,N-diethyl-4-(3-(N-phenylpentaneamido)prop-1-ynyl)benzamide;
N-phenyl-N-(3-(3-(piperazine-1-carbonyl)phenyl)prop-2-ynyl)pentaneamide;
N-(3-(3-(4-methylpiperazine-1-carbonyl)phenyl)prop-2-ynyl)-N-phenylpentaneamide;
N-(3-(3-(4-isopropylpiperazine-1-carbonyl)phenyl)prop-2-ynyl)-N-phenylpentaneamide;
tert-butyl-4-(3-(3-(N-(4-fluorophenyl)pentaneamido)prop-1-ynyl)benzoyl)piperazine-1-carboxylate;
N-(4-fluorophenyl)-N-(3-(3-(piperazine-1-carbonyl)phenyl)prop-2-ynyl)pentaneamide;
N-(4-fluorophenyl)-N-(3-(3-(4-isopropylpiperazine-1-carbonyl)phenyl)prop-2-ynyl)pentaneamide;
N-(3-(4-hydroxyphenyl)prop-2-ynyl)-N-phenylpentaneamide; 2-(4-(3-(N-phenylpentaneamido)prop-1-ynyl)phenoxy)acetic acid;
tert-butyl 4-(5-(3-((N-phenylpentaneamido)prop-1-yn-1-yl)picolinoyl)piperazine-1-carboxylate;
N-phenyl-N-(3-(6-(piperazine-1-carbonyl)pyridine-3-yl)prop-2-yn-1-yl)pentaneamide;
N-(3-(6-isopropylpiperazine-1-carbonyl)pyridine-3-yl)prop-2-yn-1-yl)pentaneamide;
N,N-diethyl-4-(3-(N-(3-fluorophenyl)pentaneamido)prop-1-yn-1-yl)benzamide;
N,N-diethyl-4-(3-(N-(4-fluorophenyl)pentaneamido)prop-1-yn-1-yl)benzamide;
N-(3-(4-(N,N-diethylsulfamoyl)phenyl)prop-2-ynyl)-N-phenylpentaneamide;
N-(3-(4-(N-isopropylsulfamoyl)phenyl)prop-2-ynyl)-N-phenylpentaneamide;
tert-butyl 4-(3-(N-phenylpentaneamido)prop-1-yn-1-yl)benzoate; 4-(3-(N-phenylpentaneamido)pro-1-yn-1-yl)benzoic acid;
N-ethyl-4-(3-(N-phenylpentaneamido)prop-1-yn-1-yl)benzamide;
N-(2-(diethylamino)ethyl)-4-(3-(N-phenylpentaneamido)prop-1-yn-1-yl)benzamide;
ethyl 2-(4-(3-(N-phenylpentaneamido)prop-1-yn-1-yl)benzamido)acetate;
2-(4-(3-(N-phenylpentaneamido)prop-1-yn-1-yl)benzamido)acetic acid;
methyl 2-(4-(3-(N-phenylpentaneamido)prop-1-yn-1-yl)benzamido)propanoate;
2-(4-(3-(N-phenylpentaneamido)prop-1-yn-1-yl)benzamido)propionic acid;
2-(4-(3-(N-(3-fluorophenyl)pentaneamido)prop-1-ynyl)phenoxy)acetic acid 4-(3-(N-phenylpentaneamido)prop-1-yn-1-yl)benzoic acid;
N-phenyl-N-(3-(4-(piperazine-l-carbonyl)phenyl)prop-2-ynyl)pentanamide;
N-(2-(dimethylamino)ethyl)-4-(3-(N-phenylpentaneamido)prop-1-yn-1-yl)benzamide;
2-(4-(3-(N-phenylpentaneamido)prop-1-yn-1-yl)benzamido)propanoic acid; and
2-(4-(3-(N-(4-fluorophenyl)pentaneamido)prop-1-ynyl)phenoxy)acetic acid.

4. The method of claim 1, wherein the compound represented by Formula 1 is selected from the group consisting of:
N-(3-(4-(4-methylpiperazine-1-carbonyl)phenyl)prop-2-ynyl)-N-phenylpentaneamide;
N-phenyl-N-(3-(4-(piperazine-1-carbonyl)phenyl)prop-2-ynyl)pentanamide;
N-(3-(4-(4-isopropylpiperazine-1-carbonyl)phenyl)prop-2-ynyl)-N-phenylpentaneamide;
N-phenyl-N-(3-(3-(piperazine-1-carbonyl)phenyl)prop-2-ynyl)pentaneamide;
N-(4-fluorophenyl)-N-(3-(4-(4-isopropylpiperazine-1-carbonyl)phenyl)prop-2-ynyl)pentaneamide;
N-(3-(3-(4-isopropylpiperazine-1-carbonyl)phenyl)prop-2-ynyl)-N-phenylpentaneamide;
N,N-diethyl-4-(3-(N-phenylpentaneamido)prop-1-ynyl)benzamide;
N-(3-fluorophenyl)-N-(3-(4-(4-isopropylpiperazine-1-carbonyl)phenyl)prop-2-ynyl)pentaneamide;
4-(3-(N-phenylpentaneamido)prop-1-yn-1-yl)benzoic acid;
N-(2-(dimethylamino)ethyl)-4-(3-(N-phenylpentaneamido)prop-1-yn-1-yl)benzamide;
methyl 2-(4-(3-(N-phenylpentaneamido)prop-1-yn-1-yl)benzamido)propanoate; and 2-(4-(3-(N-phenylpentaneamido)prop-1-yn-1-yl)benzamido)propanoic acid.

5. The method of claim 1, wherein the inflammatory disease is selected from the group consisting of asthma, atherosclerosis, pruritus, rheumatoid arthritis and inflammatory enteropathy.

6. The method of claim 1, wherein the pharmaceutical composition inhibits leukotriene B4 receptor 2 (BLT2) activity.

7. The method of claim 1, wherein the inflammatory disease is a cancer, wherein the cancer is any cancer caused by the overexpression of BLT2 or Ras that is responsive to inhibition of BLT2.

8. The method of claim 7, wherein the cancer is selected from the group consisting of kidney cancer, prostate cancer, pancreatic cancer, breast cancer, brain tumors, skin cancer and liver cancer.

9. The method of claim 7, wherein the cancer is a breast cancer.

10. The method of claim 1, wherein the inflammatory disease is asthma.

11. The method of claim 1, wherein the compound represented by Formula I is

N-(3-(4-(4-methylpiperazine-1-carbonyl)phenyl)prop-2-ynyl)-N-phenylpentanamide,

N-phenyl-N-(3-(4-(piperazine-1-carbonyl)phenyl)prop-2-ynyl)pentanamid,

N-(3-(4-(4-isopropylpiperazine-1-carbonyl)phenyl)prop-2-ynyl)-N-phenylpentaneamide, or 4-(3-(N-phenylpentaneamido)prop-1-yn-1-yl)benzoic acid.

\* \* \* \* \*